United States Patent
Lin et al.

(10) Patent No.: US 8,410,095 B2
(45) Date of Patent: Apr. 2, 2013

(54) THIAZOLOPYRIMIDINONE DERIVATIVES AS PI3 KINASE INHIBITORS

(75) Inventors: Hong Lin, Collegeville, PA (US); Juan I. Luengo, Collegeville, PA (US); Ralph A. Rivero, Collegeville, PA (US); Mark James Schulz, Collegeville, PA (US); Ren Xie, Collegeville, PA (US); Jin Zeng, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/319,375

(22) PCT Filed: May 20, 2010

(86) PCT No.: PCT/US2010/035535
§ 371 (c)(1),
(2), (4) Date: Nov. 8, 2011

(87) PCT Pub. No.: WO2010/135504
PCT Pub. Date: Nov. 25, 2010

(65) Prior Publication Data
US 2012/0053147 A1    Mar. 1, 2012

Related U.S. Application Data

(60) Provisional application No. 61/179,768, filed on May 20, 2009.

(51) Int. Cl.
*A61K 31/535* (2006.01)
*C07D 413/14* (2006.01)

(52) U.S. Cl. ................................. 514/234.2; 544/117
(58) Field of Classification Search .................. 544/117; 514/234.2
See application file for complete search history.

(56) References Cited

U.S. PATENT DOCUMENTS
2008/0207609 A1    8/2008    Shuttleworth et al.
2008/0306060 A1    12/2008    Alexander et al.

OTHER PUBLICATIONS

Yaguchi, et al., Antitumor Activity of ZSTK474, a New Phosphatidylinositol 3-Kinase Inhibitor, J. Ntl Cancer Inst 98 (8):545-556 (2006). Abstract p. 547. pp. 550-551.

*Primary Examiner* — Rebecca Anderson
(74) *Attorney, Agent, or Firm* — J. Scott Young

(57) ABSTRACT

This invention relates to novel compounds of formula (I):

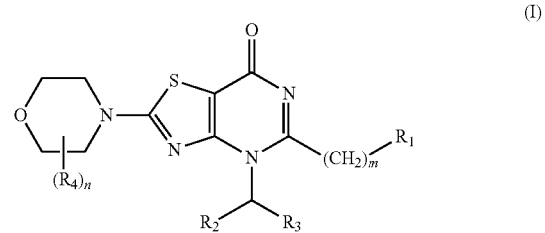

and derivatives thereof useful for the modulation, notably the inhibition of the activity or function of the phosphoinositide 3' OH kinase family (hereinafter PI3 kinases), suitably, PI3Kα, PI3Kδ, PI3Kβ, and/or PI3Kγ.

10 Claims, No Drawings

THIAZOLOPYRIMIDINONE DERIVATIVES AS PI3 KINASE INHIBITORS

CROSS-REFERENCE TO RELATED APPLICATIONS

This application is filed pursuant to 35 U.S.C. §371 as a United States National Phase Application of International Patent Application Serial No. PCT/US2010/035535 filed May 20, 2010, which claims priority to U.S. Application No. 61/179,768 filed May 20, 2009, the contents of which are incorporated herein by reference.

FIELD OF THE INVENTION

This invention relates to the use of thiazolopyrimidinone derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of thiazolopyrimidinones in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective thiazolopyrimidinones compounds for treating cancer.

BACKGROUND OF THE INVENTION

The phosphoinositide 3-kinase (PI3K) pathway is among the most commonly activated in human cancer and the importance in carcinogenesis is well established. (Samuels Y and Ericson K. Oncogenic PI3K and its role in cancer. *Current Opinion in Oncology*, 2006; 18:77-82) Initiation of signaling begins with the phosphorylation of phosphatidylinositol-4,5-bisphosphate (PIP2) to produce phosphatidylinositol-3,4,5-P3 (PIP3). PIP3 is a critical second messenger which recruits proteins that contain pleckstrin homology domains to the cell membrane where they are activated. The most studied of these proteins is AKT which promotes cell survival, growth and proliferation.

The PI3K family consists of 15 proteins that share sequence homology, particularly within their kinase domains, but have distinct substrate specificities and modes of regulation. (Vivanco I and Sawyers CL. The phosphatidylinositol 3-kinase-AKT pathway in human cancer. *Nature Reviews Cancer*, 2002; 2:489-501) Class I PI3Ks are heterodimers consisting of a p110 catalytic subunit complexed to one of several regulatory subunits collectively referred to as p85 and have been the most extensively studied in the context of tumorgenesis. The class 1A PI3K catalytic subunits comprise the p110α, p110β, and p110δ isoforms, which associate with one of five different regulatory subunits encoded by three separate genes. A single class 1B PI3K catalytic isoform p1110γ interacts with one of two associated regulatory subunits. (Crabbe T, Welham M J, Ward S G, The PI3k inhibitor arsenal: choose your weapon *Trends in Biochem Sci*, 2007; 32:450-456) Class 1 PI3Ks are primarily responsible for phosphorylating the critical PIP2 signaling molecule.

The link between the PI3K pathway and cancer was confirmed by a study which identified somatic mutations in the PIK3CA gene encoding the p110α protein. Subsequently, mutations in PIK3CA have been identified in numerous cancers including colorectal, breast, glioblastomas ovarian and lung. In contrast to PIK3CA, no somatic mutations in the β isoform have been identified. However, in overexpression studies the PI3Kβ isoform has been implicated as necessary for transformation induced by the loss or inactivation of the PTEN tumor suppressor both in vitro and in vivo. (Torbett N E, Luna A, Knight Z A, et al., A chemical screen in diverse breast cancer cell lines reveals genetic enhancers and suppressors of sensitivity to PI3K isotype-selective inhibition. *Biochem J* 2008; 415:97-110; Zhao J J, Liu Z, Wang L, Shin E, Loda M F, Roberts T M, The oncogenic properties of mutant p110a and p110b phosphatidylinositol 3-kinases in human mammary epithelial cells. *Proc Natl Acad Sci USA* 2005; 102:18443-8) Consistent with this finding, overexpression of the PIK3CB gene has been identified in some bladder, colon, glioblastomas and leukemias and siRNA mediated knockdown of p110β in glioblastoma cell lines results in suppression of tumor growth in vitro and in vivo. (Pu P, Kang C, Zhang Z, et al., Downregulation of PIK3CB by siRNA suppresses malignant glioma cell growth in vitro and in vivo. *Technolo Cancer Res Treat* 2006; 5:271-280) More recent data using shRNA demonstrated that downregulation of p100β and not p110α resulted in PI3K pathway inactivation and subsequent inactivation of tumor cell growth in PTEN deficient cancers cells both in vitro and in vivo. (Wee S, Wiederschain, Maira S-M, Loo A, Miller C, et al., PTEN-deficient cancers depend on PIK3CB. *Proc Natl Acad Sci* 2008; 105:13057-13062) Consistent with a role of PIK3CB signaling in PTEN null tumors, p110β was reported to be essential to the transformed phenotype in a PTEN-null prostate cancer model. (Jia S, Liu Z, Zhang S, Liu P, Zhang L, et al., Essential roles of PI(3)K-p110b in cell growth, metabolism and tumorgenesis. *Nature* 2008;10:1038) Taken together, these findings indicate PI3K p110β as a promising target in cancer therapy.

Clinally, the loss of PTEN expression in the germ line is the cause of the majority of cases of Cowden's syndrome, a multiple hamartomas syndrome that includes throid neoplasias (benigh and malignant) as part of the phenotype. Liaw, D., Marsh, D. J., Li, J., et al., 1997. Germline mutations of the pten gene in cowden disease, an inherited breast and thyroid cancer syndrome. Nat. Genet. 16, 64-67. PTEN-null cancers rely almost exclusively on PI3K-beta for growth signaling, thus an inhibitor will alleviate symptoms of Cowden Syndrome. Motoyasu Saji and Matthew D. Ringel. The PI3K-Akt-mTOR pathway in initiation and progression of thyroid tumors; Molecular and Cellular Endocrinology 321 (2010) 20-28.

SUMMARY OF THE INVENTION

This invention relates to novel compounds of formula (I)

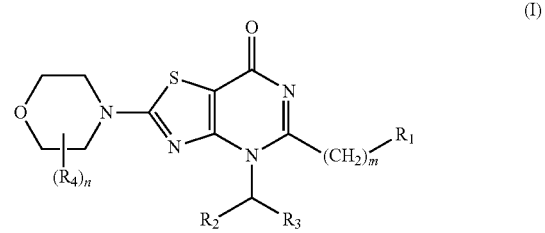

wherein
R1 is selected from the group consisting of: H, C1-3alkyl, —SC1-6alkyl, —OC1-6alkyl, NRaRb, hydroxy, —SH, NH—NH2, C3-6cycloalkyl, C4-6heterocycloalkyl, —SO2Ph, —OPh, —SPh, —SO2(C1-3alkyl), —O(arylalkyl), and phenyl;
R2 is H or C1-3alkyl;
R3 is selected from the group consisting of: C1-6alkyl, C3-7cycloalkyl, C4-6heterocycloalkyl, alkylcarboxy, aryl, arylalkyl, and heteroaryl;
each R4 is independently selected from the group consisting of: C1-3alkyl, alkoxy, amide, and ester;
n is 0-2, m is 0-3; and
Ra and Rb are each independently H, or C1-3alkyl;
or a pharmaceutically acceptable salt thereof.

This invention also relates to pharmaceutical compositions of compounds of formula (I). This invention also relates to methods of treating cancer which comprises administering an effective amount of a compound of formula (I) to a human in need thereof.

DETAILED DESCRIPTION OF THE INVENTION

This invention relates to novel compounds of formula (I) as described above.

This invention also relates to compounds of formula (I), wherein
R1 is selected from the group consisting of: H, C1-3alkyl, alkoxy, —SMe, NH2, NHMe, and cyclopropyl;
R2 is H or C1-3alkyl;
R3 is C1-6alkyl or aryl;
each R4 is independently selected from the group consisting of: C1-3alkyl, amide, and ester;
n is 0-2, m is 0-3; and
Ra and Rb are each independently H, or C1-3 alkyl;
or a pharmaceutically acceptable salt thereof.

This invention also relates compounds of formula (I), wherein
R1 is selected from the group consisting of: H, C1-3alkyl, alkoxy, hydroxy, SMe, NH2, NHMe, and cyclopropyl,
R2 is H or C1-3alkyl;
R3 is a phenyl or napthyl group which may be substituted with one to five substituents selected from the group consisting of: C1-6alkyl, halogen and alkoxy;
each R4 is independently selected from the group consisting of: C1-3alkyl, amide, and ester;
n is 0-2, m is 0-3;
and Ra and Rb are each independently H, or C1-3alkyl;
or a pharmaceutically acceptable salt thereof.

This invention also relates to compounds of formula (I), wherein
R1 is selected from the group consisting of: H, C1-3alkyl, hydroxy, NH2, and NHMe,
R2 is H or C1-3alkyl;
R3 is a phenyl or napthyl group which may be substituted with one to five substituents selected from the group consisting of: C1-6alkyl, halogen and alkoxy;
each R4 is independently selected from the group consisting of: C1-3alkyl, amide, and ester;
n is 0-2, m is 0-1;
Ra and Rb are each independently H, or C1-3alkyl;
or a pharmaceutically acceptable salt thereof.

This invention also relates to compounds of formula (I), wherein
R1 is selected from the group consisting of: H, C1-3alkyl, hydroxy, NH2, and NHMe,
R2 is H or C1-3alkyl;
R3 is a phenyl or napthyl group which may be substituted with one to five substituents selected from the group consisting of: C1-6alkyl, halogen and alkoxy;
each R4 is independently C1-3alkyl;
n is 0-2, m is 0-1; and
Ra and Rb are each independently H, or C1-3alkyl;
or a pharmaceutically acceptable salt thereof.

This invention also relates compounds of formula (I), wherein
R1 is selected from the group consisting of: H, C1-3alkyl and hydroxy;
R2 is H or C1-3alkyl;
R3 is a phenyl group which may be substituted with one to five substituents selected from the group consisting of: C1-6alkyl, halogen and alkoxy;
each R4 is independently C1-3alkyl;
n is 0-2, m is 0-1;
and Ra and Rb are each independently H, or C1-3alkyl;
or a pharmaceutically acceptable salt thereof.

This invention also relates compounds of formula (I), wherein
R1 is selected from the group consisting of: H, C1-3alkyl, alkoxy, —SMe, NH2, NHMe, cyclopropyl;
R2 is H or C1-3alkyl; and
R3 is a thienyl group which may be substituted with one to five substituents selected from the group consisting of: C1-6alkyl, halogen and alkoxy;
each R4 is independently selected from the group consisting of: C1-3alkyl, amide, and ester; and
n is 0-2, m is 0-1; and
Ra and Rb are each independently H, or C1-3alkyl;
or a pharmaceutically acceptable salt thereof.

This invention also relates compounds of formula (I), wherein
R1 is selected from the group consisting of: H, C1-3alkyl, alkoxy, SMe, NH2, NHMe, and cyclopropyl;
R2 is H or C1-3alkyl; and
R3 is a pyridinyl group which may be substituted with one to five substituents selected from the group consisting of: C1-6alkyl, halogen and alkoxy; each R4 is independently selected from the group consisting of: C1-3alkyl, amide, and ester; and
n is 0-2, m is 0-1; and
Ra and Rb are each independently H, or C1-3alkyl;
or a pharmaceutically acceptable salt thereof.

This invention also relates compounds of formula (I)(A), wherein

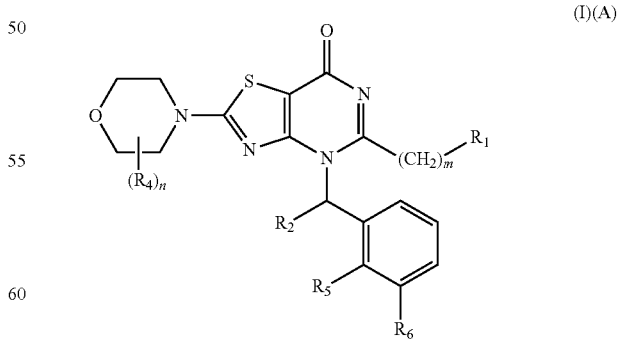

(I)(A)

wherein R5 and R6 are each independently selected from the group consisting of: C1-3alkyl, halogen, hydrogen, alkoxy, amino, cyano, hydroxy, amide and acyl, or a pharmaceutically acceptable salt thereof.

This invention also relates to the following compounds:
2-(4-morpholinyl)-4-(phenylmethyl)[1,3]thiazolo[4,5-d]pyrimidin-7(4H)-one,
4-[(2-methylphenyl)methyl]-2-(4-morpholinyl)[1,3]thiazolo[4,5-d]pyrimidin-7(4H)-one,
2-(cis-2,6-dimethyl-4-morpholinyl)-4-[(2-methylphenyl)methyl][1,3]thiazolo[4,5-d]pyrimidin-7(4H)-one,
4-[(2-fluorophenyl)methyl]-2-(4-morpholinyl)[1,3]thiazolo[4,5-d]pyrimidin-7(4H)-one,
4-[(2-chlorophenyl)methyl]-2-(4-morpholinyl)[1,3]thiazolo[4,5-d]pyrimidin-7(4H)-one,
2-(4-morpholinyl)-4-{[2(trifluoromethyl)phenyl]methyl}[1,3]thiazolo[4,5-d]pyrimidin-7(4H)-one,
4-[(2-bromophenyl)methyl]-2-(4-morpholinyl)[1,3]thiazolo[4,5-d]pyrimidin-7(4H)-one,
4-[(2-cyclopropylphenyl)methyl]-2-(4-morpholinyl)[1,3]thiazolo[4,5-d]pyrimidin-7(4H)-one,
4-[(2-ethylphenyl)methyl]-2-(4-morpholinyl)[1,3]thiazolo[4,5-d]pyrimidin-7(4H)-one,
4-[(3-methylphenyl)methyl]-2-(4-morpholinyl)[1,3]thiazolo[4,5-d]pyrimidin-7(4H)-one,
4-[(3-fluorophenyl)methyl]-2-(4-morpholinyl)[1,3]thiazolo[4,5-d]pyrimidin-7(4H)-one,
4-{[3-(methyloxy)phenyl]methyl}-2-(4-morpholinyl)[1,3]thiazolo[4,5-d]pyrimidin-7(4H)-one,
4-[(3-chlorophenyl)methyl]-2-(4-morpholinyl)[1,3]thiazolo[4,5-d]pyrimidin-7(4H)-one,
2-(4-morpholinyl)-4-{[3-(trifluoromethyl)phenyl]methyl}[1,3]thiazolo[4,5-d]pyrimidin-7(4H)-one,
2-(4-morpholinyl)-4-[(3-nitrophenyl)methyl][1,3]thiazolo[4,5-d]pyrimidin-7(4H)-one,
3-{[2-(4-morpholinyl)-7-oxo[1,3]thiazolo[4,5-d]pyrimidin-4(7H)-yl]methyl}benzonitrile,
2-(4-morpholinyl)-4-({3-[(trifluoromethyl)oxy]phenyl}methyl)[1,3]thiazolo[4,5-d]pyrimidin-7(4H)-one,
2-(4-morpholinyl)-4-{[3-(1H-pyrrol-1-yl)phenyl]methyl}[1,3]thiazolo[4,5-d]pyrimidin-7(4H)-one,
4-{[3-(3-methyl-1,2,4-oxadiazol-5-yl)phenyl]methyl}-2-(4-morpholinyl)[1,3]thiazolo[4,5-d]pyrimidin-7(4H)-one,
4-{[3-(5-methyl-1,2,4-oxadiazol-3-yl)phenyl]methyl}-2-(4-morpholinyl)[1,3]thiazolo[4,5-d]pyrimidin-7(4H)-one,
4-[(4-fluorophenyl)methyl]-2-(4-morpholinyl)[1,3]thiazolo[4,5-d]pyrimidin-7(4H)-one,
4-[(4-chlorophenyl)methyl]-2-(4-morpholinyl)[1,3]thiazolo[4,5-d]pyrimidin-7(4H)-one,
4-[(4-methylphenyl)methyl]-2-(4-morpholinyl)[1,3]thiazolo[4,5-d]pyrimidin-7(4H)-one,
4-{[2-(4-morpholinyl)-7-oxo[1,3]thiazolo[4,5-d]pyrimidin-4(7H)-yl]methyl)benzonitrile,
2-(4-morpholinyl)-4-({4-[(trifluoromethyl)oxy]phenyl}methyl)[1,3]thiazolo[4,5-d]pyrimidin-7(4H)-one,
methyl 3-{[2-(4-morpholinyl)-7-oxo[1,3]thiazolo[4,5-d]pyrimidin-4(7H)-yl]methyl}-2-thiophenecarboxylate,
4-[(2-bromo-3-thienyl)methyl]-2-(4-morpholinyl)[1,3]thiazolo[4,5-d]pyrimidin-7(4H)-one,
4-[(2-chloro-3-thienyl)methyl]-2-(4-morpholinyl)[1,3]thiazolo[4,5-d]pyrimidin-7(4H)-one,
2-(4-morpholinyl)-4-(3-thienylmethyl)[1,3]thiazolo[4,5-d]pyrimidin-7(4H)-one,
2-(4-morpholinyl)-4-(3-pyridinylmethyl)[1,3]thiazolo[4,5-d]pyrimidin-7(4H)-one,
4-[(2-fluoro-3-methylphenyl)methyl]-2-(4-morpholinyl)[1,3]thiazolo[4,5-d]pyrimidin-7(4H)-one,
4-[(3-chloro-2-fluorophenyl)methyl]-2-(4-morpholinyl)[1,3]thiazolo[4,5-d]pyrimidin-7(4H)-one,
4-[(2,3-dichlorophenyl)methyl]-2-(4-morpholinyl)[1,3]thiazolo[4,5-d]pyrimidin-7(4H)-one,
4-[(2,3-dichlorophenyl)methyl]-5-methyl-2-(4-morpholinyl)[1,3]thiazolo[4,5-d]pyrimidin-7(4H)-one,
rac-4-[(2,3-dichlorophenyl)methyl]-2-(2-methyl-4-morpholinyl)[1,3]thiazolo[4,5-d]pyrimidin-7(4H)-one,
(E2): 4-[(2,3-dichlorophenyl)methyl]-2-(2-methyl-4-morpholinyl)[1,3]thiazolo[4,5-d]pyrimidin-7(4H)-one,
(E1): 4-[(2,3-dichlorophenyl)methyl]-2-(2-methyl-4-morpholinyl)[1,3]thiazolo[4,5-d]pyrimidin-7(4H)-one,
4-[(2,3-dichlorophenyl)methyl]-2-(2,2-dimethyl-4-morpholinyl)[1,3]thiazolo[4,5-d]pyrimidin-7(4H)-one,
rac-4-[(2,3-dichlorophenyl)methyl]-2-[2-(hydroxymethyl)-4 morpholinyl][1,3]thiazolo[4,5-d]pyrimidin-7(4H)-one,
rac-ethyl 4-{4-[(2,3-dichlorophenyl)methyl]-7-oxo-4,7-dihydro[1,3]thiazolo[4,5-d]pyrimidin-2-yl}-2-morpholinecarboxylate,
4-[(3-fluoro-2-methylphenyl)methyl]-2-(4-morpholinyl)[1,3]thiazolo[4,5-d]pyrimidin-7(4H)-one,
4-{[2-methyl-3-(trifluoromethyl)phenyl]methyl}-2-(4-morpholinyl)[1,3]thiazolo[4,5-d]pyrimidin-7(4H)-one,
5-methyl-4-{[2-methyl-3-(trifluoromethyl)phenyl]methyl}-2-(4-morpholinyl)[1,3]thiazolo[4,5-d]pyrimidin-7(4H)-one,
4-[(3-chloro-2-methylphenyl)methyl]-2-(4-morpholinyl)[1,3]thiazolo[4,5-d]pyrimidin-7(4H)-one,
4-[(3-chloro-2-methylphenyl)methyl]-5-methyl-2-(4-morpholinyl)[1,3]thiazolo[4,5-d]pyrimidin-7(4H)-one,
4-[(4-fluoro-2-methylphenyl)methyl]-2-(4-morpholinyl)[1,3]thiazolo[4,5-d]pyrimidin-7(4H)-one,
4-[(5-fluoro-2-methylphenyl)methyl]-2-(4-morpholinyl)[1,3]thiazol o[4,5-d]pyrimidin-7(4H)-one,
4-[(2-fluoro-5-methylphenyl)methyl]-2-(4-morpholinyl)[1,3]thiazolo[4,5-d]pyrimidin-7(4H)-one,
4-[(2,5-dimethylphenyl)methyl]-2-(4-morpholinyl)[1,3]thiazolo[4,5-d]pyrimidin-7(4H)-one,
4-{[2-methyl-5-(trifluoromethyl)phenyl]methyl}-2-(4-morpholinyl)[1,3]thiazolo[4,5-d]pyrimidin-7(4H)-one,
4-{[2-chloro-5-(trifluoromethyl)phenyl]methyl}-2-(4-morpholinyl)[1,3]thiazolo[4,5-d]pyrimidin-7(4H)-one,
4-[(2-chloro-5-fluorophenyl)methyl]-2-(4-morpholinyl)[1,3]thiazolo[4,5-d]pyrimidin-7(4H)-one,
4-{[2-fluoro-5-(trifluoromethyl)phenyl]methyl}-2-(4-morpholinyl)[1,3]thiazolo[4,5-d]pyrimidin-7(4H)-one,
4-[(5-chloro-2-fluorophenyl)methyl]-2-(4-morpholinyl)[1,3]thiazolo[4,5-d]pyrimidin-7(4H)-one,
4-[(2,5-dichlorophenyl)methyl]-2-(4-morpholinyl)[1,3]thiazolo[4,5-d]pyrimidin-7(4H)-one,
4-[(3,4-dichlorophenyl)methyl]-2-(4-morpholinyl)[1,3]thiazolo[4,5-d]pyrimidin-7(4H)-one,
4-[(3,4-dichlorophenyl)methyl]-5-methyl-2-(4-morpholinyl)[1,3]thiazolo[4,5-d]pyrimidin-7(4H)-one,
4-[(3-chloro-4-fluorophenyl)methyl]-2-(4-morpholinyl)[1,3]thiazolo[4,5-d]pyrimidin-7(4H)-one,
2-(4-morpholinyl)-4-[(2,3,4-trifluorophenyl)methyl][1,3]thiazolo[4,5-d]pyrimidin-7(4H)-one,
4-[(3-chloro-2,4-difluorophenyl)methyl]-2-(4-morpholinyl)[1,3]thiazolo[4,5-d]pyrimidin-7(4H)-one,
4-{[2,4-difluoro-3-(methyloxy)phenyl]methyl}-2-(4-morpholinyl)[1,3]thiazolo[4,5-d]pyrimidin-7(4H)-one,
2-(4-morpholinyl)-4-[(2,4,6-trifluorophenyl)methyl][1,3]thiazolo[4,5-d]pyrimidin-7(4H)-one,
2-(4-morpholinyl)-4-(2-naphthalenylmethyl)[1,3]thiazolo[4,5-d]pyrimidin-7(4H)-one,
5-methyl-2-(4-morpholinyl)-4-(2-naphthalenylmethyl)[1,3]thiazolo[4,5-d]pyrimidin-7(4H)-one,
4-[(2-methyl-6-quinolinyl)methyl]-2-(4-morpholinyl)[1,3]thiazolo[4,5-d]pyrimidin-7(4H)-one, 4-[(4-bromo-1-naphthalenyl)methyl]-2-(4-morpholinyl)[1,3]thiazolo[4,5-d]pyrimidin-7(4H)-one,
2-(4-morpholinyl)-4-(1-naphthalenylmethyl)[1,3]thiazolo[4,5-d]pyrimidin-7(4H)-one,
5-methyl-2-(4-morpholinyl)-4-(1-naphthalenylmethyl)[1,3]thiazolo[4,5-d]pyrimidin-7(4H)-one,
4-(1-benzothien-7-ylmethyl)-2-(4-morpholinyl)[1,3]thiazolo[4,5-d]pyrimidin-7(4H)-one,
4-[(3-chloro-2-methylphenyl)methyl]-5-methyl-2-(4-morpholinyl) [1,3]thiazolo[4,5-d]pyrimidin-7(4H)-one,
4-[(3,4-dichlorophenyl)methyl]-5-methyl-2-(4-morpholinyl) [1,3]thiazolo[4,5-d]pyrimidin-7(4H)-one,
2-(2,6-dimethyl-4-morpholinyl)-4-[(2-methylphenyl)methyl][1,3]thiazolo[4,5-d]pyrimidin-7(4H)-one,
2-(2,6-dimethyl-4-morpholinyl)-4-[(2-methylphenyl)methyl][1,3]thiazolo[4,5-d]pyrimidin-7(4H)-one,
2-(2-methyl-4-morpholinyl)-4-{[2-methyl-3-(trifluoromethyl)phenyl]methyl}[1,3]thiazolo[4,5-d]pyrimidin-7(4H)-one,
4-[(2,3-dichlorophenyl)methyl]-2-(3-methyl-4-morpholinyl)[1,3]thiazolo[4,5-d]pyrimidin-7(4H)-one,
4-[(2,3-dichlorophenyl)methyl]-2-[2-(hydroxymethyl)-4-morpholinyl][1,3]thiazolo[4,5-d]pyrimidin-7(4H)-one,
ethyl 4-{4-[(2,3-dichlorophenyl)methyl]-7-oxo-4,7-dihydro[1,3]thiazolo[4,5-d]pyrimidin-2-yl}-2-morpholinecarboxylate,
5-cyclopropyl-4-{[2-methyl-3-(trifluoromethyl)phenyl]methyl}-2-(4-morpholinyl)[1,3]thiazolo[4,5-d]pyrimidin-7(4H)-one,
5-cyclopropyl-4-{[2-methyl-3-(trifluoromethyl)phenyl]methyl}-2-(4-morpholinyl)[1,3]thiazolo[4,5-d]pyrimidin-7(4H)-one,
4-[(3-chloro-2-methylphenyl)methyl]-5-cyclobutyl-2-(4-morpholinyl)[1,3]thiazolo[4,5-d]pyrimidin-7(4H)-one,
5-[2-(methylthio)ethyl]-4-{[2-methyl-3-(trifluoromethyl)phenyl]methyl}-2-(4-morpholinyl)[1,3]thiazolo[4,5-d]pyrimidin-7(4H)-one,
4-[(3-chloro-2-methylphenyl)methyl]-5-[2-(methylthio)ethyl]-2-(4-morpholinyl)[1,3]thiazolo[4,5-d]pyrimidin-7(4H)-one,
4-[(3-chloro-2-methylphenyl)methyl]-5-ethyl-2-(4-morpholinyl)[1,3]thiazolo[4,5-d]pyrimidin-7(4H)-one,
5-ethyl-4-{[2-methyl-3-(trifluoromethyl)phenyl]methyl}-2-(4-morpholinyl)[1,3]thiazolo[4,5-d]pyrimidin-7(4H)-one,
4-{[2-methyl-3-(trifluoromethyl)phenyl]methyl}-2-(4-morpholinyl)-5-(phenylmethyl)[1,3]thiazolo[4,5-d]pyrimidin-7(4H)-one,
4-[(3-chloro-2-methylphenyl)methyl]-2-(4-morpholinyl)-5-(phenylmethyl)[1,3]thiazolo[4,5-d]pyrimidin-7(4H)-one,
4-{[2-methyl-3-(trifluoromethyl)phenyl]methyl}-2-(4-morpholinyl)-5-phenyl[1,3]thiazolo[4,5-d]pyrimidin-7(4H)-one,
4-[(3-chloro-2-methylphenyl)methyl]-5-[(1S)-1-hydroxyethyl]-2-(4-morpholinyl)[1,3]thiazolo[4,5-d]pyrimidin-7(4H)-one,
4-[(3-chloro-2-methylphenyl)methyl]-5-[2-(methyloxy)ethyl]-2-(4-morpholinyl)[1,3]thiazolo[4,5-d]pyrimidin-7(4H)-one,
4-[(3-chloro-2-methylphenyl)methyl]-2-(4-morpholinyl)-5-(tetrahydro-3-furanyl)[1,3]thiazolo[4,5-d]pyrimidin-7(4H)-one,
4-[(3-chloro-2-methylphenyl)methyl]-2-(4-morpholinyl)-5-(tetrahydro-2-furanyl)[1,3]thiazolo[4,5-d]pyrimidin-7(4H)-one,
4-[(3-chloro-2-methylphenyl)methyl]-5-(hydroxymethyl)-2-(4-morpholinyl)[1,3]thiazolo[4,5-d]pyrimidin-7(4H)-one,
5-methyl-2-(4-morpholinyl)-4-(1-phenylethyl)[1,3]thiazolo[4,5-d]pyrimidin-7(4H)-one,
5-(1-methylethyl)-2-(2-methyl-4-morpholinyl)-4-{[2-methyl-3-(trifluoromethyl)phenyl]methyl}[1,3]thiazolo[4,5-d]pyrimidin-7(4H)-one,
5-(hydroxymethyl)-4-{[2-methyl-3-(trifluoromethyl)phenyl]methyl}-2-(4-morpholinyl)[1,3]thiazolo[4,5-d]pyrimidin-7(4H)-one,
5-(1-methylethyl)-4-{[2-methyl-3-(trifluoromethyl)phenyl]methyl}-2-(4-morpholinyl)[1,3]thiazolo[4,5-d]pyrimidin-7(4H)-one,
5-(fluoromethyl)-4-{[2-methyl-3-(trifluoromethyl)phenyl]methyl}-2-(4-morpholinyl) [1,3]thiazolo[4,5-d]pyrimidin-7(4H)-one,
4-[(3-chloro-2-methylphenyl)methyl]-5-(fluoromethyl)-2-(4-morpholinyl)[1,3]thiazolo[4,5-d]pyrimidin-7(4H)-one,
4-[(3,4-dichlorophenyl)methyl]-5-methyl-2-(2-methyl-4-morpholinyl) [1,3]thiazolo[4,5-d]pyrimidin-7(4H)-one,
5-methyl-2-(2-methyl-4-morpholinyl)-4-{[2-methyl-3-(trifluoromethyl)phenyl]methyl}[1,3]thiazolo[4,5-d]pyrimidin-7(4H)-one,
4-[(3-chloro-2-methylphenyl)methyl]-5-methyl-2-(2-methyl-4-morpholinyl)[1,3]thiazolo[4,5-d]pyrimidin-7(4H)-one,
4-[2-(2-methylphenyl)ethyl]-2-(4-morpholinyl)[1,3]thiazolo[4,5-d]pyrimidin-7(4H)-one,
4-[(3-chloro-2-methylphenyl)methyl]-5-[(methyloxy)methyl]-2-(4-morpholinyl)[1,3]thiazolo[4,5-d]pyrimidin-7(4H)-one,
4-[(3-chloro-2-methylphenyl)methyl]-2-(4-morpholinyl)-5-[(phenyloxy)methyl][1,3]thiazolo[4,5-d]pyrimidin-7(4H)-one,
[4-[(3-chloro-2-methylphenyl)methyl]-2-(4-morpholinyl)-7-oxo-4,7-dihydro[1,3]thiazolo[4,5-d]pyrimidin-5-yl] methyl acetate,
4-{[2-methyl-3-(trifluoromethyl)phenyl]methyl}-2-(4-morpholinyl)-5-[(phenyloxy)methyl][1,3]thiazolo[4,5-d]pyrimidin-7(4H)-one,
(1S)-1-[4-[(3-chloro-2-methylphenyl)methyl]-2-(4-morpholinyl)-7-oxo-4,7-dihydro[1,3]thiazolo[4,5-d]pyrimidin-5-yl]ethyl acetate,
4-[(3-chloro-2-methylphenyl)methyl]-2-(4-morpholinyl)-5-[(phenylthio)methyl][1,3]thiazolo[4,5-d]pyrimidin-7(4H)-one,
4-[(3-chloro-2-methylphenyl)methyl]-2-(4-morpholinyl)-5-(tetrahydro-2H-pyran-2-yl)[1,3]thiazolo[4,5-d]pyrimidin-7(4H)-one,
4-[(3-chloro-2-methylphenyl)methyl]-5-[(methylthio)methyl]-2-(4-morpholinyl)[1,3]thiazolo[4,5-d]pyrimidin-7(4H)-one,
4-[(3-chloro-2-methylphenyl)methyl]-2-(4-morpholinyl)-5-{[(phenylmethyl)oxy]methyl}[1,3]thiazolo[4,5-d]pyrimidin-7(4H)-one,
4-[(3-chloro-2-methylphenyl)methyl]-2-(4-morpholinyl)-5-[(phenylsulfonyl)methyl][1,3]thiazolo[4,5-d]pyrimidin-7(4H)-one,
4-[(3-chloro-2-methylphenyl)methyl]-2-(4-morpholinyl)[1,3]thiazolo[4,5-d]pyrimidine-5,7(4H,6H)-dione,
4-[(3-chloro-2-methylphenyl)methyl]-2-(4-morpholinyl)-5-thioxo-5,6-dihydro[1,3]thiazolo[4,5-d]pyrimidin-7(4H)-one,
4-[(3-chloro-2-methylphenyl)methyl]-5-(methylthio)-2-(4-morpholinyl)[1,3]thiazolo[4,5-d]pyrimidin-7(4H)-one,
5-amino-4-[(3-chloro-2-methylphenyl)methyl]-2-(4-morpholinyl) [1,3]thiazolo[4,5-d]pyrimidin-7(4H)-one, {[4-[(3-chloro-2-methylphenyl)methyl]-2-(4-morpholinyl)-7-oxo-4,7-dihydro[1,3]thiazolo[4,5-d]pyrimidin-5-yl]thio}acetic acid, 5-(aminomethyl)-4-[(3-chloro-2-methylphenyl)methyl]-2-(4-morpholinyl)[1,3]thiazolo[4,5-d]pyrimidin-7(4H)-one, 4-[(3-chloro-2-methylphenyl)methyl]-5-[(dimethylamino)methyl]-2-(4-morpholinyl)[1,3]thiazolo[4,5-d]pyrimidin-7(4H)-one, 5-(hydroxymethyl)-4-{[2-methyl-3-(trifluoromethyl)phenyl]methyl}-2-(4-morpholinyl)[1,3]thiazolo[4,5-d]pyrimidin-7(4H)-one, 5-(aminomethyl)-4-{[2-methyl-3-(trifluoromethyl)phenyl]methyl}-2-(4-morpholinyl)[1,3]thiazolo[4,5-d]pyrimidin-7(4H)-one, 4-[(3-chloro-2-methylphenyl)methyl]-2-(4-morpholinyl)-5-(1-pyrrolidinylmethyl) [1,3]thiazolo[4,5-d]pyrimidin-7(4H)-one, 4-[(3-chloro-2-methylphenyl)methyl]-5-(methyloxy)-2-(4-morpholinyl)[1,3]thiazolo[4,5-d]pyrimidin-7(4H)-one, 5-ethyl-4-{[2-methyl-3-(trifluoromethyl)phenyl]methyl}-2-(4-morpholinyl)[1,3]thiazolo[4,5-d]pyrimidin-7(4H-one-$d_2$, methyl 2-chloro-6-{[5-methyl-2-(4-morpholinyl)-7-oxo[1,3]thiazolo[4,5-d]pyrimidin-4(7H-yl]methyl}benzoate, 5-(1-aminoethyl)-4-[(3-chloro-2-methylphenyl)methyl]-2-(4-morpholinyl)[1,3]thiazolo[4,5-d]pyrimidin-7(4H)-one, and diethyl {1-[4-[(3-chloro-2-methylphenyl)methyl]-2-(4-morpholinyl)-7-oxo-4,7-dihydro[1,3]thiazolo[4,5-d]pyrimidin-5-yl]ethyl}phosphonate, and pharmaceutically acceptable salt thereofs.

This invention also relates to the following compounds:
5-methyl-4-{[2-methyl-3-(trifluoromethyl)phenyl]methyl}-2-(4-morpholinyl)[1,3]thiazolo[4,5-d]pyrimidin-7(4H)-one, 4-[(3-chloro-2-methylphenyl)methyl]-5-ethyl-2-(4-morpholinyl)[1,3]thiazolo[4,5-d]pyrimidin-7(4H)-one, and pharmaceutically acceptable salts thereof.

DEFINITIONS

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. An aryl group can be substituted or unsubstituted with 1-5 substituents, preferably 1-3. Suitable substituents, unless otherwise defined, are described below in the definition of "substituted".

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. A heteroaryl group can be substituted or unsubstituted. Suitable substituents, unless otherwise defined, are defined below in the definition of "substituted".

By the term "alkoxy" as used herein is meant —O(alkyl) including —OCH$_3$, —OCH$_2$CH$_3$ and —OC(CH$_3$)$_3$ where alkyl is as described herein.

By the term "alkylthio" as used herein is meant —S(alkyl) including —SCH$_3$, —SCH$_2$CH$_3$ where alkyl is as described herein.

The term "cycloalkyl" as used herein unless otherwise defined, is meant a nonaromatic, unsaturated or saturated, cyclic or polycyclic C$_3$-C$_{12}$. A cycloalkyl group can be substituted or unsubstituted. Suitable substituents, unless otherwise defined, are described below in the definition of "substituted".

Examples of cycloalkyl and substituted cycloalkyl substituents as used herein include: cyclohexyl, aminocyclohexyl, cyclobutyl, aminocyclobutyl, 4-hydroxy-cyclohexyl, 2-ethylcyclohexyl, propyl4-methoxycyclohexyl, 4-methoxycyclohexyl, 4-carboxycyclohexyl, cyclopropyl, aminocyclopentyl, and cyclopentyl.

By the term "heterocycloalkyl" as used herein is meant a non-aromatic, unsaturated or saturated, monocyclic or polycyclic, heterocyclic ring containing 4-6 member atoms which include at least one carbon and at least one heteroatom. Exemplary monocyclic heterocyclic rings include: piperidine, piperazine, pyrrolidine, and morpholine. Exemplary polycyclic heterocyclic rings include quinuclidine. A heterocycloalkyl group can be substituted or unsubstituted. Suitable substituents, unless otherwise defined, are described below in the definition of "substituted".

By the term "substituted" as used herein, unless otherwise defined, is meant that the subject chemical moiety has one to five substituents, suitably from one to three, selected from the group consisting of: hydrogen, halogen, C$_1$-C$_6$alkyl, amino, trifluoromethyl, carboxylic acid, C$_3$-C$_7$cycloalkyl, heterocycloalkyl, cyano, hydroxy, alkoxy, alkylthio, acetyl, nitro, oxo, and heteroaryl, wherein the heteroaryl are optionally substituted with one to three groups independently selected from halogen and C$_1$-3alkyl.

By the term "heteroatom" as used herein is meant oxygen, nitrogen or sulfur.

By the term "halogen" as used herein is meant a substituent selected from bromide, iodide, chloride and fluoride.

By the term "arylalkyl" as used herein is meant —C1-3alkyl(aryl) wherein the C1-3alkyl and the aryl can be substituted or unsubstituted. Suitable substituents, unless otherwise defined, are described below in the definition of "substituted".

By the term "alkyl" and derivatives thereof and in all carbon chains as used herein, including alkyl chains defined by the term "—(CH$_2$)$_n$", "—(CH$_2$)$_m$" and the like, is meant a linear or branched, substituted or unsubstituted, saturated or unsaturated hydrocarbon chain, and unless otherwise defined, the carbon chain will contain from 1 to 12 carbon atoms; An alkyl can be substituted with one to four substituents selected from the group consisting of: halogen, trifluoromethyl, alkylcarboxy, amino, substituted amino, cyano, hydroxy, alkoxy, alkylthio, aryloxy, acyloxy, acyl, acylamino, phosphonate, phosphonic acid, ester, carboxylic acid and nitro.

By the term "treating" and derivatives thereof as used herein, is meant prophylatic and therapeutic therapy. Prophylatic therapy is meant the institution of measures to protect a person from a disease to which he or she has been, or may be, exposed. Also called preventive treatment.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

In formulas where a "dotted" bond is drawn between two atoms, it is meant that such bond can be either single or double bond. A ring system containing such bonds can be aromatic or non-aromatic.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by Formula (I) above as well as any wholly or partially equilibrated mixtures thereof. The present invention also covers the individual isomers of the compounds represented by the formulas above as mixtures with isomers thereof in which one or more chiral centers are inverted. The present invention also includes isotopomers of the compounds of Formula (I). Examples of such isotopomers include but not limited to compounds with one of more deuterium atoms.

Compounds of Formula (I) are included in the pharmaceutical compositions of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

Compounds according to Formula (I) are suitable for the modulation, notably the inhibition of the activity of phosphatoinositides 3-kinases (PI3K), suitably phosphatoinositides 3-kinase (PI3K). Therefore the compounds of the present invention are also useful for the treatment of disorders which are mediated by PI3Ks. Said treatment involves the modulation—notably the inhibition or the down regulation—of the phosphatoinositides 3-kinases.

Because the pharmaceutically active compounds of the present invention are active as PI3 kinase inhibitors, particularly the compounds that inhibit PI3KRβ, either selectively or in conjunction with one or more of PI3KS, PI3Kα, and/or PI3Kγ, they exhibit therapeutic utility in treating cancer.

Suitably, the invention relates to a method of treating cancer in a mammal, including a human, wherein the cancer is selected from: brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Suitably, the invention relates to a method of treating cancer in a mammal, including a human, wherein the cancer is selected from: Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, Acute megakaryocytic leukemia, promyelocytic leukemia and Erythroleukemia.

Suitably, the invention relates to a method of treating cancer in a mammal, including a human, wherein the cancer is selected from: malignant lymphoma, hodgkins lymphoma, non-hodgkins lymphoma, lymphoblastic T cell lymphoma, Burkitt's lymphoma and follicular lymphoma.

Suitably, the invention relates to a method of treating cancer in a mammal, including a human, wherein the cancer is selected from: neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β, 13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad, Sci. USA, 77:1561-1565 (1980);

Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-1-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H, 12H)-dione hydrochloride, is commercially available as the injectable solution CAMPTOSAR®.

Irinotecan is a derivative of camptothecin which binds, along with its active metabolite SN-38, to the topoisomerase I—DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I—DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

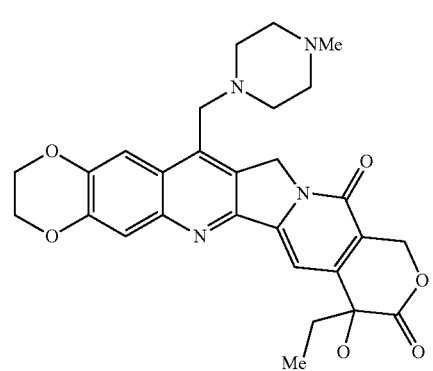

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChem. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone $C_{225}$ EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as PI3 kinase inhibitors, particularly the compounds that modulate/inhibit PI3Kβ, either selectively or in conjunction with one or more of PI3Kα, PI3Kγ, and/or PI3Kδ, they exhibit therapeutic utility in treating a disease state selected from: autoimmune disorders, inflammatory diseases, cardiovascular diseases, neurodegenerative diseases, allergy, cancer, asthma, pancreatitis, multiorgan failure, kidney diseases, platelet aggregation, sperm motility, transplantation rejection, graft rejection and lung injuries.

When a compound of Formula (I) is administered for the treatment of a disease state selected from: autoimmune disorders, inflammatory diseases, cardiovascular diseases, neurodegenerative diseases, cancer, allergy, asthma, pancreatitis, multiorgan failure, kidney diseases, platelet aggregation, sperm motility, transplantation rejection, graft rejection or lung injuries, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of autoimmune disorders, inflammatory diseases, cardiovascular diseases, cancer, neurodegenerative diseases, allergy, asthma, pancreatitis, multiorgan failure, kidney diseases, platelet aggregation, sperm motility, transplantation rejection, graft rejection and/or lung injuries.

Biological Assays

Compounds of the present invention were tested according to the following assays and found as inhibitors of PI3 kinases, particularly PI3Kβ. The activities (IC$_{50}$) of exemplified compounds range from about 1 nM to about 10 μM against PI3Kβ. The majority of the compounds were under 500 nM; the most active compounds were under 10 nM. The IC$_{50}$ value can be converted and presented as pIC$_{50}$ value.

The compound of Example 1 was tested generally according to the assays described herein and in at least one experimental run exhibited an IC50 value equal to 0.32 μM against PI3Kβ.

The compound of Example 3 was tested generally according to the assays described herein and in at least one experimental run exhibited an IC50 value equal to 0.40 μM against PI3Kβ.

The compound of Example 20 was tested generally according to the assays described herein and in at least one experimental run exhibited an IC50 value equal to 0.008 μM against PI3Kδ.

The compound of Example 59 was tested generally according to the assays described herein and in at least one experimental run exhibited an IC50 value of 0.5 nM against PI3Kβ.

The compound of Example 75 was tested generally according to the assays described herein and in at least one experimental run exhibited a pIC50 value of 9.8 against PI3Kδ.

The compound of Example 79 was tested generally according to the assays described herein and in at least one experimental run exhibited a pIC50 value of 7.3 against PI3Kδ.

The compound of Example 83 was tested generally according to the assays described herein and in at least one experimental run exhibited a pIC50 value of 8.9 against PI3Kδ.

The compound of Example 84 was tested generally according to the assays described herein and in at least one experimental run exhibited a pIC50 value of 9.9 against PI3Kδ.

The compound of Example 111 was tested generally according to the assays described herein and in at least one experimental run exhibited a pIC50 value of 8.6 against PI3Kδ.

HTRF In vitro Profiling Assays for PI3K Inhibition

The PI3-Kinase profiling assays were developed to measure the compound-dependent inhibition of the alpha, beta, delta, and gamma isoforms of PI3K in an in vitro catalytic assay. This assay was developed and optimized from a kit produced by Upstate (Millipore catalog #33-017). Briefly, this procedure utilizes a pre-formed HTRF (Homogeneous Time-Resolved Fluorescence energy transfer) complex between four binding partners: 1) biotinylated PIP3, 2) GST tagged pleckstrin homology (PH) domain, 3) Europium labeled anti-GST monoclonal antibody, and 4) Streptavidin-Allophycocyanin (APC). The native PIP3 produced by PI 3-Kinase activity displaces biotin-PIP3 from the PH domain, resulting in the dissociation of the HTRF complex and a decrease in the fluorescence signal. The format of this assay is the same for all 4 isoforms of PI3K; the differences lie in the concentration of enzyme used to achieve the most robust signal. The alpha and delta assays are run at 400 µM enzyme; the beta assay is at 200 µM enzyme and the gamma assay is run at 1 nM enzyme. In addition, the alpha, beta and delta assays are run with 150 mM NaCl while the gamma assay is run in the absence of NaCl. The ATP concentration is 100 uM in the alpha, beta, and delta assays and 15 uM ATP in the gamma assay. All reactions are run at 10 uM PIP2

Assay Protocol

Compounds are serially diluted (3-fold in 100% DMSO) across a 384-well polypropylene mother plate from column I to column 12 and column 13 to column 24, to yield 11 concentrations for each test compound. Columns 6 and 18 contain only DMSO. Once titrations are made, 0.05 µL is transferred to a 384-well low-volume assay plate (Greiner 784076). This assay plate contains three pharmacological controls (known PI3K inhibitors) and 3 assay controls: (1) Enzyme without inhibitor; (2) Buffer minus enzyme, and (3) Buffer minus enzyme plus native PIP3. DMSO is stamped into all wells of columns 6 and 18. PIP3 is added at 40 µM in 1× Reaction buffer (1 µL of 200 µM PIP3) to alternating rows of column 18 (wells 18 B, D, F, H, J, L, N, P). The no-enzyme control reactions are run in wells 18 A, C, E, G, I, K, M, O (0.1 µL of 100% DMSO).

The PI3-Kinase profiling assay was optimized using the HTRF kit provided by Upstate (Millipore). The assay kit contains seven reagents: 1) 4× Reaction Buffer; 2) native PIP2 (substrate); 3) Stop A (EDTA); 4) Stop B (Biotin-PIP3); 5) Detection Mix A (Streptavidin-APC); 6) Detection Mix B (Eu-labeled Anti-GST plus GST-tagged PH-domain); 7) Detection Mix C (KF). In addition, the following items were obtained or purchased: PI3Kinase (prepared by GSK BR&AD), dithiothreitol (Sigma, D-5545), Adenosine-5'-triphosphate (ATP, Teknova cat. #A0220), native PIP3 (1,2-dioctanoyl-sn-glycero-3-[phosphoinositil-3,4,5-triphosphate]tetraammonium salt (Avanti polar lipids, 850186P), DMSO (Sigma, 472301).

PI3Kinase Reaction Buffer is prepared by diluting the stock 1:4 with de-ionized water. Freshly prepared DTT is added at a final concentration of 5 mM on the day of use. Enzyme addition and compound pre-incubation are initiated by the addition of 2.5 µL of PI3K (at twice its final concentration) in 1× reaction buffer to all wells using a Multidrop Combi. Plates are incubated at room temperature for 15 minutes. Reactions are initiated by addition of 2.5 µL of 2× substrate solution (PIP2 and ATP in 1× reaction buffer) using a Multidrop Combi. Plates are incubated at room temperature for one hour. Reactions are quenched by the addition of 2.5 µL of stop solution (Stop A and Stop B pre-mixed at a ratio of 5:1, respectively) to all wells using the Multidrop Combi. The quenched reactions are then processed to detect product formation by adding 2.5 µL of Detection Solution to all wells using the Mulitdrop Combi (Detection mix C, Detection mix A, and Detection mix B combined together in an 18:1:1 ratio, i.e.: for a 6000 µL total volume, mix 5400 µL Detection mix C, 300 µL Detection mix A, and 300 L Detection mix B. Note: this solution should be prepared 2 hours prior to use). Following a one hour incubation in the dark, the HTRF signal is measured on the Envision plate reader set for 330 nm excitation and dual emission detection at 620 nm (Eu) and 665 nm (APC).

Data Analysis

The loss of the HTRF signal is due to the displacement of biotinylated-PIP3 from the PH domain by the PI3K-dependent conversion of PIP2 to PIP3. This loss of signal is non-linear with respect to both increasing product and time. This non-linear detection will impact accuracy of $IC_{50}$ calculations; therefore, there is a need for a correction factor to obtain more accurate $IC_{50}$ values This correction is derived from the assay standards in the wells of column 6 and 18 of the assay plate. All data were calculated using the ratio of acceptor (APC) to donor (Europium) fluorescence in each well of the assay plate. The percent inhibition for each compound concentration was calculated as follows: % inhibition=100* (fluorescence ratio−CtrlB)/(CtrlA−CtrlB) where CtrlA=(−) PI3Kinase reaction and CrtlB=PI3Kinase+DMSO. An $IC_{50}$ was then calculated fitting the % inhibition data to the equation: % inhibition=min+(max−min)/(1+([inhibitor]/$IC_{50}$)^n) where min is the % inhibition with no inhibitor (typically 0%), max is the signal in the (−) Enzyme control, and n is the Hill slope (typically 1). Finally, the $IC_{50}$ was converted to $pIC_{50}$ ($pIC_{50}$=−log($IC_{50}$)), and the $pIC_{50}$ value was corrected by using plate controls and the equation below:

$pIC_{50}$ (corrected)=$pIC_{50}$ (observed)+log 10((CtrlA−CtrlB)/(CtrlB−CtrlC)), where CtrlA and CtrlB are as defined above and CrtlC=10 µM PI(3,4,5)P3, 100% displacement of biotinylated PI(3,4,5)P3.

Celluar Assays:

DAY 1

Plate cells before noon
- 4000 cells/well in clear flat-bottomed 384-well plates (f.v. 48 ul)
- Column 24 receives media only
- Place in 37 degC incubator overnight Compound plate
- Prepare in polypropylene round-bottomed 384-well plates, 20-pt titrations of each (2× serial dilution), DMSO in column 22 (0.15% f.c. on cells)
- 20 ul in first well, 10 ul DMSO in the rest; take 10 ul from first well and mix in next, continue across plate (excluding last column); seal with foil lid and place at 4 degC

DAY 2

Take out Lysis buffer inhibitors (4 degC/−20 degC) and compound plates (4 degC), thaw on bench top; make 1× Tris wash buffer (WB) to fill reservoir on plate washer and top off bench supply (use MiliQ), turn on centrifuge to allow it to cool Block MSD plates
  Make 14 ml 3% blocking solution/plate (420 mg blocker A in 14 ml WB), add 35 ul/well and incubate at RT for at least 1 hr
Add compound (while blocking)
  Add 105 ul growth media (RPMI w/Q, 10% FBS) per well (682× dil of compound) to each compound plate
  Add 2 ul compound dilution into each well on duplicate plates
  Place in 37 degC incubator for 30 min
Make lysates
  Prepare MSD Lysis buffer; for 10 ml add 200 ul protease inhibitor solution, and 100 ul each of Phosphatase inhibitors I & II (Keep on ice until ready for use)
  Remove plates post-incubation, aspirate media with plate washer, wash 1× with cold PBS, and add 25 ul MSD Lysis buffer per well; incubate on shaker at 4 degC for ≧30 min
AKT duplex assay
  Wash plates (4× with 100 ul/well WB in plate washer); tap plates on paper towel to blot
  Add 20 ul of lysates/well, incubate on shaker at RT for 1 hr
  During incubation prepare detection Ab (7.8 ml/plate; 5.2 ml WB and 2.6 ml blocking solution w/Ab at 3.35 nM); repeat wash step as above
  Add 20 ul of Ab/well, incubate on shaker at RT for 1 hr; repeat wash step as above
  Add 35 ul/well 1× Read Buffer (dilute 4× stock in ddH$_2$O, 20 ml/plate), read immediately
Analysis
  Observe all the data points at each compound concentration.
  The data point from highest inhibitor concentration must be equal or greater than 70% of DMSO control.
  IC50 for duplicate runs must be within 3-fold of each other
  Y min must be greater than zero; if both mins are red flagged (>35) then compound is listed as inactive (IC50=>highest dose). If only one min is red flagged, but still≦50 then call IC50 as listed.
  Any data points equal or greater than 30% off the curve will not be considered.
Additional References:
  The compounds of the present invention can also be tested to determine their inhibitory activity at PI3Kα, PI3Kδ, PI3Kδ and PI3Kγ according to international patent publication No. WO2009/039140.

The pharmaceutically active compounds within the scope of this invention are useful as PI3Kinase inhibitors in mammals, particularly humans, in need thereof.

The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or prodrug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

Experimental Details

The derivatives described herein were or can be prepared according to the following schemes:

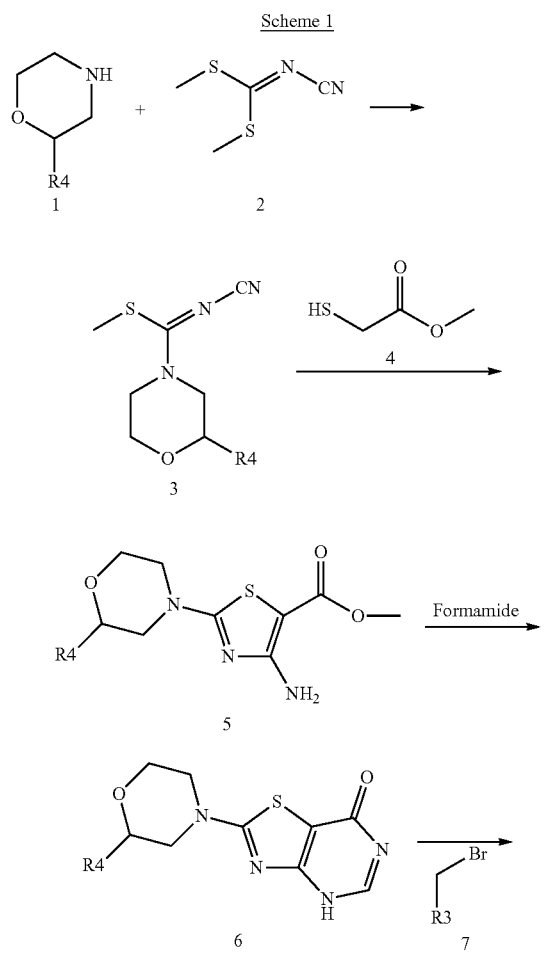

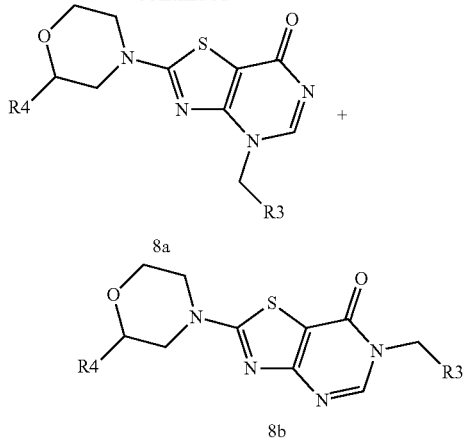

Morpholine, 2-substituted or 2,6-disubstituted morpholines 1 can react with dimethyl cyanodithioimidocarbonate (2) to give methyl N-cyano-carbimidothioates 3, which cyclize with methyl mercaptoacetate (4) to form methyl 4-amino-1,3-thiazole-5-carboxylates 5. Thermally heating 5 in formamide at 150° C. for 1-3 day depending on the scale of the reaction, or under microwave irradiation at 200° C. for 30 min to 1 hr, generates [1,3]thiazolo[4,5-d]pyrimidin-7(4H)-ones 6. Deprotonation of 6 with either lithium bis(trimethylsilyl)amide (LiHMDS) or isopropylmagnesium chloride (iPrMgCl), or the complex of LiHMDS and (iPrMgCl) in anhydrous tetrahydrofuran (THF) at 0° C., followed by N-alkylation with substituted benzyl bromide or heteroaryl bromide 7, affords either the desired product 8a, or a mixture of 8a and 8b, which are separable either by flash column chromatography on silica gel or by reverse phase HPLC.

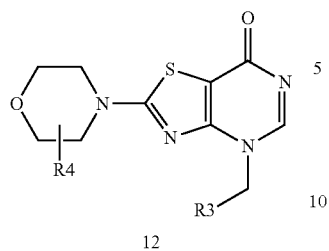

12

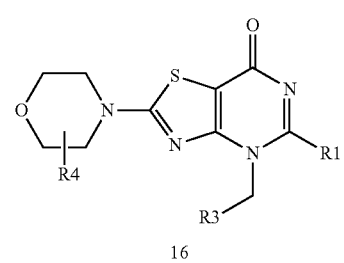

16

The alternative route to prepare this class of compounds is to start from 2-(methylthio)[1,3]thiazolo[4,5-d]pyrimidin-7(4H)-one (9) (ref. Wobig, D. *Liebigs Annalen der Chemie* 1989, 4 409-411). Similarly, N-alkylation with substituted benzyl bromide or heteroaryl bromide, affords either the desired product 10, or a mixture of 10 and its regioisomer, which are separable by flash column chromatography on silica gel. Methylthioether of 10 is oxidized with oxone to sulfone 11, which is then replaced with substituted morpholine in the presence of triethylamine (TEA) in DMF, DMA or NMP to give the desired products 12.

4-amino-2-(4-morpholinyl)-1,3-thiazole-5-carbonitriles of structure 13 can also serve as a useful starting material to prepare compounds of this class. As shown in scheme 3, methyl N-cyano-carbimidothioates 3 can be reacted with sodium cyanomethanethiolate in ethanol to produce amino thiazole 13. Subsequent acylation of the amino thiazole with an acid chloride in pyridine with a catalytic amount of DMAP can then provide compound 14 which can alkylated with an alkyl halide in the presence of $K_2CO_3$ in DMF to provide the cyclization intermediate 15. Hydrolysis of the nitrile with sodium perborate is followed by ring closure in an aqueous mixture of THF and MeOH to yield final compounds 16.

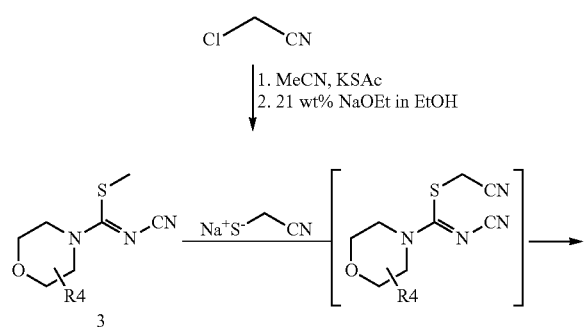

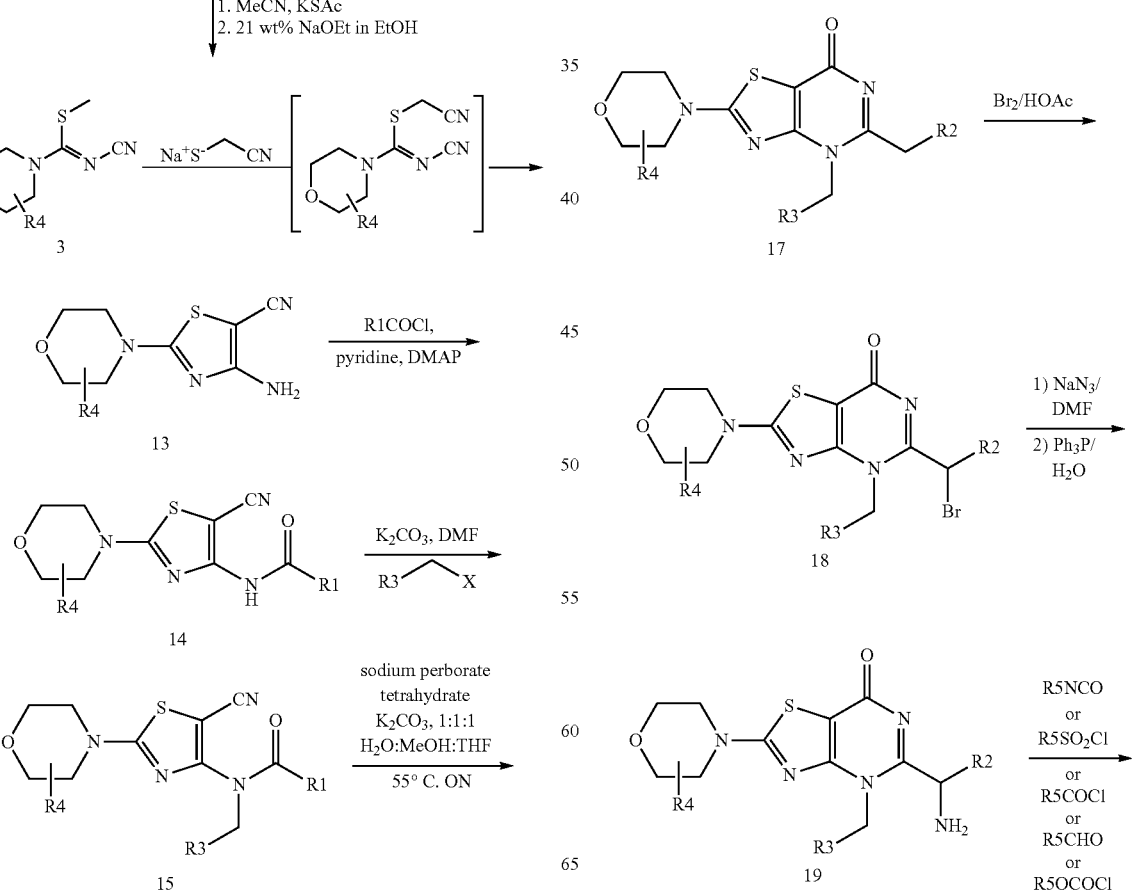

-continued

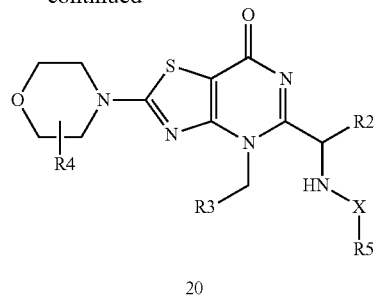

X = CH₂, CO, SO₂, CONH, CO₂

Selective bromination of advanced intermediate thiazolopyrimidinone 17 with stoichiometric amounts of bromine in acetic acid can provide bromo intermediate 18 which can then reacted with NaN₃ in a suitable polar solvent such as DMF followed by reduction with PPh₃ and water to give the amine intermediate 19. Amine 19 can be reacted with isocyanates, sulfonyl chlorides, acid chlorides, aldehydes (with a suitable reducing agent), and chloroformates to produce the corresponding ureas, sulfonamides, amides, substituted amines and carbamates, 20.

Scheme 5

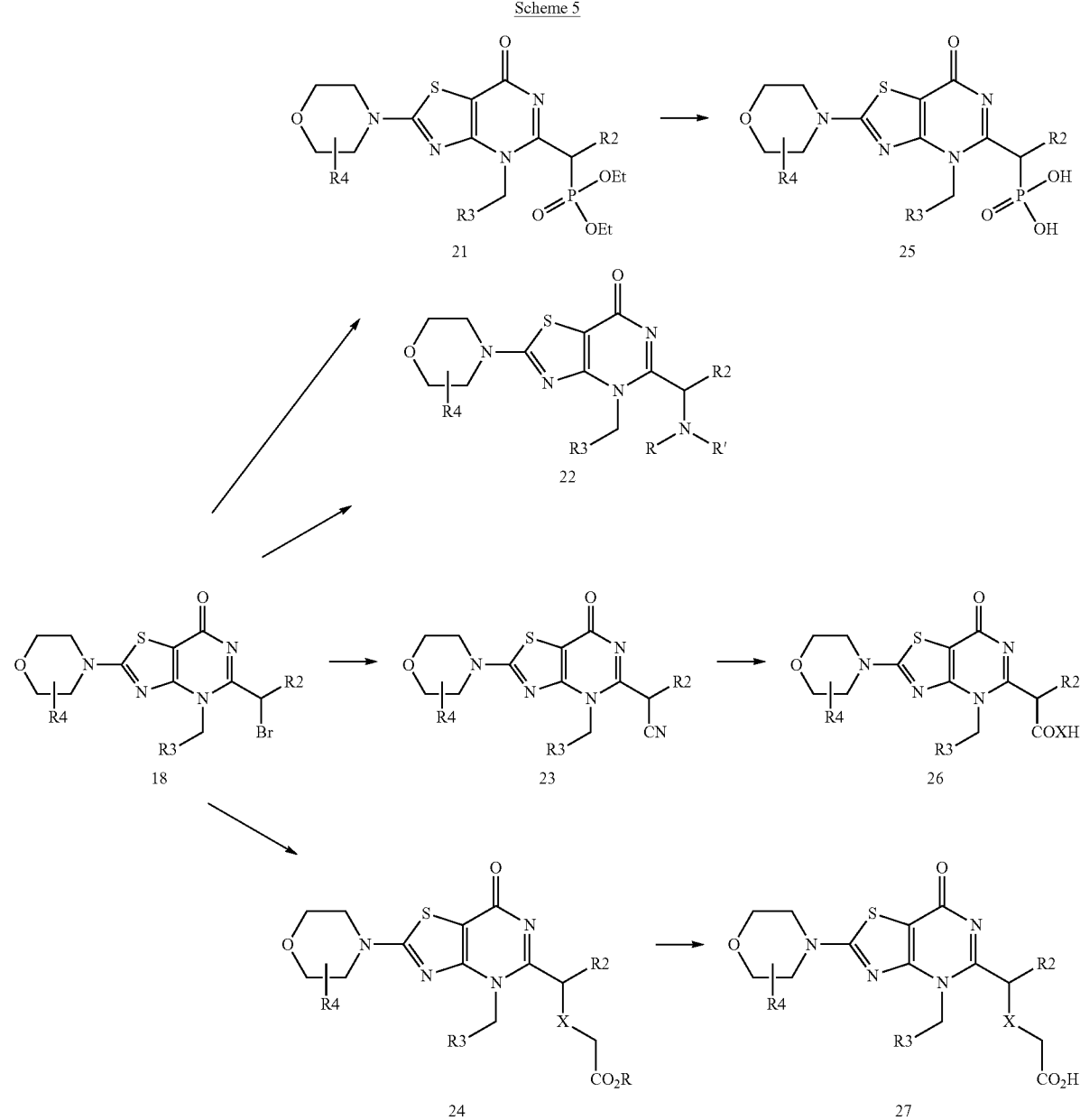

X = O, NH

Bromo intermediate 18 can be used as starting material to prepare a variety of derivatives described in scheme 5 using standard synthetic manipulations.

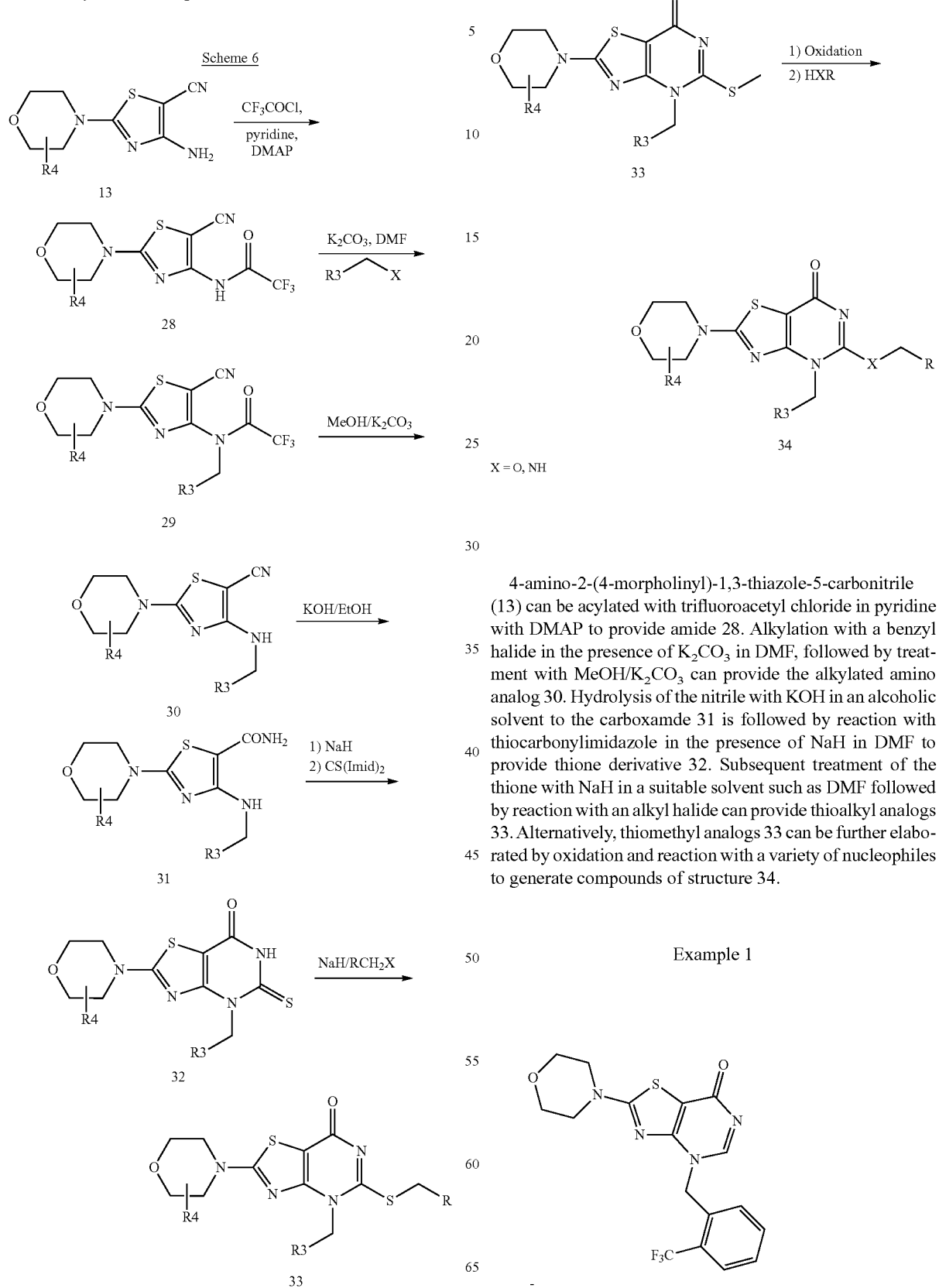

X = O, NH 4-amino-2-(4-morpholinyl)-1,3-thiazole-5-carbonitrile (13) can be acylated with trifluoroacetyl chloride in pyridine with DMAP to provide amide 28. Alkylation with a benzyl halide in the presence of $K_2CO_3$ in DMF, followed by treatment with MeOH/$K_2CO_3$ can provide the alkylated amino analog 30. Hydrolysis of the nitrile with KOH in an alcoholic solvent to the carboxamde 31 is followed by reaction with thiocarbonylimidazole in the presence of NaH in DMF to provide thione derivative 32. Subsequent treatment of the thione with NaH in a suitable solvent such as DMF followed by reaction with an alkyl halide can provide thioalkyl analogs 33. Alternatively, thiomethyl analogs 33 can be further elaborated by oxidation and reaction with a variety of nucleophiles to generate compounds of structure 34.

Example 1

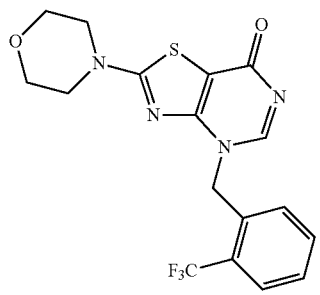

Preparation of 2-(4-morpholinyl)-4-{[2(trifluoromethyl)phenyl]methyl}[1,3]thiazolo[4,5-d]pyrimidin-7(4H)-one

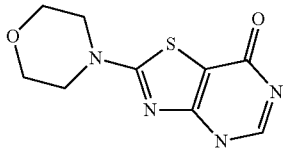 [SMILES: O=c1nc[nH]c2nc(N3CCOCC3)sc12]

a) 2-(4-Morpholinyl)[1,3]thiazolo[4,5-d]pyrimidin-7(4H)-one

A sealed tube was charged with methyl 4-amino-2-(4-morpholinyl)-1,3-thiazole-5-carboxylate (4 g, 16.44 mmol) and formamide (40 mL, 1004 mmol). The reaction was heated at 150° C. overnight. The reaction mixture was cooled, filtered, and the solid was washed with DCM and MeOH. The solid was collected and dried under vacuum to give 3.65 g (93%) of product. LCMS (ES) m/z=239.0 (M+H)+, $^1$H NMR (400 MHz, DMSO-d6) δppm 12.4 (br s, 1H, NH), 8.10 (s, 1H) 3.72 (m, 4H). 3.58 (m, 4H).

b) 2-(4-Morpholinyl)-4-{[2-(trifluoromethyl)phenyl]methyl}[1,3]thiazolo[4,5-d]pyrimidin-7(4H)-one Lithium bis(trimethylsilyl)amide (0.755 mL, 0.755 mmol) was added to a suspension of 2-(4-morpholinyl)[1,3]thiazolo[4,5-d]pyrimidin-7(4H)-one (90 mg, 0.378 mmol) in tetrahydrofuran (THF) (3 mL) at 0° C. under nitrogen. The mixture was stirred at 0° C. for 30 min before the addition of 1-(bromomethyl)-2-(trifluoromethyl)benzene (0.069 mL, 0.453 mmol). The mixture was warmed up to RT and stirred overnight. The solvent was removed and the residue was partitioned between DCM and brine. The organic layer was concentrated and the residue was purified on a biotage column (5% MeOH/DCM) to give 80 mg (55%) of the product (the undesired regioisomer (24 mg, 17%) was less polar on silica gel). LCMS (ES) m/z=397.0 (M+H)+, $^1$H NMR (400 MHz, CDCl$_3$-d1) δppm 8.05 (s, 1H), 7.76 (d, J=7.6 Hz, 1H), 7.45~7.55 (m, 2H), 7.05 (d, J=7.6 Hz, 1H), 5.54 (s, 2H), 3.80 (m, 4H), 3.58 (m, 4H).

Example 2

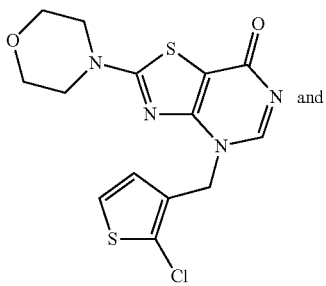

and

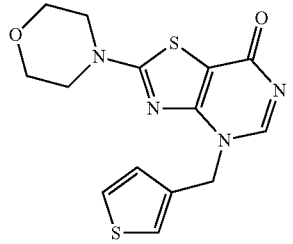

Preparation of 4-[(2-chloro-3-thienyl)methyl]-2-(4-morpholinyl)[1,3]thiazolo[4,5-d]pyrimidin-7(4H)-one and 2-(4-morpholinyl)-4-(3-thienylmethyl)[1,3]thiazolo[4,5-d]pyrimidin-7(4H)-one a) 4-[(2-Bromo-3-thienyl)methyl]-2-(4-morpholinyl)[1,3]thiazolo[4,5-d]pyrimidin 7(4H)-one

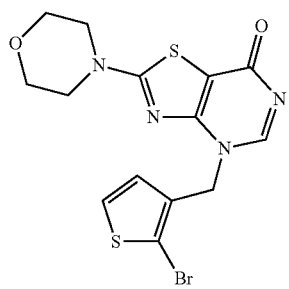 [SMILES: O=c1ncn(Cc2ccsc2Br)c2nc(N3CCOCC3)sc12]

The titled compound was prepared according to procedures of Example 1 except substituting 2-bromo-3-(bromomethyl)thiophene for 1-(bromomethyl)-2-(trifluoromethyl)benzene. LCMS (ES) m/z=413/415 (M+H); $^1$H NMR (400 MHz, METHANOL-d4) δppm 8.63 (s, 1H), 7.46 (d, J=5.6 Hz, 1H), 7.05 (d, J=5.6 Hz, 1H), 5.43 (s, 2H), 3.83-3.81 (m, 4H), 3.80-3.70 (m, 4H).

b) 4-[(2-Chloro-3-thienyl)methyl]-2-(4-morpholinyl)[1,3]thiazolo[4,5-d]pyrimidin-7(4H)-one and 2-(4-morpholinyl)-4-(3-thienylmethyl)[1,3]thiazolo[4,5-d]pyrimidin-7(4H)-one To a 5 mL microwave tube were charged with 4-[(2-bromo-3-thienyl)methyl]-2-(4-morpholinyl)[1,3]thiazolo[4,5-d]pyrimidin-7(4H)-one (50 mg, 0.121 mmol), copper(I) chloride (24 mg, 0.242 mmol) and N,N-Dimethylformamide (DMF) (2 ml). The reaction mixture was heated at 220° C. in a microwave reactor for 30 minutes. The reaction mixture was filtered and concentrated, and the residue was purified by reverse phase HPLC (10%-65% CH$_3$CN/H$_2$O, 0.1% TFA) to give two products. The first elute was 2-(4-morpholinyl)-4-(3-thienylmethyl)[1,3]thiazolo[4,5-d]pyrimidin-7(4H)-one. LCMS (ES) m/z=335.0 (M+H); $^1$H NMR (400 MHz, METHANOL-d4) δppm 8.40 (s, 1H), 7.40-7.39 (m, 1H), 7.35-7.33 (m, 1H), 7.08-7.07 (m, 1H), 5.38 (s, 2H), 3.90-3.87 (m, 4H), 3.79-3.65 (m, 4H). The second elute was 4-[(2-Chloro-3-thienyl)methyl]-2-(4-morpholinyl)[1,3]thiazolo[4,5-d]pyrimidin-7(4H)-one. LCMS (ES) m/z=368.9 (M+H); 1H NMR (400 MHz, METHANOL-d4) δppm 8.25 (s, 1H), 7.15 (d, J=6.0 Hz, 1H), 6.94 (d, J=6.0 Hz, 1H), 5.31 (s, 2H), 3.89-3.87 (m, 4H), 3.75-3.65 (m, 4H).

Example 3

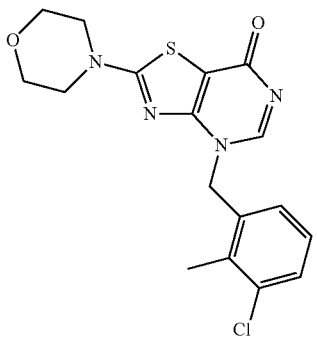 [SMILES: Cc1c(Cl)cccc1Cn1cnc(=O)c2sc(N3CCOCC3)nc21]

Preparation of 4-[(3-chloro-2-methylphenyl)methyl]-2-(4-morpholinyl)[1,3]thiazolo[4,5-d]pyrimidin-7(4H)-one a) Methyl 3-chloro-2-methylbenzoate

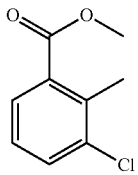

A solution of 3-chloro-2-methylbenzoic acid (1 g, 5.86 mmol) and sulfuric acid (0.312 mL, 5.86 mmol) in Methanol (5 mL) was charged into a round bottom flask. The reaction was stirred at reflux overnight and cooled to RT. 1N NaOH was added to adjust pH to 7. The mixture was diluted with ether, which was washed with brine. The organic layer was dried over MgSO₄ and the solvent was removed to afford 1.07 g of crude product (99%). $^1$H NMR (400 MHz, CDCl3) δppm 7.71 (m, 1H), 7.52 (m, 1H), 7.20 (m, 1H), 3.92 (s, 3H). 2.62 (s, 3H).

b) (3-Chloro-2-methylphenyl)methanol

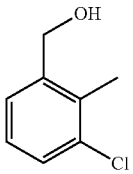

A solution of lithium aluminium hydride (29.8 mL, 29.8 mmol) in THF was cooled to 0° C., and a solution of methyl 3-chloro-2-methylbenzoate (2.5 g, 13.54 mmol) in Tetrahydrofuran (THF) (20 mL) was added dropwise. The mixture was stirred at 0° C. for half hour, warmed up to RT gradually, and stirred at RT for 2 hours. Water and 6N NaOH (4 ml) were added to quench the reaction. The mixture was filtered and the filtrate was concentrated to afford the crude product as a white solid (2.0 g, 94%). $^1$H NMR (400 MHz, CDCl₃) δppm 7.30~7.35 (m, 2H), 7.16 (m, 1H), 4.74 (s, 2H), 2.40 (s, 3H).

c) 1-(Bromomethyl)-3-chloro-2-methylbenzene

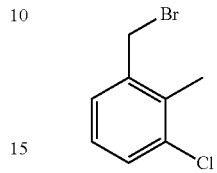

To a solution of phosphorus tribromide (0.422 mL, 4.47 mmol) in Toluene (30 mL) was added (3-chloro-2-methylphenyl)methanol (2 g, 12.77 mmol). The reaction was stirred at RT overnight. The solvent was removed and the residue was partitioned between EtOAc and brine. The organic layer was concentrated and the residue was purified by biotage (5% EA/hexane) to give the product (2.0 g, 71%). $^1$H NMR (400 MHz, CDCl3) δppm 7.36 (m, 1H), 7.24 (m, 1H), 7.12 (m, 1H), 4.56 (s, 2H). 2.48 (s, 3H).

d) 4-[(3-Chloro-2-methylphenyl)methyl]-2-(4-morpholinyl)[1,3]thiazolo[4,5-d]pyrimidin-7(4H)-one The titled compound was prepared according to procedure 1(b) in Example 1 except substituting 1-(bromomethyl)-2-(trifluoromethyl)benzene with 1-(bromomethyl)-3-chloro-2-methylbenzene. LCMS (ES) m/z 377.0 (M+H)⁺; $^1$H NMR (400 MHz, CDCl₃-d1) δppm 8.31 (br, s, 1H), 7.43 (m, 1H), 7.17 (m, 1H), 6.97 (m, 1H), 5.44 (s, 2H), 3.85 (m, 4H), 3.67 (m, 4H), 2.43 (s, 3H).

Example 4

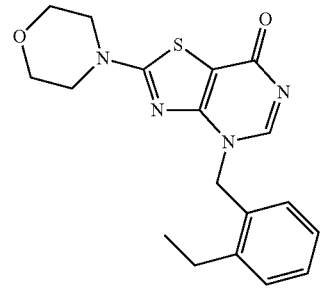 [SMILES: CCc1ccccc1Cn1cnc(=O)c2sc(N3CCOCC3)nc21]

Preparation of 4-[(2-ethylphenyl)methyl]-2-(4-morpholinyl)[1,3]thiazolo[4,5-d]pyrimidin-7(4H)-one A mixture of 4-[(2-bromophenyl)methyl]-2-(4-morpholinyl)[1,3]thiazolo[4,5-d]pyrimidin-7(4H)-one (120 mg, 0.295 mmol), ethylboronic acid (32.7 mg, 0.442 mmol) and potassium phosphate (125 mg, 0.589 mmol) in Toluene (2 mL) was charged into a microwave tube under N₂, followed by the addition of S-Phos (12.10 mg, 0.029 mmol), and Pd(OAc)₂ (3.31 mg, 0.015 mmol). The mixture was irradiated with microwave at 150° C. for 15 min. The solvent was removed and the residue was partitioned between DCM and brine. The organic layer was concentrated and the residue was purified by reverse phase HPLC (5% org~50% org) to give the product (60 mg, 58%). LCMS (ES) m/z 357.1 (M+H)+, $^1$H NMR (400 MHz, CDCl$_3$-d1)) δppm 8.50 (br, s, 1H), 7.38 (m, 1H), 7.33 (m, 1H), 7.25 (m, 1H), 7.09 (m, 1H), 5.48 (s, 2H), 3.86 (m, 4H), 3.69 (m, 4H), 2.71 (q, 2H), 1.25 (t, 3H).

Example 5

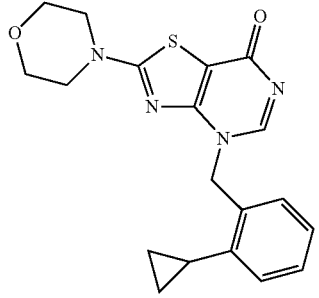 [SMILES: O=c1ncn(Cc2ccccc2C2CC2)c2nc(N3CCOCC3)sc12]

Preparation of 4-[(2-cyclopropylphenyl)methyl]-2-(4-morpholinyl)[1,3]thiazolo[4,5-d]pyrimidin-7(4H)-one The titled compound was prepared according the procedure in Example 4 except substituting ethylboronic acid with cyclopropylboronic acid. LCMS (ES) m/z 369.1 (M+H)+; $^1$H NMR (400 MHz, CDCl$_3$-d1)) δppm 8.00 (s, 1H), 7.31 (m, 1H), 7.20 (m, 1H), 7.14 (m, 1H), 7.09 (m, 1H), 5.52 (s, 2H), 3.83 (m, 4H), 3.63 (m, 4H), 1.86 (m, 1H), 0.95 (m, 2H), 0.71 (m, 2H).

Example 6

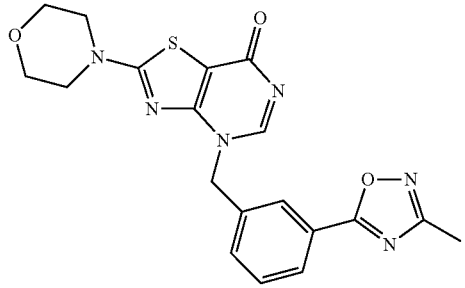 [SMILES: Cc1noc(-c2cccc(Cn3cnc(=O)c4sc(N5CCOCC5)nc43)c2)n1]

Preparation of 4-{[3-(3-methyl-1,2,4-oxadiazol-5-yl)phenyl]methyl}-2-(4-morpholinyl)[1,3]thiazolo[4,5-d]pyrimidin-7(4H)-one A sealed tube was charged with 2-(4-morpholinyl)[1,3]thiazolo[4,5-d]pyrimidin-7(4H)-one (80 mg, 0.336 mmol) in 5 mL of THF, isopropylmagneiumchloride (0.168 mL, 0.336 mmol), and LiHMDS (0.672 mL, 0.672 mmol) at 0° C. Then 5-[3-(bromomethyl)phenyl]-3-methyl-1,2,4-oxadizole (102 mg, 0.403 mmol) was added. The reaction mixture was stirred at RT for 18 hr. LCMS showed one product peak and remaining starting material (1.5:1 product:SM). The reaction mixture was heated at 60° C. for 3 hr. LCMS showed product: SM=3:1. Heating was continued at 65° C. for another 2 hr. LCMS showed Pdt:SM=4:1 with trace amount undesired isomer. The mixture was concentrated and purified by column chromatography (5% MeOH/DCM) on silica gel to give the product contaminated with unreacted starting material. The crude product was dissolved in 200 mL of DCM and washed with 1N NaOH (50 ml). TLC showed no SM left. The organic layer was dried over Na$_2$SO$_4$, filtered and concentrated to afford 90 mg of the product as a white solid.

Example 7

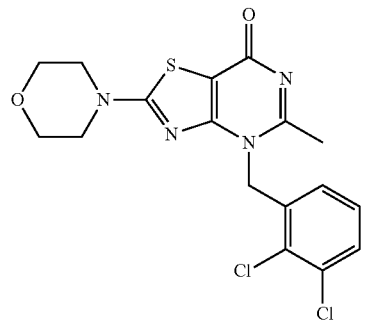 [SMILES: Cc1nc(=O)c2sc(N3CCOCC3)nc2n1Cc1cccc(Cl)c1Cl]

Preparation of 4-[(2,3-dichlorophenyl)methyl]-5-methyl-2-(4-morpholinyl)[3]thiazolo[4,5-d]pyrimidin-7(4H)-one a) 5-Methyl-2-(4-morpholinyl)[1,3]thiazolo[4,5-d]pyrimidin-7(4H)-one

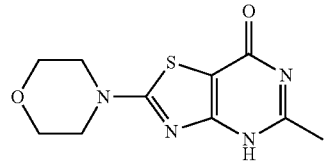 [SMILES: Cc1nc(=O)c2sc(N3CCOCC3)nc2[nH]1]

A mixture of acetic anhydride (4 ml, 42.4 mmol), Acetic Acid (2.00 ml) and 4-amino-2-(4-morpholinyl)-1,3-thiazole-5-carboxamide (200 mg, 0.876 mmol) was stirred at 60° C. for 3 h, then quenched with methanol and concentrated under reduced pressure. A mixture of the residue, Ethanol (2.000 ml) and 6N NaOH (2 ml, 12.00 mmol) was irradiated (uwave) at 120° C. for 30 min, then acidified with 6N HCl to pH ~5. The precipitate was collected, rinsed with water, and dried under vacuum to furnish 5-methyl-2-(4-morpholinyl)[1,3]thiazolo[4,5-d]pyrimidin-7(4H)-one (175 mg, 79%). LC/MS: MS(ES+) m/e 253 (MH+); $^1$H NMR (400 MHz, DMSO-d$_6$) δ ppm 2.31 (s, 3H) 3.54-3.59 (m, 4H) 3.69-3.75 (m, 4H) 12.34 (br. s., 1H).

b) 4-[(2,3-dichlorophenyl)methyl]-5-methyl-2-(4-morpholinyl)[1,3]thiazolo[4,5-d]pyrimidin-7(4H)-one A solution of 5-methyl-2-(4-morpholinyl)[1,3]thiazolo[4,5-d]pyrimidin-7(4H)-one (75 mg, 0.297 mmol) in Tetrahydrofuran (THF) (1.5 mL) was stirred at 0° C. for 15 min, then lithium bis(trimethylsilyl)amide (446 μl, 0.446 mmol, 1.0 M in THF) was added and stirring was continued for 30 min. 2,3-Dichlorobenzyl bromide (86 mg, 0.357 mmol) was added and the mixture was allowed to warm to room temperature and stirred overnight. Additional stirring at 65° C. for 2 h completed the reaction resulting in a mixture of the desired product and the regio-isomer. The reaction was concentrated and the residue was purified by reversed-phase HPLC to provide the product, 4-[(2,3-dichlorophenyl)methyl]-5-methyl-2-(4-morpholinyl)[1,3]thiazolo[4,5-d]pyrimidin-7

(4H)-one (28 mg, 23%). LC/MS: MS (ES⁺) m/e 411 (MH⁺); 1H NMR (400 MHz, DMSO-d₆) δ ppm 2.44 (s, 3H) 3.52 (m, 4H) 3.64-3.72 (m, 4H) 5.60 (s, 2H) 6.90 (d, J=7.3 Hz, 1H) 7.33 (m, 1H) 7.64 (d, J=8.0 Hz, 1H).

Example 8

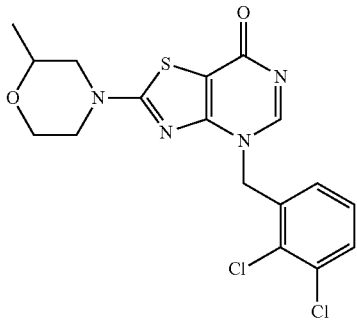 [SMILES: CC1CN(c2nc3c(s2)c(=O)ncn3Cc2cccc(Cl)c2Cl)CCO1]

Preparation of (rac)-4-[(2,3-dichlorophenyl)methyl]-2-(2-methyl-4-morpholinyl)[1,3]thiazolo[4,5-d]pyrimidin-7(4H)-one Method A a) 1-[(2-hydroxyethyl)(phenylmethyl)amino]-2-propanol

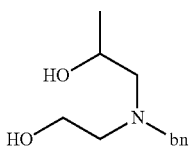

2-(Benzylamino)ethanol (9.06 g, 60 mmol) and propylene oxide (6.96 g, 120 mmol) were mixed in a sealed tube and the reaction mixture was stirred at 40° C. overnight. The excess of propylene oxide was evaporated in vacuo to give the diol residue, which was used directly to next step without further purification.

b) 4-Benzyl-2-methylmorpholine

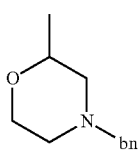

The above mentioned diol residue was dissolved in dioxane (50 mL). KOH (10.08 g, 180 mmol) and tri(3,6-dioxaheptyl)amine (200 mg, 0.6 mmol) were added to the mixture and the resultant mixture was cooled to 0° C. Then, tosyl chloride (12.58 g, 66 mmol) was added dropwise. The reaction mixture was allowed to stir at 0° C. for an hour and then warmed to ambient temperature with stirring for an additional 4 hours. Then the reaction mixture was concentrated under reduced pressure. The residue was taken into dichloromethane and washed with water, saturated brine. The organic layer was dried over Na₂SO₄, filtered and concentrated. The residue was purified through silica gel column chromatography to give the desired product as a colorless oil (8.0 g, 75%, two steps). LC-MS: 192 (MH⁺).

c) 2-Methylmorpholine hydrochloride

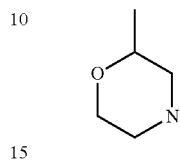

To a solution of 4-benzyl-2-methylmorpholine (7 g, 36.6 mmol) in acetonitrile (200 mL) was added K₂CO₃ (15.2 g, 73.2 mmol) and α-chloroethyl chloridocarbonate (10.4 g, 73.2 mmol). The reaction mixture was stirred at ambient temperature for 2 hours. Then solvent was removed under reduced pressure. The residue was dissolved in dichloromethane. The organic layer was washed with water, dried over Na₂SO₄ and concentrated to give a residue. The residue was dissolved in methanol (200 mL) and stirred overnight. The solvent was removed. The residue was rinsed with dichloromethane. Filtration gave the desired product as a white solid (4.2 g, 84%). ¹H NMR (300 MHz, d6-DMSO) δ 9.76 (br, 1H), 9.63 (br, 1H), 3.91~3.71 (m, 3H), 3.13 (m, 2H), 2.88 (br, 1H), 2.61 (br, 1H), 1.09 (d, J=6.3 Hz, 3H); LC-MS: 102 (MH⁺).

d) Methyl N-cyano-2-methylmorpholine-4-carbimidothioate

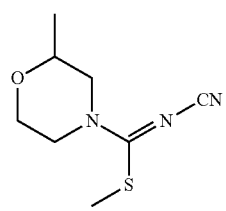

A mixture of 2-methylmorpholine hydrochloride (1.0 g, 9.9 mmol), dimethyl cyanocarbonimidodithioate (1.45 g, 9.9 mmol) and sodium carbonate (0.2 g, 1.9 mmol) in ethanol (50 mL) was stirred at ambient temperature overnight. The reaction mixture was concentrated and purified through silica gel chromatography to give the desired product (1.25 g, 63%). LC-MS: 200 (MH⁺).

e) Methyl 4-amino-2-(2-methylmorpholino)thiazole-5-carboxylate

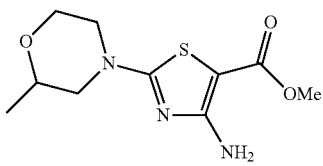 [SMILES: COC(=O)c1sc(N2CCOC(C)C2)nc1N]

A mixture of methyl N-cyano-2-methylmorpholine-4-carbimidothioate (1.2 g, 6 mmol), methyl 2-mercaptoacetate (0.64 g, 6 mmol) and triethylamine (1.2 g, 12.0 mmol) in methanol (50 mL) was stirred at ambient temperature overnight. Solvent was removed. The residue was dissolved in dichloromethane, washed with water and brine. The organic layer was concentrated to give the desired product (crude, 1.4 g, 93%). $^1$H NMR (300 MHz, CDCl$_3$) δ 5.81 (br, 2H), 3.97~3.94 (m, 1H), 3.75 (s, 3H), 3.69-3.59 (m, 3H), 3.28-3.14 (m, 1H), 2.87-2.80 (m, 1H), 1.22 (d, J=6.0 Hz, 3H); LC-MS: 258 (MH$^+$).

f) 2-(2-Methylmorpholino)thiazolo[4,5-d]pyrimidin-7(4H)-one

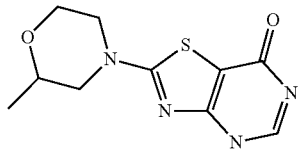 [SMILES: CC1CN(c2nc3[nH]cnc(=O)c3s2)CCO1]

The solution of methyl 4-amino-2-(2-methylmorpholino)thiazole-5-carboxylate (1.4 g, 5.4 mmol) in formamide (5 mL) was stirred at 200° C. for 1.5 hours. The mixture was cooled to ambient temperature. The precipitate was collected through filtration and washed with water to give the desired product (1.0 g, 73%). $^1$H NMR (300 MHz, d6-DMSO) δ 12.42 (br, 1H), 8.09 (s, 1H), 3.93~3.82 (m, 3H), 3.61-3.54 (m, 2H), 3.24 (m, 1H), 2.92 (m, 1H), 1.16 (m, 3H); LC-MS: 253 (MH$^+$).

g) 4-(2,3-Dichlorobenzyl)-2-(2-methylmorpholino)thiazolo[4,5-d]pyrimidin-7(4H)-one LiHMDS (0.9 N, 2.7 mL, 2.4 mmol) was added to a solution of 2-(2-methylmorpholino)thiazolo[4,5-d]pyrimidin-7(4H)-one (300 mg, 1.2 mmol) in THF (6.0 mL) at 0° C. The reaction mixture was stirred for an hour. 1-(bromomethyl)-2,3-dichlorobenzene (285 mg, 1.2 mmol) was added to the mixture and the resultant mixture was stirred for 18 hours. The reaction was quenched by water and extracted with dichloromethane. The organic layer was dried, concentrated and purified through silica gel chromatography to give the desired product as a solid (210 mg, 43%). $^1$H NMR (300 MHz, d$_6$-DMSO) δ 8.48 (s, 1H), 7.63 (d, J=8.1 Hz, 1H), 7.35 (m, 1H), 7.18 (d, J=7.8 Hz, 1H), 5.47 (s, 2H), 3.89 (m, 1H), 3.82~3.75 (m, 2H), 3.56~3.52 (m, 2H), 3.26~3.16 (m, 1H), 2.91 (m, 1H), 1.14 (d, J=6.0 Hz, 3H); LC-MS: 411 (MH$^+$).

Method B a) 4-Amino-2-(methylthio)thiazole-5-carboxamide

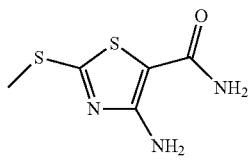

A mixture of potassium (Z)-methyl cyanocarbonimidodithioate (10.0 g, 58.7 mmol) and 2-chloroacetamide (6.04 g, 64.6 mmol) in ethanol (20 mL) was refluxed for 1 h. After cooling to ambient temperature, sodium methoxide (3.49 g, 64.6 mmol) was added to the mixture. The mixture was stirred at reflux for 3 hours. The mixture was cooled to ambient temperature and water (50 mL) was added. The precipitate formed was collected by filtration. The precipitate was further washed with water and dried in vacuo. The product was obtained as a yellow solid (3.372 g, 30%). $^1$H NMR (300 MHz, d6-DMSO) δ 6.96 (s, 2H), 6.89 (s, 2H), 2.64 (s, 3H); LC-MS: 190 (MH$^+$).

b) 2-(Methylthio)thiazolo[4,5-d]pyrimidin-7(4H)-one

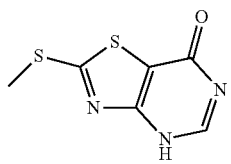

A mixture of 4-amino-2-(methylthio)thiazole-5-carboxamide (3.37 g, 17.8 mmol) in formic acid (10 mL) was stirred at reflux for 12 hours. After cooled to ambient temperature, the reaction mixture was diluted with water (30 mL) and the precipitate was collected by filtration. The resulting solid was further washed with water and dried in vacuo. The product was obtained as a yellow solid (2.978 g, 84%). $^1$H NMR (300 MHz, d6-DMSO) δ 12.83 (br, 1H), 8.26 (s, 1H), 2.80 (s, 3H); LC-MS: 200 (MH$^+$).

c) 4-(2,3-Dichlorobenzyl)-2-(methylthio)thiazolo[4,5-d]pyrimidin-7(4H)-one

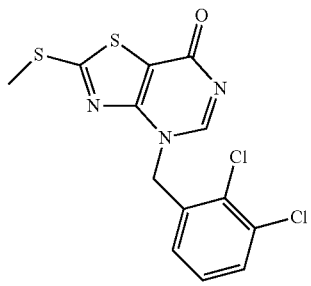 [SMILES: CSc1nc2c(s1)c(=O)ncn2Cc1cccc(Cl)c1Cl]

To a suspension of 2-(methylthio)thiazolo[4,5-d]pyrimidin-7(4H)-one (2.978 g, 14.94 mmol) in THF (200 mL) at 0° C. was added dropwise of LiHMDS (18.3 mL, 16.44 mmol). The resulting mixture was stirred at 0-5° C. for 3 hours and 1-(bromomethyl)-2,3-dichlorobenzene (3.946 g, 16.44 mmol) in THF (30 mL) was added dropwise to the reaction mixture over a period of 2 hours. The reaction mixture was allowed to warm to ambient temperature slowly and stirred at ambient temperature for 16 hours. The reaction mixture was filtered and the filtrate was concentrated under reduced pressure. The residue was purified by flash column chromatography on silica gel (2×20 cm, DCM:MeOH=30:1 elution) to give the desired product as a white solid (0.671 g, 13%). $^1$H NMR (300 MHz, CDCl$_3$) δ 8.33 (s, 1H), 7.50 (m, 1H), 7.26~7.16 (m, 2H), 5.56 (s, 2H), 2.74 (s, 3H); LC-MS: 358 (MH$^+$); IR (thin film): 3073, 2986, 1651, 1619, 1598, 1426, 1384, 1221, 1055 cm$^{-1}$.

d) 4-(2,3-Dichlorobenzyl)-2-(methylsulfonyl)thiazolo[4,5-d]pyrimidin-7(4H)-one

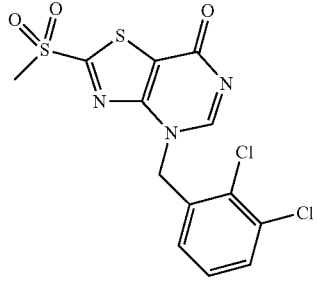 [SMILES: CS(=O)(=O)c1nc2c(s1)c(=O)ncn2Cc1cccc(Cl)c1Cl]

To a solution of 4-(2,3-dichlorobenzyl)-2-(methylthio) thiazolo[4,5-d]pyrimidin-7(4H)-one (660 mg, 1.842 mmol) in THF (150 mL) and water (60 mL) at 0-5° C. was added Oxone (6.8 g, 11.05 mmol). The resulting mixture was stirred at ambient temperature for 60 hours. After removing THF under reduced pressure, the precipitate formed was collected by filtration and the precipitate was further washed with water, ether and dried in vacuo to give the desired product as a white solid (574 mg, 80%). The compound was directly used in next step without further purification. $^1$H NMR (300 MHz, CDCl$_3$) δ 8.53 (br, 1H), 7.54 (dd, J=7.8, 1.5 Hz, 1H), 7.35~7.24 (m, 2H), 5.61 (s, 2H), 3.33 (s, 3H); LC-MS: 390 (MH$^+$); IR (thin film): 3027, 3008, 2925, 1649, 1602, 1488, 1461, 1424, 1405, 1335 cm$^{-1}$.

e) 4-(2,3-dichlorobenzyl)-2-(2-methylmorpholino) thiazolo[4,5-d]pyrimidin-7(4H)-one A mixture of triethylamine (2 drops), 2-methylmorpholine hydrochloride (16 mg, 0.154 mmol) and 4-(2,3-dichlorobenzyl)-2-(methylsulfonyl)thiazolo[4,5-d]pyrimidin-7(4H)-one (20 mg, 0.051 mmol) in DMF was stirred at 60° C. for 1 h. After cooled to ambient temperature, the mixture was diluted with water (10 mL) and extracted with dichloromethane (15 mL×3). The combined organic layers were washed with saturated brine, dried over anhydrous Na$_2$SO$_4$, filtered and concentrated in vacuo. The residue was purified by flash column chromatography on silica gel (DCM:MeOH=20:1 elution) to give the desired product (8 mg, 38%) as a white solid. $^1$H NMR (300 MHz, d6-DMSO) δ 8.49 (s, 1H), 7.63 (d, J=7.2 Hz, 1H), 7.35 (d, J=7.8 Hz, 1H), 7.16 (s, J=6.9 Hz, 1H), 5.46 (s, 2H), 3.88 (dd, J=12.3, 2.7 Hz, 1H), 3.77 (br, 2H), 3.55-3.47 (m, 2H), 3.31-3.20 (m, 1H), 2.94-2.89 (m. 1H), 1.13 (d, J=5.7 Hz, 3H); LC-MS: 411 (MH$^+$); IR (thin film): 2976, 2920, 2855, 2360, 1627, 1605, 1555, 1495, 1444 cm$^{-1}$.

The following compounds in the table were prepared according to the procedures of Example 1 or Example 6.

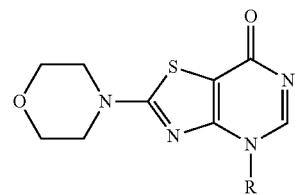

Table of Spectra Data

| Example | R | Name | Data |
|---|---|---|---|
| 9 | benzyl | 2-(4-morpholinyl)-4(phenylmethyl)[1,3]thiazolo[4,5d]pyrimidin-7(4H)-one | LCMS (ES) m/z 329.1 (M + H)$^+$, $^1$H NMR (600 MHz, DMSO-d6) δ ppm 8.62 (s, 1H), 7.31~7.37 (m, 5H), 5.16 (s, 2H), 3.70~3.73 (m, 4H), 3.55-3.61 (m, 4H) |
| 10 | 2-methylphenyl-CH$_2$- | 4-[(2-methylphenyl)methyl]-2-(4-morpholinyl)[1,3]thiazolo[4,5-d]pyrimidin-7(4H)-one | LCMS (ES) m/z 343.1 (M + H)$^+$, $^1$H NMR (400 MHz, Methanol-d4) δ ppm 8.31 (s, 1H), 7.18~7.26 (m, 3H), 7.05 (m, 1H), 5.49 (s, 2H), 3.79 (m, 4H), 3.67 (m, 4H), 2.41 (s, 3H) |
| 11 | 2-fluorophenyl-CH$_2$- | 4-[(2-fluorophenyl)methyl]-2-(4-morpholinyl)[1,3]thiazolo[4,5-d]pyrimidin-7(4H)-one | LCMS (ES) m/z 347.0 (M + H)$^+$, $^1$H NMR (400 MHz, CDCl$_3$-d1) δ ppm 8.19 (s, 1H), 7.33~7.40 (m, 2H), 7.03~7.24 (m, 2H), 5.34 (s, 2H), 3.85 (m, 4H), 3.65 (m, 4H) |
| 12 | 2-chlorophenyl-CH$_2$- | 4-[(2-chlorophenyl)methyl]-2-(4-morpholinyl)[1,3]thiazolo[4,5-d]pyrimidin-7(4H)-one | LCMS (ES) m/z 363.0 (M + H)$^+$, $^1$H NMR (400 MHz, CDCl$_3$-d1) δ ppm 8.15 (s, 1H), 7.45 (m, 1H), 7.21~7.34 (m, 3H), 5.41 (s, 2H), 3.83 (m, 4H), 3.63 (m, 4H) |
| 13 | 2-bromophenyl-CH$_2$- | 4-[(2-bromophenyl)methyl]-2-(4-morpholinyl)[1,3]thiazolo[4,5-d]pyrimidin-7(4H)-one | LCMS (ES) m/z 407.9 (M + H)$^+$, $^1$H NMR (400 MHz, CDCl$_3$-d1) δ ppm 8.16 (s, 1H), 7.65 (d, 1H), 7.22~7.33 (m, 2H), 7.16 (d, 1H), 5.41 (s, 2H), 3.83 (m, 4H), 3.63 (m, 4H) |

Table of Spectra Data

| Example | R | Name | Data |
|---|---|---|---|
| 14 | 3-methylphenyl methyl | 4-[(3-methylphenyl)methyl]-2-(4-morpholinyl)[1,3]thiazolo[4,5-d]pyrimidin-7(4H)-one | LCMS (ES+) m/z 343 (MH+); $^1$H NMR (400 MHz, DMSO-d$_6$) δ ppm 2.28 (s, 3 H) 3.60-3.64 (m, 4 H) 3.70-3.76 (m, 4 H) 5.29 (s, 2 H) 7.13 (d, J = 7.1 Hz, 1 H) 7.18-7.29 (m, 3 H) 8.68 (s, 1 H) |
| 15 | 3-fluorophenyl methyl | 4-[(3-fluorophenyl)methyl]-2-(4-morpholinyl)[1,3]thiazolo[4,5-d]pyrimidin-7(4H)-one | LC/MS (ES+) m/e 347 (MH+); $^1$H NMR (400 MHz, DMSO-d$_6$) δ ppm 3.57-3.65 (m, 4 H) 3.69-3.76 (m, 4 H) 5.35 (s, 2 H) 7.17 (m, 1 H) 7.26 (d, J = 7.6 Hz, 1 H) 7.29-7.35 (m, 1 H) 7.37-7.47 (m, 1 H) 8.69 (s, 1 H) |
| 16 | 3-OMe phenyl methyl | 4-{[3-(methyloxy)phenyl]methyl}-2-(4-morpholinyl)[1,3]thiazolo[4,5-d]pyrimidin-7(4H)-one | LC/MS (ES+) m/e 359 (MH+); $^1$H NMR (400 MHz, DMSO-d$_6$) δ ppm 3.59-3.66 (m, 4 H) 3.70-3.76 (m, 7 H) 5.31 (s, 2 H) 6.89 (m, 1 H) 6.99 (d, J = 7.8 Hz, 1 H) 7.02-7.06 (m, 1 H) 7.28 (m, 1 H) 8.73 (s, 1 H) |
| 17 | 3-chlorophenyl methyl | 4-[(3-chlorophenyl)methyl]-2-(4-morpholinyl)[1,3]thiazolo[4,5-d]pyrimidin-7(4H)-one | LC/MS (ES+) m/e 363 (MH+); $^1$H NMR (400 MHz, DMSO-d$_6$) δ ppm 3.57-3.63 (m, 4 H) 3.69-3.75 (m, 4 H) 5.32 (s, 2 H) 7.37-7.42 (m, 3 H) 7.56 (s, 1 H) 8.64 (s, 1 H) |
| 18 | 3-CF$_3$ phenyl methyl | 2-(4-morpholinyl)-4-{[3-(trifluoromethyl)phenyl]methyl}[1,3]thiazolo[4,5-d]pyrimidin-7(4H)-one | LC/MS (ES+) m/e 397 (MH+); $^1$H NMR (400 MHz, DMSO-d$_6$) δ ppm 3.60 (m, 4 H) 3.68-3.77 (m, 4 H) 5.42 (s, 2 H) 7.62 (m, 1 H) 7.70 (d, J = 7.8 Hz, 1 H) 7.76 (d, J = 7.8 Hz, 1 H) 7.94 (s, 1 H) 8.81 (s, 1 H) |
| 19 | 3-NO$_2$ phenyl methyl | 2-(4-morpholinyl)-4-[(3-nitrophenyl)methyl][1,3]thiazolo[4,5-d]pyrimidin-7(4H)-one | LCMS (ES) m/z = 374.0 (M + H); $^1$H NMR (400 MHz, CDCl$_3$) δ ppm 8.41 (s, 1H), 8.24-8.22 (m, 2H), 7.65-7.60 (m, 2H), 5.37(s, 2H), 3.88-3.85 (m, 4H), 3.70-3.65 (m, 4H). |
| 20 | 3-CN phenyl methyl | 3-{[2-(4-morpholinyl)-7-oxo[1,3]thiazolo[4,5-d]pyrimidin-4(7H)-yl]methyl}benzonitrile | 1H NMR (400 MHz, DMSO-d$_6$) δ ppm 3.59 (br. s., 4 H) 3.69-3.76 (m, 4 H) 5.37 (s, 2 H) 7.58 (t, J = 7.83 Hz, 1 H) 7.79 (dd, J = 13.14, 7.83 Hz, 2 H) 7.98 (s, 1 H) 8.62 (s, 1 H); LC/MS: MS (ES+) m/e 354 (MH+). |
| 21 | 3-OCF$_3$ phenyl methyl | 2-(4-morpholinyl)-4-({3-[(trifluoromethyl)oxy]phenyl}methyl)[1,3]thiazolo[4,5-d]pyrimidin-7(4H)-one | 1H NMR (400 MHz, DMSO-d$_6$) δ ppm 3.58 (br. s., 4 H) 3.71 (t, J = 4.80 Hz, 4 H) 5.36 (s, 2 H) 7.33 (d, J = 7.83 Hz, 1 H) 7.41-7.46 (m, 1 H) 7.47-7.54 (m, 2 H) 8.61 (s, 1 H); LC/MS: MS (ES+) m/e 413 (MH+). |
| 22 | 3-(1H-pyrrol-1-yl)phenyl methyl | 2-(4-morpholinyl)-4-{[3-(1H-pyrrol-1-yl)phenyl]methyl}[1,3]thiazolo[4,5-d]pyrimidin-7(4H)-one | LCMS (ES) m/z = 394.0 (M + H); 1H NMR (400 MHz, CDCl3) δ ppm 8.50 (s, 1H), 7.54-7.43 (m, 3H), 7.19-7.18 (m, 1H), 7.07-7.02 (m, 2H), 6.39-6.38 (m, 2H), 5.41(s, 2H), 3.85-3.83 (m, 4H), 3.70-3.65 (m, 4H). |

| Table of Spectra Data | | | |
|---|---|---|---|
| Example | R | Name | Data |
| 23 | (3-methyl-1,2,4-oxadiazol-5-yl)phenylmethyl group | 4-{[3-(3-methyl-1,2,4-oxadiazol-5-yl)phenyl]methyl}-2-(4-morpholinyl)[1,3]thiazolo[4,5-d]pyrimidin-7(4H)-one | LCMS (ES) m/z = 410.8 (M + H); 1H NMR (400 MHz, CDCl3) δ ppm 8.24-8.20 (m, 2H), 8.14-8.11 (m, 1H), 7.57-7.54 (m, 2H), 5.36 (s, 2H), 3.87-3.84 (m, 4H), 3.69-3.67 (m, 4H), 2.50 (s, 3H). |
| 24 | (5-methyl-1,2,4-oxadiazol-3-yl)phenylmethyl group | 4-{[3-(5-methyl-1,2,4-oxadiazol-3-yl)phenyl]methyl}-2-(4-morpholinyl)[1,3]thiazolo[4,5-d]pyrimidin-7(4H)-one | LCMS (ES) m/z = 410.9 (M + H); 1H NMR (400 MHz, CDCl3) δ ppm 9.50 (br, 1H), 8.28 (s, 1H), 8.09-8.07 (m, 1H), 7.60-7.51 (m, 2H), 5.58 (s, 1H), 3.88-7.65 (m, 8H). |
| 25 | 4-fluorobenzyl group | 4-[(4-fluorophenyl)methyl]-2-(4-morpholinyl)[1,3]thiazolo[4,5-d]pyrimidin-7(4H)-one | LC/MS (ES+) m/e 347 (MH+); $^1$H NMR (400 MHz, DMSO-$d_6$) δ ppm 3.61 (m, 4 H) 3.70-3.77 (m, 4 H) 5.33 (s, 2 H) 7.20 (m, 2 H) 7.52 (dd, J = 8.6, 5.6 Hz, 2 H) 8.74 (s, 1 H) |
| 26 | 4-chlorobenzyl group | 4-[(4-chlorophenyl)methyl]-2-(4-morpholinyl)[1,3]thiazolo[4,5-d]pyrimidin-7(4H)-one | LC/MS (ES+) m/e 363 (MH+); $^1$H NMR (400 MHz, DMSO-$d_6$) δ ppm 3.59 (m, 4 H) 3.69-3.75 (m, 4 H) 5.33 (s, 2 H) 7.41-7.50 (m, 4 H) 8.70 (s, 1 H); |
| 27 | 4-methylbenzyl group | 4-[(4-methylphenyl)methyl]-2-(4-morpholinyl)[1,3]thiazolo[4,5-d]pyrimidin-7(4H)-one | LC/MS (ES+) m/e 343 (MH+); $^1$H NMR (400 MHz, DMSO-$d_6$) δ ppm 2.27 (s, 3 H) 3.61 (m, 4 H) 3.70-3.78 (m, 4 H) 5.29 (s, 2 H) 7.17 (d, J = 7.8 Hz, 2 H) 7.33 (d, J = 7.8 Hz, 2 H) 8.71 (s, 1 H); |
| 28 | 4-cyanobenzyl group | 4-{[2-(4-morpholinyl)-7-oxo[1,3]thiazolo[4,5-d]pyrimidin-4(7H)-yl]methyl}benzonitrile | $^1$H NMR (400 MHz, DMSO-$d_6$) δ ppm 3.57 (br. s., 4 H) 3.68-3.74 (m, 4 H) 5.44 (s, 2 H) 7.61 (d, J = 8.34 Hz, 2 H) 7.85 (d, J = 8.34 Hz, 2 H) 8.80 (s, 1 H); LC/MS: MS (ES+) m/e 354 (MH+). |
| 29 | 4-(trifluoromethoxy)benzyl group | 2-(4-morpholinyl)-4-({4-[(trifluoromethyl)oxy]phenyl}methyl)[1,3]thiazolo[4,5-d]pyrimidin-7(4H)-one | $^1$H NMR (400 MHz, DMSO-$d_6$) δ ppm 3.59 (br. s., 4 H) 3.76 (m, 4 H) 5.36 (s, 2 H) 7.37 (d, J = 7.83 Hz, 2 H) 7.57 (d, J = 8.84 Hz, 2 H) 8.64 (s, 1 H); LC/MS: MS (ES+) m/e 413 (MH+). |
| 30 | methyl 3-methylthiophene-2-carboxylate group | methyl 3-{[2-(4-morpholinyl)-7-oxo[1,3]thiazolo[4,5-d]pyrimidin-4(7H)-yl]methyl}-2-thiophenecarboxylate | LCMS (ES) m/z = 393.0 (M + H); $^1$H NMR (400 MHz, METHANOL-d4) δ ppm 8.91 (s, 1H), 7.53 (d, J = 4.8 Hz, 1H), 7.13 (d, J = 4.8 Hz, 1H), 5.82 (s, 2H), 3.95 (s, 3H), 3.89-3.78 (m, 4H), 3.80-3.68 (m, 4H). |
| 31 | 3-pyridinylmethyl group | 2-(4-morpholinyl)-4-(3-pyridinylmethyl)[1,3]thiazolo[4,5-d]pyrimidin-7(4H)-one | LCMS (ES) m/z = 410.8 (M + H); 1H NMR (400 MHz, DMSO) δ ppm 8.74-8.70 (m, 1H), 8.61 (s, 1H), 8.54-8.50 (m, 1H), 7.86-7.83 (m, 1H), 7.42-7.38 (m, 1H), 5.36 (s, 2H), 3.75-3.70 (m, 4H), 3.62-3.57 (m, 4H). |
| 32 | 2-fluoro-3-methylbenzyl group | 4-[(2-fluoro-3-methylphenyl)methyl]-2-(4-morpholinyl)[1,3]thiazolo[4,5-d]pyrimidin-7(4H)-one | LCMS (ES) m/z = 361.0 (M + H); $^1$H NMR (400 MHz, METHANOL-d4) δ ppm 8.16 (s, 1H), 7.21-7.17 (m, 2H), 7.05-7.03 (m, 1H), 5.32 (s, 2H), 3.87-3.85 (m, 4H), 3.67-3.65 (m, 4H), 2.31 (s, 3H). |

-continued

Table of Spectra Data

| Example | R | Name | Data |
|---|---|---|---|
| 33 | 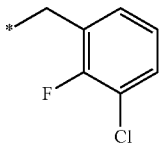 | 4-[(3-chloro-2-fluorophenyl)methyl]-2-(4-morpholinyl)[1,3]thiazolo[4,5-d]pyrimidin-7(4H)-one | LCMS (ES) m/z = 381.0 (M + H); $^1$H NMR (400 MHz, METHANOL-d4) δ ppm 8.19 (s, 1H), 7.45-7.41 (m, 1H), 7.23-7.19 (m, 1H), 7.12-7.08 (m, 1H), 5.34 (s, 2H), 3.87-3.85 (m, 4H), 3.66-3.63 (m, 4H). |
| 34 | 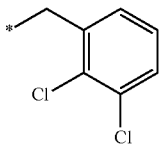 | 4-[(2,3-dichlorophenyl)methyl]-2-(4-morpholinyl)[1,3]thiazolo[4,5-d]pyrimidin-7(4H)-one | LC/MS (ES$^+$) m/e 397 (MH$^+$); $^1$H NMR (400 MHz, DMSO-d$_6$) δ ppm 3.50-3.58 (m, 4 H) 3.68 (m, 4 H) 5.48 (s, 2 H) 7.19 (d, J = 7.8 Hz, 1 H) 7.36 (m, 1 H) 7.64 (d, J = 8.1 Hz, 1 H) 8.61 (s, 1 H); |
| 35 | 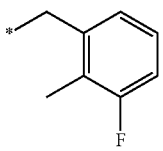 | 4-[(3-fluoro-2-methylphenyl)methyl]-2-(4-morpholinyl)[1,3]thiazolo[4,5-d]pyrimidin-7(4H)-one | LCMS (ES) m/z 361.0 (M + H)$^+$, $^1$H NMR (400 MHz, CDCl$_3$-d1) δ ppm 7.98 (s, 1H), 7.18 (m, 1H), 7.06 (m, 1H), 6.86 (m, 1H), 5.32 (s, 2H), 3.83 (m, 4H), 3.63 (m, 4H) |
| 36 | 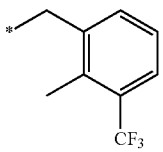 | 4-{[2-methyl-3-(trifluoromethyl)phenyl]methyl}2-(4-morpholinyl)[1,3]thiazolo[4,5-d]pyrimidin-7(4H)-one | LCMS (ES) m/z 411.0 (M + H)$^+$, $^1$H NMR (400 MHz, CDCl$_3$-d1)) δ ppm 8.00 (s, 1H), 7.67 (m, 1H), 7.31 (m, 1H), 7.19 (m, 2H), 5.37 (s, 2H), 3.82 (m, 4H), 3.61 (m, 4H), 2.50 (s, 3H) |
| 37 | 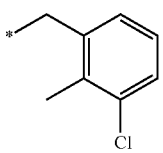 | 4-[(3-chloro-2-methylphenyl)methyl]-2-(4-morpholinyl)[1,3]thiazolo[4,5-d]pyrimidin-7(4H)-one | LCMS (ES) m/z 377.0 (M + H)$^+$, $^1$H NMR (400 MHz, CDCl$_3$- d1) δ ppm 8.31 (br, s, 1H), 7.43 (m, 1H), 7.17 (m, 1H), 6.97 (m, 1H), 5.44 (s, 2H), 3.85 (m, 4H), 3.67 (m, 4H), 2.43 (s, 3H) |
| 38 | 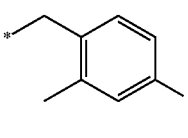 | 4-[(4-fluoro-2-methylphenyl)methyl]-2-(4-morpholinyl)[1,3]thiazolo[4,5-d]pyrimidin-7(4H)-one | LCMS (ES) m/z 361.0 (M + H)$^+$, $^1$H NMR (400 MHz, CDCl$_3$- d1) δ ppm 7.97 (s, 1H), 7.10 (m, 1H). 6.89-6.98 (m, 2H), 5.27 (s, 2H), 3.84 (m, 4H), 3.63 (m, 4H), 2.36 (s, 3H) |
| 39 | 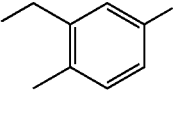 | 4-[(5-fluoro-2-methylphenyl)methyl]-2-(4-morpholinyl)[1,3]thiazolo[4,5-d]pyrimidin-7(4H)-one | LCMS (ES) m/z 361.0 (M + H)$^+$, $^1$H NMR (400 MHz, CDCl$_3$- d1) δ ppm 8.00 (s, 1H), 7.20 (m, 1H), 6.96 (m, 1H), 6.80 (m, 1H), 5.27 (s, 2H), 3.83 (m, 4H), 3.63 (m, 4H), 2.35 (s, 3H) |
| 40 | 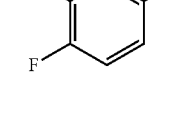 | 4-[(2-fluoro-5-methylphenyl)methyl]-2-(4-morpholinyl)[1,3]thiazolo[4,5-d]pyrimidin-7(4H)-one | LCMS (ES) m/z 361.1 (M + H)$^+$, $^1$H NMR (400 MHz, CDCl$_3$-d1) δ ppm 8.62 (br s, 1H), 7.16 (m, 2H), 7.00 (m, 1H), 5.42 (s, 2H), 3.86 (m, 4H), 3.71 (m, 4H), 2.32 (s, 3H) |
| 41 | 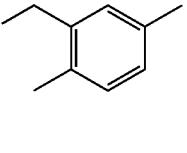 | 4-[(2,5-dimethylphenyl)methyl]-2-(4-morpholinyl)[1,3]thiazolo[4,5-d]pyrimidin-7(4H)-one | LCMS (ES) m/z 357.1 (M + H)$^+$, $^1$H NMR (400 MHz, CDCl$_3$-d1) δ ppm 8.50 (br, s, 1H), 7.13 (m, 2H), 6.95 (s, 1H), 5.46 (s, 2H), 3.86 (m, 4H), 3.70 (m, 4H), 2.33 (s, 3H), 2.31 (s, 3H) |
| 42 | 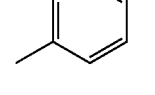 | 4-{[2-methyl-5-(trifluoromethyl)phenyl]methyl}-2-(4-morpholinyl)[1,3]thiazolo[4,5-d]pyrimidin-7(4H)-one | LCMS (ES) m/z 411.0 (M + H)$^+$, $^1$H NMR (400 MHz, CDCl$_3$-d1) δ ppm 8.18 (br, s, 1H), 7.56 (m, 2H), 7.37 (m, 1H), 5.34 (s, 2H), 3.83 (m, 4H), 3.62 (m, 4H) |

-continued

Table of Spectra Data

| Example | R | Name | Data |
|---|---|---|---|
| 43 | 2-chloro-5-(trifluoromethyl)benzyl (Cl, CF3) | 4-{[2-chloro-5-(trifluoromethyl)phenyl]methyl}-2-(4-morpholinyl)[1,3]thiazolo[4,5-d]pyrimidin-7(4H)-one | LCMS (ES) m/z 431.0 (M + H)+, $^1$H NMR (400 MHz, CDCl$_3$-d1) δ ppm 8.70 (br, s, 1H), 7.95 (s, 1H), 7.58~7.64 (m, 2H). 5.52 (s, 2H), 3.85 (m, 4H), 3.67 (m, 4H) |
| 44 | 2-chloro-5-fluorobenzyl (Cl, F) | 4-[(2-chloro-5-fluorophenyl)methyl]-2-(4morpholinyl)[1,3]thiazolo[4,5d]pyrimidin-7(4H)-one | LCMS (ES) m/z 381.0 (M + H)+, $^1$H NMR (400 MHz, CDCl$_3$-d1) δ ppm 8.20 (s, 1H), 7.42 (m, 1H), 7.00~7.07 (m, 2H), 5.37 (s, 2H), 3.84 (m, 4H), 3.64 (m, 4H) |
| 45 | 2-fluoro-5-(trifluoromethyl)benzyl (F, CF3) | 4-{[2-fluoro-5-(trifluoromethyl)phenyl]methyl}-2-(4-morpholinyl)[1,3]thiazolo[4,5-d]pyrimidin-7(4H)-one | LCMS (ES) m/z = 415.0 (M + H); $^1$H NMR (400 MHz, METHANOL-d4) δ ppm 9.04 (s, 1H), 7.94-7.91 (m, 1H), 7.72-7.68 (m, 1H), 7.30-7.25 (m, 1H), 5.53 (s, 2H), 3.88-3.85 (m, 4H), 3.80-3.65 (m, 4H). |
| 46 | 5-chloro-2-fluorobenzyl (Cl, F) | 4-[(5-chloro-2-fluorophenyl)methyl]-2-(4-morpholinyl)[1,3]thiazolo[4,5-d]pyrimidin-7(4H)-one | LC/MS (ES+) m/e 381 (MH+); $^1$H NMR (400 MHz, DMSO-d$_6$) δ ppm 3.59 (m, 4H) 3.71 (m, 4 H) 5.37 (s, 2H) 7.30 (m, 1H) 7.47 (m, 1H) 7.62 (m, 1 H) 8.65 (s, 1H) |
| 47 | 2,5-dichlorobenzyl (Cl, Cl) | 4-[(2,5-dichlorophenyl)methyl]-2-(4-morpholinyl)[1,3]thiazolo[4,5-d]pyrimidin-7(4H)-one | LC/MS (ES+) m/e 397 (MH+); $^1$H NMR (400 MHz, DMSO-d$_6$) δ ppm 3.56 (m, 4H) 3.67-3.72 (m, 4H) 5.41 (s, 2H) 7.43-7.49 (m, 1H) 7.52 (d, J = 2.5 Hz, 1H) 7.53-7.56 (m, 1H) 8.61 (s, 1H) |
| 48 | 3,4-dichlorobenzyl (Cl, Cl) | 4-[(3,4-dichlorophenyl)methyl]-2-(4-morpholinyl)[1,3]thiazolo[4,5-d]pyrimidin-7(4H)-one | LC/MS (ES+) m/e 397 (MH+); $^1$H NMR (400 MHz, DMSO-d$_6$) δ ppm 3.60 (m, 4 H) 3.69-3.76 (m, 4H) 5.32 (s, 2H) 7.44 (dd, J = 8.3 , 2.0 Hz, 1H) 7.64 (d, J = 8.3 Hz, 1H) 7.81 (d, J = 2.0 Hz, 1H) 8.70 (s, 1H); |
| 49 | 3-chloro-4-fluorobenzyl (Cl, F) | 4-[(3-chloro-4-fluorophenyl)methyl]-2-(4-morpholinyl)[1,3]thiazolo[4,5-d]pyrimidin-7(4H)-one | LC/MS (ES+) m/e 381 (MH+); $^1$H NMR (400 MHz, DMSO-d$_6$) δ ppm 3.62 (m, 4H) 3.70-3.77 (m, 4H) 5.32 (s, 2H) 7.42 (m, 1H) 7.48-7.54 (m, 1H) 7.79 (dd, J = 7.2, 2.2 Hz, 1H) 8.75 (s, 1 H) |
| 50 | 2,3,4-trifluorobenzyl (F, F, F) | 2-(4-morpholinyl)-4-[(2,3,4-trifluorophenyl)methyl][1,3]thiazolo[4,5-d]pyrimidin-7(4H)-one | LCMS (ES) m/z 383.0 (M + H)+, $^1$H NMR (400 MHz, CDCl$_3$-d1)) δ ppm 8.20 (s, 1H), 7.08 (m, 1H), 6.98 (m, 1H), 5.31 (s, 2H), 3.85 (m, 4H), 3.64 (m, 4H) |
| 51 | 2,4-difluoro-3-chlorobenzyl (F, Cl, F) | 4-{[2,4-difluoro-3-(methyloxy)phenyl]methyl}-2-(4-morpholinyl)[1,3]thiazolo[4,5-d]pyrimidin-7(4H)-one | LCMS (ES) m/z 399.0 (M + H)+, $^1$H NMR (400 MHz, CDCl$_3$-d1)) δ ppm 8.19 (s, 1H), 7.25 (m, 1H), 7.01 (m, 1H), 5.31 (s, 2H), 3.85 (m, 4H), 3.65 (m, 4H) |
| 52 | 2,4-difluoro-3-methoxybenzyl (F, OMe, F) | 4-{[2,4-difluoro-3-(methyloxy)phenyl]methyl}-2-(4-morpholinyl)[1,3]thiazolo[4,5-d]pyrimidin-7(4H)-one | LCMS (ES) m/z 395.0 (M + H)+, $^1$H NMR (400 MHz, CDCl$_3$-d1)) δ ppm 8.18 (s, 1H), 6.98 (m, 1H), 6.88 (m, 1H), 5.28 (s, 2H), 4.03 (m, 3H), 3.85 (m, 4H), 3.65 (m, 4H) |

| Example | R | Name | Data |
|---|---|---|---|
| 53 | 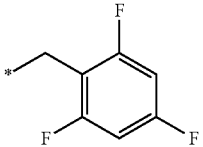 | 2-(4-morpholinyl)-4-[(2,4,6-trifluorophenyl)methyl][1,3]thiazolo[4,5-d]pyrimidin-7(4H)-one | LCMS (ES) m/z 383.0 (M + H)+, 1H NMR (400 MHz, CDCl3-d1) δ ppm 8.21 (s, 1H), 6.74 (m, 2H), 5.28 (s, 2H), 3.84 (m, 4H), 3.64 (m, 4H) |
| 54 | 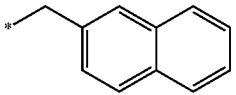 | 2-(4-morpholinyl)-4-(2-naphthalenylmethyl)[1,3]thiazolo[4,5-d]pyrimidin-7(4H)-one | LCMS (ES) m/z = 379.1 (M + H); 1H NMR (400 MHz, METHANOL-d4) δ ppm 8.19 (s, 1H), 7.88-7.80 (m, 3H), 7.72 (s, 1H), 7.55-7.52 (m, 2H), 7.41-7.38 (m, 1H), 5.46 (s, 2H), 3.84-3.81 (m, 4H), 3.65-3.62 (m, 4H). |
| 55 | 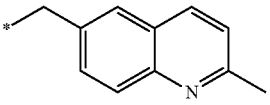 | 4-{[2,4-difluoro-3-(methyloxy)phenyl]methyl}-2-(4-morpholinyl)[1,3]thiazolo[4,5-d]pyrimidin-7(4H)-one | LCMS (ES) m/z 399.0 (M + H)+, 1H NMR (400 MHz, CDCl3-d1) δ ppm 8.19 (s, 1H), 7.25 (m, 1H), 7.01 (m, 1H), 5.31 (s, 2H), 3.85 (m, 4H), 3.65 (m, 4H) |
| 56 | 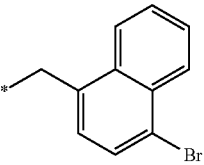 | 4-[(4-bromo-1-naphthalenyl)methyl]-2-(4-morpholinyl)[1,3]thiazolo[4,5-d]pyrimidin-7(4H)-one | LCMS (ES) m/z 459.0 (M + H)+, 1H NMR (400 MHz, CDCl3-d1) δ ppm 8.38 (m, 1H), 7.98 (m, 2H), 7.71 (m, 1H), 7.63~7.68 (m, 2H), 7.10 (m, 1H), 5.76 (s, 2H), 3.82 (m, 4H), 3.62 (m, 4H) |
| 57 | 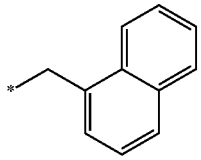 | 2-(4-morpholinyl)-4-(1-naphthalenylmethyl)[1,3]thiazolo[4,5-d]pyrimidin-7(4H)-one | LCMS (ES) m/z 379.0 (M + H)+, 1H NMR (400 MHz, CDCl3-d1)) δ ppm 7.908.00 (m, 4H), 7.567.60 (m, 2H), 7.48 (m, 1H), 7.31 (m, 1H), 5.79 (s, 2H), 3.84 (m, 4H), 3.65 (m, 4H) |
| 58 | 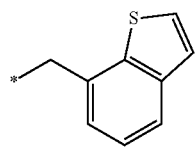 | 4-(1-benzothien-7-ylmethyl)-2-(4-morpholinyl)[1,3]thiazolo[4,5-d]pyrimidin-7(4H)-one | LCMS (ES) m/z 385.0 (M + H)+, 1H NMR (400 MHz, CDCl3-d1) δ ppm 8.17 (s, 1H), 7.85 (m, 1H), 7.49 (m, 1H), 7.40 (m, 2H), 7.23 (m, 1H), 5.56 (s, 2H), 3.81 (m, 4H), 3.62 (m, 4H) |

Scheme 7. Preparation of Example 59

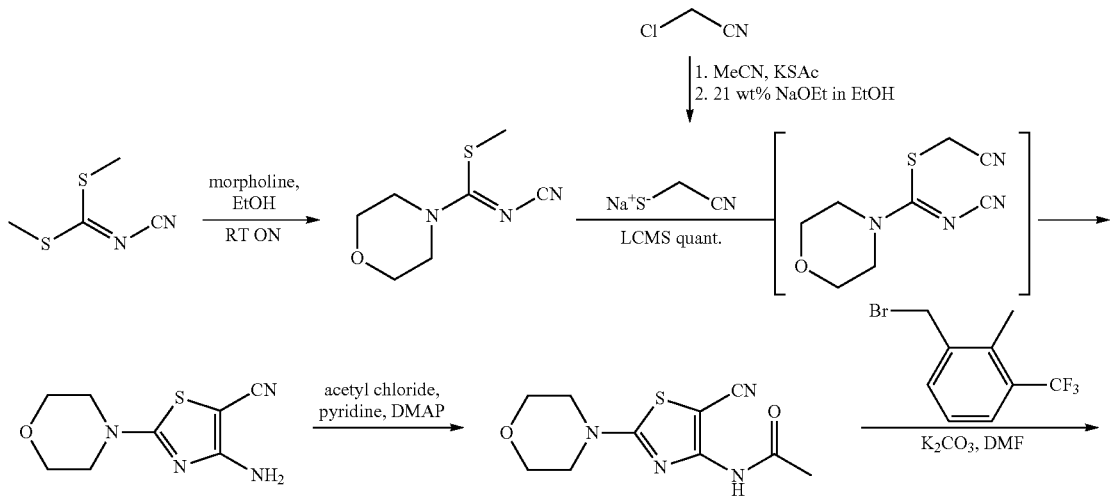

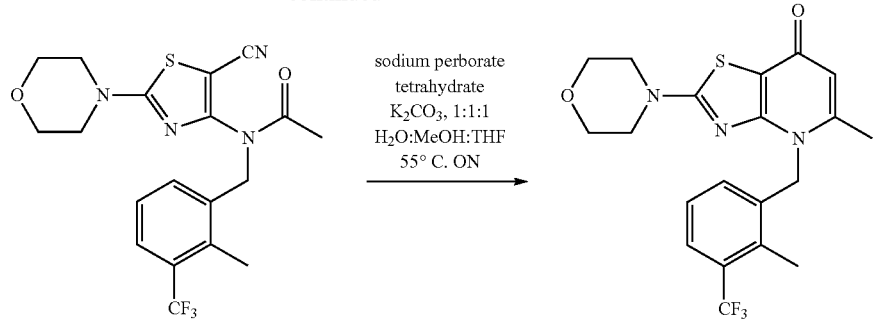

Preparation of 5-methyl-4-{[2-methyl-3-(trifluoromethyl)phenyl]methyl}-2-(4-morpholinyl)[1,3]thiazolo[4,5-d]pyrimidin-7(4H)-one a) methyl N-cyano-4-morpholinecarbimidothioate

A 3 L round bottom flask equipped with a mechanical stirrer was charged with dimethyl cyanodithioimidocarbonate (200 g, 1368 mmol). The solid material was taken up in Ethanol (2279 ml) and stirred until completely dissolved. Morpholine (119 ml, 1368 mmol) was then added to the flask by graduated cylinder and the mechanical stirrer set to a vigorous rate for overnight stirring of the resulting mixture at room temperature. The resulting white precipitate was collected and dried via suction filtration overnight to afford pure white solid methyl N-cyano-4-morpholinecarbimidothioate (212.5 g, 1147 mmol, 84% yield) as a white solid ($^1$H NMR (400 MHz, DMSO-$d_6$) δ ppm 2.70 (s, 3H) 3.61-3.66 (m, 4H) 3.74-3.79 (m, 4H)).

b) 4-amino-2-(4-morpholinyl)-1,3-thiazole-5-carbonitrile

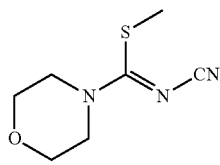

To a 2 L erlenmeyer flask equipped with a mechanical stirrer was added potassium thioacetate (123 g, 1080 mmol). The solid was taken up in Acetonitrile (864 ml) and to that suspension was added chloroacetonitrile (68.3 ml, 1080 mmol). Caution: reaction generates significant exotherm on scale and will boil the acetonitrile if the ClCH$_2$CN is added too fast. The resulting reaction mixture was stirred overnight at room temperature, allowing it to cool to room temperature from it's initial exotherm. The reaction solution was then filtered to remove the majority of the KCl formed in the initial reaction into a 4 L filter flask. The resulting dark orange transparent solution was then transferred to a 3 L round bottom flask for the next step.

The solution was treated with a 21 wt % ethanolic solution of sodium ethoxide (403 ml, 1080 mmol) (in four (4) portions by graduated cylinder) and stirred with a magnetic stirrer at room temperature for 1 hour. The magnetic stir bar was then removed and solid methyl N-cyano-4-morpholinecarbimidothioate (200 g, 1080 mmol) was added to the suspension. The reaction was fitted with a mechanical stirrer and stirred overnight at room temperature. Upon complete conversion to the desired material by LCMS, the reaction was swamped with 0.5N NaOH (poured in ~1,5-2 L) and stirred mechanically for an additional 30 minutes to afford a fine precipitate. The precipitate was the collected via suction filtration and washed with 2 L of EtOH to afford 4-amino-2-(4-morpholinyl)-1,3-thiazole-5-carbonitrile (116.5 g, 554 mmol, 51.3% yield) as a pale cream colored solid $^1$H NMR (400 MHz, DMSO-$d_6$) δ ppm 3.38-3.42 (m, 4H) 3.64-3.69 (m, 4H) 6.82 (s, 2H).

c) N-[5-cyano-2-(4-morpholinyl)-1,3-thiazol-4-yl]acetamide

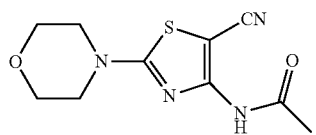 [SMILES: CC(=O)Nc1nc(N2CCOCC2)sc1C#N]

To a 5 L round bottom flask equipped with a mechanical stirrer was added 4-amino-2-(4-morpholinyl)-1,3-thiazole-5-carbonitrile (200 g, 951 mmol) and N,N-dimethylaminopyridine (23.24 g, 190 mmol). The solids were taken up in Pyridine (2000 mL) and to this reaction solution was added acetyl chloride (74.7 g, 951 mmol) via an addition funnel. The reaction was heated to 80° C. and monitored by LCMS for conversion to product. Upon complete conversion (~2 hours), the reaction was cooled to room temperature and the reaction was concentrated to a slurry, then subsequently diluted with a mixture of 0.1N NaOH (2 L) solution and methanol (140 mL). The mixture was rapidly stirred using a mechanical stirrer for 15 min, then the resulting precipitate was collected by filtration to provide the desired N-[5-cyano-2-(4-morpholinyl)-1,3-thiazol-4-yl]acetamide (218.2 g, 778 mmol, 82% yield) as a brown solid ($^1$H NMR (400 MHz, DMSO-$d_6$) δ ppm 2.04 (s, 3H) 3.40-3.53 (m, 4H) 3.62-3.77 (m, 4H) 10.88 (s, 1H)).

d) N-[5-cyano-2-(4-morpholinyl)-1,3-thiazol-4-yl]-N-{[2-methyl-3-(trifluoromethyl)phenyl]methyl}acetamide

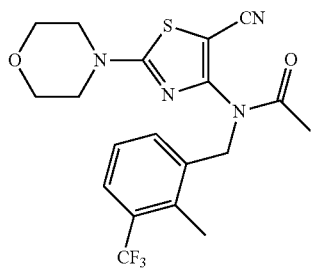 [SMILES: CC(=O)N(Cc1cccc(C(F)(F)F)c1C)c1nc(N2CCOCC2)sc1C#N]

To a 1 L round bottom flask containing a stirred suspension of N-[5-cyano-2-(4-morpholinyl)-1,3-thiazol-4-yl]acetamide (20.0 g, 79 mmol) and $K_2CO_3$ (23.01 g, 166 mmol) in N,N-Dimethylformamide (DMF) (250 mL) was added 11-(bromomethyl)-2-methyl-3-(trifluoromethyl)benzene (20.06 g, 79 mmol). The reaction was heated to 90° C. and was maintained at 90° C. for 3 hr. LC/MS at this point indicated predominantly product, so the reaction was cooled to room temperature, partitioned between water (500 mL) and ethyl acetate (500 mL). The layers were separated, and then the aqueous layer was extracted with ethyl acetate (3×100 mL). The combined organic layers were dried over sodium sulfate, then concentrated to leave N-[5-cyano-2-(4-morpholinyl)-1,3-thiazol-4-yl]-N-{[2-methyl-3-(trifluoromethyl)phenyl]methyl}acetamide (27.1 g, 63.8 mmol, 81% yield) as a residual oil that was carried onto the next step without further purification. $^1$H NMR (400 MHz, DMSO-$d_6$) δ ppm 2.11 (s, 3H) 2.36 (s, 3H) 3.43-3.52 (m, 4H) 3.64-3.74 (m, 4H) 4.99 (s, 2H) 7.33 (t, J=7.83 Hz, 1H) 7.43 (d, J=7.58 Hz, 1H) 7.60 (d, J=7.83 Hz, 1H)

e) 5-methyl-4-{[2-methyl-3-(trifluoromethyl)phenyl]methyl}-2-(4-morpholinyl)[1,3]thiazolo[4,5-d]pyrimidin-7(4H)-one In a 2 L round bottom flask equipped with a magnetic stir bar, N-[5-cyano-2-(4-morpholinyl)-1,3-thiazol-4-yl]-N-{[2-methyl-3-(trifluoromethyl)phenyl]methyl}acetamide (42.5 g, 100 mmol), sodium perborate tetrahydrate (46.2 g, 300 mmol), and potassium carbonate (27.64 g, 200 mmol) were taken up in Methanol (233 mL), Tetrahydrofuran (THF) (233 mL), and Water (233 mL) and the resulting reaction mixture was heated to 55° C. and stirred overnight at 55° C.

The reaction was monitored by LC/MS, which indicated that the product predominated and consumption of starting material. The reaction solution was cooled to room temperature, partitioned between ethyl acetate (700 mL) and water (700 mL), and then was extracted. The aqueous phase was re-extracted with additional ethyl acetate (500 mL), and then the combined organic layers were concentrated in vacuo. This material was chromatographed on ~1 kg silica gel eluted with $CHCl_3$/(2M $NH_3$ in methanol) [100% $CHCl_3$ to 95:5] to provide 3 fractions: 98-B1-1 (8.0 g) and 98-B1-2 (16.3 g) and 98-B1-3 (1.0 g). Fractions 98-BI-2 and 98-B1-3 required additional purification by Prep HPLC using the conditions listed below:

Luna $C_{18}$(2) 10u 101×250 mm

A=300 mM Aqueous ammonium formate (pH 4)

B=acetonitrile

55:45-A:B 400 ml/min uv 254 nm

Purification and workup provided 13.6 g of an off white solid with HPLC purity of 99.2%.

1H NMR (400 MHz, DMSO-$d_6$) δ ppm 2.31 (s, 3H) 2.49 (s, 3H) 3.38-3.58 (m, 4H) 3.58-3.85 (m, 4H) 5.56 (s, 2H) 6.84 (d, J=7.83 Hz, 1H) 7.35 (t, J=7.96 Hz, 1H) 7.63 (d, J=7.83 Hz, 1H).

Recrystallization of Combined Batches: (to Provide 1 Batch of Uniform Particles):

Several lots totaling 41.6 g were combined in $CHCl_3$ (200 mL) and ethanol (1.2 L) in a 3 L round bottom flask. The solution was stripped to remove most of the $CHCl_3$, then heated at 60° C. whereupon the material fell out of solution (note: the material fell out of solution faster than the previous crystallization attempt and the crystals looked more powdery compared to previous crystallization attempts). The mixture was stirred at 60° C. on rotary evaporator for 30 min, then cooled, filtered and isolated the solid. Provided 33.6 g of 5-methyl-4-{[2-methyl-3-(trifluoromethyl)phenyl]methyl}-2-(4-morpholinyl)[1,3]thiazolo[4,5-d]pyrimidin-7(4H)-one, as a solid with a yellow tinge after drying to constant weight. Examination under microscope indicated that the material was crystalline.

The following compounds in the table were prepared according to the procedures of Example 7.

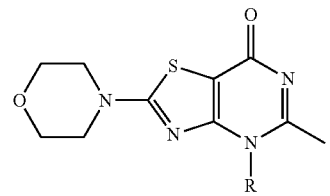

Table of Spectra Data

| Example | R | Name | Data |
|---|---|---|---|
| 60 | 2-methyl-3-chlorobenzyl | 4-[(3-chloro-2-methylphenyl)methyl]-5-methyl-2-(4-morpholinyl)[1,3]thiazolo[4,5-d]pyrimidin-7(4H)-one | LCMS (ES) m/z 391.1 (M + H)⁺, $^1$H NMR (400 MHz, CDCl$_3$-d1) δ ppm 7.38 (m, 1H), 7.11 (m, 1H), 6.46 (m, 1H), 5.58 (s, 2H), 3.82 (m, 4H), 3.62 (m, 4H), 2.57 (s, 3H), 2.49 (s, 3H) |
| 61 | 3,4-dichlorobenzyl | 4-[(3,4-dichlorophenyl)methyl]-5-methyl-2-(4-morpholinyl)[1,3]thiazolo[4,5-d]pyrimidin-7(4H)-one | 1H NMR (400 MHz, DMSO-d$_6$) δ ppm 2.51 (s, 3 H) 3.60 (br. s., 4 H) 3.68-3.78 (m, 4 H) 5.55 (s, 2 H) 7.26 (dd, J = 8.3, 2.27 Hz, 1 H) 7.64 (d, J = 8.3 Hz, 1 H) 7.66 (d, J = 2.0 Hz, 1 H); LC/MS: MS (ES⁺) m/e 411 (MH⁺). |
| 62 | 1-naphthylmethyl | 5-methyl-2-(4-morpholinyl)-4-(1-naphthalenylmethyl)[1,3]thiazolo[4,5-d]pyrimidin-7(4H)-one | LCMS (ES) m/z 393.2 (M + H)⁺, $^1$H NMR (400 MHz, CDCl$_3$-d1) δ ppm 8.00 (m, 2H), 7.88 (m, 1H), 7.70 (m, 2H), 7.43 (m, 1H), 6.76 (m, 1H), 6.10 (s, 2H), 3.76 (m, 4H), 3.58 (m, 4H), 2.63 (s, 3H) |
| 63 | 2-naphthylmethyl | 5-methyl-2-(4-morpholinyl)-4-(2-naphthalenylmethyl)[1,3]thiazolo[4,5-d]pyrimidin-7(4H)-one | LCMS (ES) m/z 393.2 (M + H)⁺, $^1$H NMR (400 MHz, CDCl$_3$-d1) δ ppm 7.80~7.90 (m, 3H), 7.52~7.56 (m, 3H), 7.31 (m, 1H), 5.81 (s, 2H), 3.83 (m, 4H), 3.67 (m, 4H), 2.75 (s, 3H) |

The following compounds in the table were prepared according to the procedures of Example 8, method A.

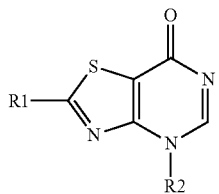

35

40

Table of Spectra Data

| Example | R1 | R2 | Name | Data |
|---|---|---|---|---|
| 64 | cis-2,6-dimethylmorpholinyl | 2-methylbenzyl | 2-(2,6-dimethyl-4-morpholinyl)-4-[(2-methylphenyl)methyl][1,3]thiazolo[4,5-d]pyrimidin-7(4H)-one | $^1$H NMR (300 MHz, CDCl$_3$) δ ppm 7.93 (s, 1H), 7.29-7.06 (m, 4H), 5.30 (s, 2H), 3.90-3.66 (m, 4H), 2.87 (t, 2H, J = 10.2 Hz), 2.35 (s, 3H), 1.27 (d, 6H, J = 6.0 Hz). LCMS (ES) m/z 371.1 (M + H)⁺ |
| 65 | 2,2-dimethylmorpholinyl | 2,3-dichlorobenzyl | 2-(2,6-dimethyl-4-morpholinyl)-4-[(2-methylphenyl)methyl][1,3]thiazolo[4,5-d]pyrimidin-7(4H)-one | $^1$H NMR (300 MHz, d$_6$-DMSO) δ ppm 8.31 (s, 1 H), 7.64 (dd, J = 7.8, 1.2 Hz, 1 H), 7.39 (m, 1 H), 7.22 (d, J = 7.8 Hz, 1 H), 5.47 (s, 2 H), 3.71 (t, J = 4.8 Hz, 2 H), 3.51 (s, br, 2 H), 3.43 (s, 2 H),1.12 (s, 6 H); LC-MS: 425 (MH⁺). |

Table of Spectra Data

| Example | R1 | R2 | Name | Data |
|---|---|---|---|---|
| 66 | 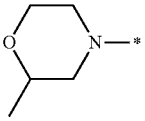 | 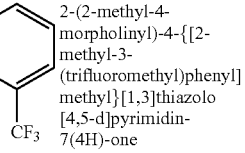 | 2-(2-methyl-4-morpholinyl)-4-{[2-methyl-3-(trifluoromethyl)phenyl]methyl}[1,3]thiazolo[4,5-d]pyrimidin-7(4H)-one | $^1$H NMR (300 MHz, d6-DMSO) δ ppm 8.51 (s, 1 H), 7.63 (d, J = 7.5 Hz, 1 H), 7.35 (m, 1 H), 7.24 (d, J = 7.5 Hz, 1 H), 5.44 (s, 2 H), 3.87 (dd, J = 11.7, 2.7 Hz, 1 H), 3.76 (br, 2 H), 3.57~3.47 (m, 2 H), 3.20 (t, J = 11.7 Hz, 1 H), 2.89 (t, J = 11.7 Hz, 1 H), 2.56 (s, 3 H), 1.10 (t, J = 6.3 Hz, 3 H); LC-MS: 425 (MH$^+$);. |

The following compounds in the table were prepared according to the procedures of Example 8, method B.

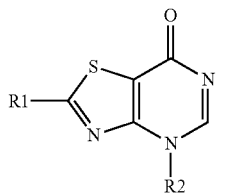

20

25

Table of Spectra Data

| Example | R1 | R2 | Name | Data |
|---|---|---|---|---|
| 67 | 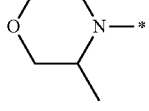 | 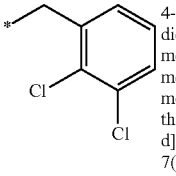 | 4-[(2,3-dichlorophenyl)methyl]-2-(3-methyl-4-morpholinyl)[1,3]thiazolo[4,5-d]pyrimidin-7(4H)-one | $^1$H NMR (300 MHz, CDCl$_3$) δ 8.35 (s, 1 H), 7.48 (d, J = 7.5 Hz, 1 H), 7.23~7.13 (m, 2 H), 5.47 (s, 2 H), 4.08~3.99 (m, 2 H), 3.81~3.48 (m, 5 H), 1.35 (d, J = 6.9 Hz, 3 H); LC-MS: 411 (MH$^+$) |
| 68 | 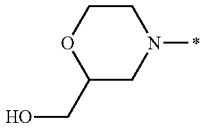 | 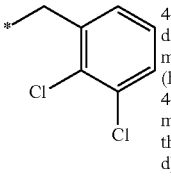 | 4-[(2,3-dichlorophenyl)methyl]-2-[2-(hydroxymethyl)-4-morpholinyl][1,3]thiazolo[4,5-d]pyrimidin-7(4H)-one | $^1$H NMR (300 MHz, d$_6$-DMSO) δ ppm 8.46 (s, 1 H), 7.61 (d, J = 7.8 Hz, 1 H), 7.33 (m, 1 H), 7.16 (d, J = 7.2 Hz, 1 H), 5.44 (s, 2 H), 4.87 (m, 1 H), 3.92~3.52 (m, 3 H), 3.52~3.37 (m, 4 H), 3.24~3.02 (m, 2 H); $^1$H NMR (300 MHz, d$_6$-DMSO + D$_2$O) δ ppm 8.47 (s, 1 H), 7.62 (d, J = 8.1 Hz, 1 H), 7.35 (m, 1 H), 7.19 (d, J = 7.5 Hz, 1 H), 5.46 (s, 2 H), 3.94~3.78 (m, 3 H), 3.57~3.40 (m, 4 H), 3.24 (t, J = 10.9 Hz, 1 H), 3.08~3.00 (m, 1 H); LC-MS: 427 (MH$^+$). |
| 69 | 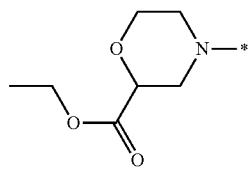 | 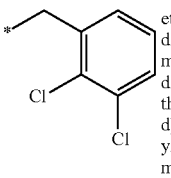 | ethyl 4-{4-[(2,3-dichlorophenyl)methyl]-7-oxo-4,7-dihydro[1,3]thiazolo[4,5-d]pyrimidin-2-yl}-2-morpholinecarboxylate | $^1$H NMR (300 MHz, CDCl$_3$) δ ppm 8.41 (s, 1 H), 7.48 (d, J = 7.5 Hz, 1 H), 7.22~7.16 (m, 2 H), 5.50 (s, 2 H), 4.30 (q, J = 7.2 Hz, 2 H), 4.24~4.14 (m, 3 H), 3.80~3.73 (m, 2 H), 3.53~3.47 (m, 2 H), 1.34 (t, J = 7.2 Hz, 3 H); LC-MS: 469 (MH$^+$). |

Scheme 8. Preparation of Example 70 (Method A)

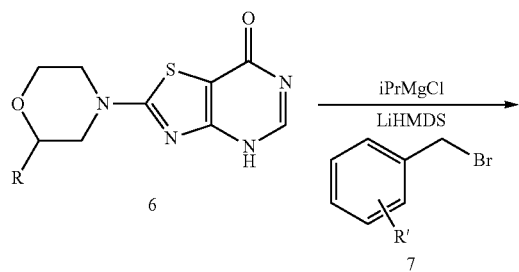

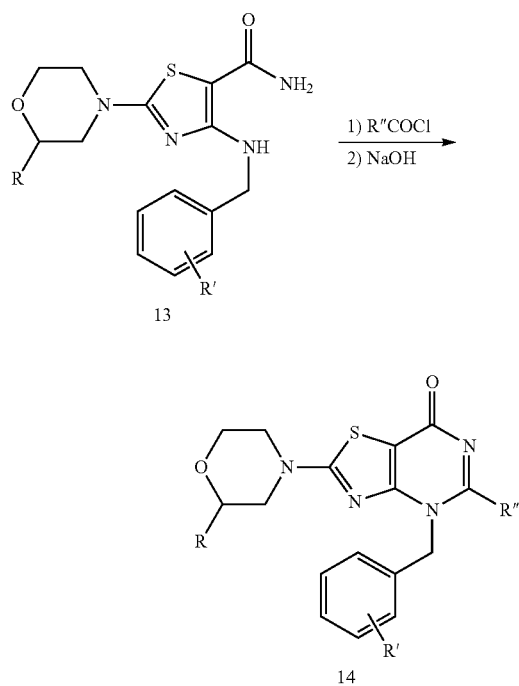

The regioselective N-alkylation of thiazolopyrimidinone 6 is carried out under the condition of 1 eq. of isopropylmagnesium chloride (iPrMgCl) followed by 2 eq. of lithium bis(trimethylsilyl)amide (LiHMDS) in anhydrous tetrahydrofuran (THF) at 0° C. Addition of a substituted benzyl bromide 7 affords the desired product 8a, which is hydrolyzed with aq. NaOH to form amide 13. Treatment of crude 13 with various acyl chloride followed by in situ ring closure with or without assistance of base provides final product thiazolopyrimidinones 14.

Example 70

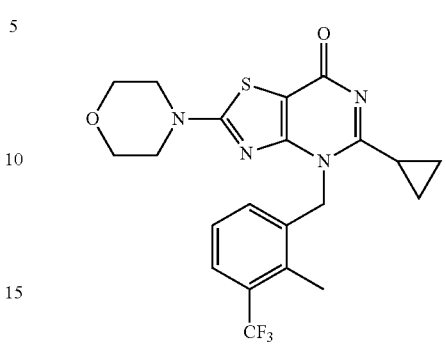

Preparation of 5-cyclopropyl-4-{[2-methyl-3-(trifluoromethyl)phenyl]methyl}-2-(4-morpholinyl)[1,3]thiazolo[4,5-d]pyrimidin-7(4H)-one (Method A)

a) 4-({[2-methyl-3-(trifluoromethyl)phenyl]methyl}amino)-2-(4-morpholinyl)-1,3-thiazole-5-carboxamide

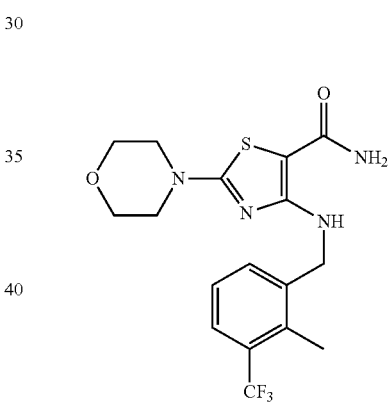

Isopropylmagnesium chloride (1.679 mL, 3.36 mmol) was added to a suspension of 2-(4-morpholinyl)[1,3]thiazolo[4,5-d]pyrimidin-7(4H)-one (0.8 g, 3.36 mmol) in Tetrahydrofuran (THF) (30 mL) at 0° C. LiHMDS (3.36 mL, 3.36 mmol) was added. The ice bath was removed. The reaction mixture was stirred at RT for 30 min, cooled down to 0° C. 1-(Bromomethyl)-2-methyl-3-(trifluoromethyl)benzene (1 g, 3.95 mmol) was added. The reaction mixture was heated at 60 C overnight. LCMS showed very clean reaction. NaOH (1.12 mL, 6.72 mmol, 6N) was added. The resulting mixture was heated at 60° C. for 1 hr (MeOH may be added to accelerate the reaction). LCMS showed the hydrolysis was almost complete. Water was added, creamy-colored solid was formed, filtered, rinsed with water, and dried under high vacuum at 50° C. to give 1.58 g of product, which may contain inorganic salt.

LCMS (ES) m/z=401.0 (M+H)$^+$, $^1$H NMR (400 MHz, DMSO-$d_6$) δ ppm 8.03 (m, 1H), 7.57 (m, 2H) 7.36 (m, 1H). 6.54 (s, 2H, NH$_2$), 4.64 (d, J=6.4 Hz), 3.68 (m, 4H), 3.94 (m, 4H), 2.41 (s, 3H).

b) 5-cyclopropyl-4-{[2-methyl-3-(trifluoromethyl)phenyl]methyl}-2-(4-morpholinyl)[1,3]thiazolo[4,5-d]pyrimidin-7(4H)-one Cyclopropanecarbonyl chloride (0.137 mL, 1.498 mmol) was added to a suspension of 4-({[2-methyl-3-(trifluoromethyl)phenyl]methyl}amino)-2-(4-morpholinyl)-1,3-thiazole-5-carboxamide (300 mg, 0.749 mmol) in Tetrahydrofuran (THF) (7 mL) at −20° C. The resulting mixture was allowed to warm up to RT and stirred overnight. LCMS showed completion of the acylation reaction. The reaction mixture was cooled down to 0° C. NaOH (0.400 mL, 2.4 mmol, 6N) and ethanol (0.50 mL) were added, the reaction mixture became clear. The resulting mixture was stirred at RT for 1 hr. Additional 2 eq. of base was added and the cyclization reaction was completed. The reaction mixture was taken into DCM, washed with brine, dried and concentrated. The residue was purified on a 25 mm silica column, which was eluted with 0-9% of MeOH in DCM to give 90 mg of Example 70 as a solid. LC/MS: MS (ES+) m/e 451 (MH+); $^1$H NMR (400 MHz, DMSO-$d_6$) δ ppm 0.83-0.92 (m, 2H), 0.98-1.07 (m, 2H), 1.86-1.97 (m, 1H), 2.51 (s, 3H), 3.45-3.56 (m, 4H), 3.63-3.73 (m, 4H), 5.76 (s, 2H), 6.92 (d, J=7.83 Hz, 1H), 7.37 (m, 1H), 7.64 (d, J=7.8 Hz, 1H).

Preparation of 5-cyclopropyl-4-{[2-methyl-3-(trifluoromethyl)phenyl]methyl}-2-(4-morpholinyl)[1,3]thiazolo[4,5-d]pyrimidin-7(4H)-one (Method B)

Scheme 9. Preparation of Example 70 (Method B)

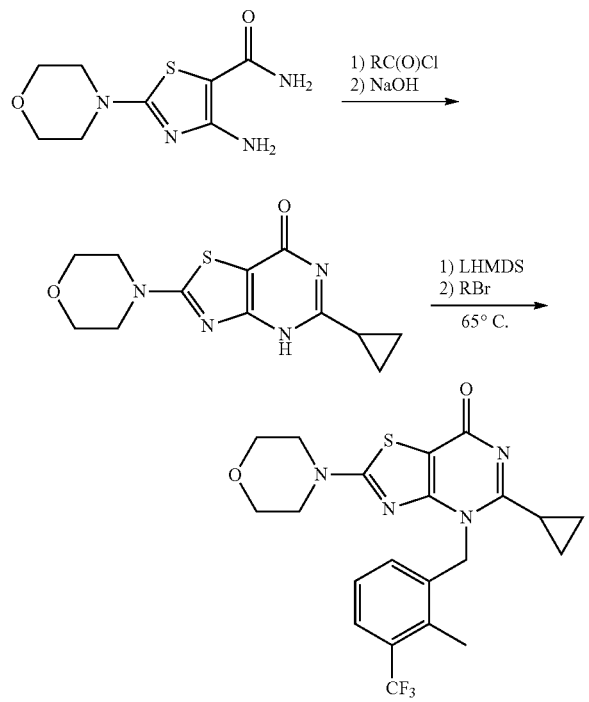

a) 5-cyclopropyl-2-(4-morpholinyl)[1,3]thiazolo[4,5-d]pyrimidin-7(4H)-one

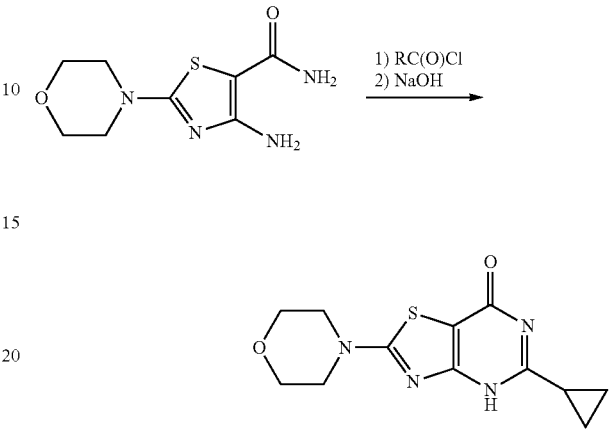

To a solution of 4-amino-2-(4-morpholinyl)-1,3-thiazole-5-carboxamide (0.15 g, 0.657 mmol) in Dichloromethane (DCM) (2 ml) at 0° C. was added cyclopropanecarbonyl chloride (0.075 ml, 0.821 mmol) dropwise. The mixture was stirred at room temperature overnight, and then concentrated. To the resulting residue was added ethanol (1 mL) and 6N NaOH (0.8 mL). The mixture was stirred at room temperature for 3 h, and then acidified with 6N HCl (0.7 mL) to pH ~5. The precipitate was collected, rinsed with water, and dried in vacuo to furnish crude 5-cyclopropyl-2-(4-morpholinyl)[1,3]thiazolo[4,5-d]pyrimidin-7(4H)-one. (90 mg, 49%); LC/MS: MS (ES) m/e 279 (MH+); $^1$H NMR (400 MHz, DMSO-$d_6$) δ ppm 0.99-1.06 (m, 4H), 1.95 (ddd, J=10.6, 2.0, 1.8 Hz, 1H) 3.53-3.59 (m, 4H) 3.68-3.76 (m, 4H) 12.56 (br, s, 1H).

b) 5-cyclopropyl-4-{[2-methyl-3-(trifluoromethyl)phenyl]methyl}-2-(4-morpholinyl)[1,3]thiazolo[4,5-d]pyrimidin-7(4H)-one A solution of 5-cyclopropyl-2-(4-morpholinyl)[1,3]thiazolo[4,5-d]pyrimidin-7(4H)-one (50 mg, 0.180 mmol) in Tetrahydrofuran (THF) (1000 μl) was stirred at 0° C. for 15 min, then lithium bis(trimethylsilyl)amide (359 μl, 0.359 mmol) in THF was added and stirring was continued for 30 min. 1-(bromomethyl)-2-methyl-3-(trifluoromethyl)benzene (54.6 mg, 0.216 mmol) in Tetrahydrofuran (THF) (300 μl) was added and the mixture was stirred at 65° C. overnight. The reaction mixture was concentrated and the residue purified by reversed-phase HPLC to provide the major regio-isomer, 5-cyclopropyl-4-{[2-methyl-3-(trifluoromethyl)phenyl]methyl}-2-(4-morpholinyl)[1,3]thiazolo[4,5-d]pyrimidin-7(4H)-one (Example 70). (9 mg, 11%); LC/MS: MS (ES+) m/e 451 (MH+); $^1$H NMR (400 MHz, DMSO-$d_6$) δ ppm 0.83-0.92 (m, 2H), 0.98-1.07 (m, 2H), 1.86-1.97 (m, 1H), 2.51 (s, 3H), 3.45-3.56 (m, 4H), 3.63-3.73 (m, 4H), 5.76 (s, 2H), 6.92 (d, J=7.83 Hz, 1H), 7.37 (m, 1H), 7.64 (d, J=7.8 Hz, 1H).

The following compounds in the table were prepared according to the procedures of Example 70, method A

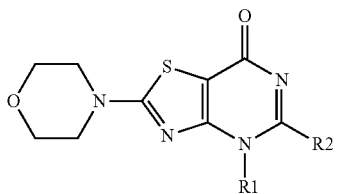

| Example | R1 | R2 | Name | Data |
|---|---|---|---|---|
| 71 | *-CH2-(2-methyl-3-Cl-phenyl) | *-cyclopropyl | 5-cyclopropyl-4-{[2-methyl-3-(trifluoromethyl)phenyl]methyl}-2-(4-morpholinyl)[1,3]thiazolo[4,5-d]pyrimidin-7(4H)-one | LCMS (ES) m/z = 417.2/418.8 (M + H)+, 1H NMR (400 MHz, CDCl3) δ ppm 7.36 (d, J = 8.0 Hz, 1H), 7.57 (dd, J = 8.0, 7.6 Hz, 1H) 7.36 (m, 1H), 6.63 (d, J = 6.63 Hz, 1H), 5.61 (s, 2H), 3.80 (m, 4H), 3.57 (m, 4H), 2.49 (s, 3H), 2.06-1.57 (m, 2H), 1.39-1.35 (m, 2H), 1.07-1.04 (m, 1H). |
| 72 | *-CH2-(2-methyl-3-Cl-phenyl) | *-cyclobutyl | 4-[(3-chloro-2-methylphenyl)methyl]-5-cyclobutyl-2-(4-morpholinyl)[1,3]thiazolo[4,5-d]pyrimidin-7(4H)-one | LCMS (ES) m/z 431.0 (M + H)+, 1H NMR (400 MHz, CDCl3-d1) δ ppm 7.34 (m, 1H), 7.05 (m, 1H), 6.41 (m, 1H), 5.38 (s, 2H), 3.78 (m, 4H), 3.53 (m, 4H), 2.60 (m, 2H), 2.48 (s, 3H), 2.13 (m, 2H), 1.98 (m, 2H), 1.70 (m, 1H) |
| 73 | *-CH2-(2-methyl-3-CF3-phenyl) | *-CH2CH2-S-CH3 | 5-[2-(methylthio)ethyl]-4-{[2-methyl-3-(trifluoromethyl)phenyl]methyl}-2-(4-morpholinyl)[1,3]thiazolo[4,5-d]pyrimidin-7(4H)-one | LCMS (ES) m/z 486.2 (M + H)+, 1H NMR (400 MHz, CDCl3-d1) δ ppm 7.63 (m, 1H), 7.24 (m, 1H), 6.78 (m, 1H), 5.56 (s, 2H), 3.79 (m, 4H), 3.56 (m, 4H), 3.01 (m, 2H), 2.82 (m, 2H), 2.54 (s, 3H), 2.03 (s, 3H) |
| 74 | *-CH2-(2-methyl-3-Cl-phenyl) | *-CH2CH2-S-CH3 | 4-[(3-chloro-2-methylphenyl)methyl]-5-[2-(methylthio)ethyl]-2-(4-morpholinyl)[1,3]thiazolo[4,5-d]pyrimidin-7(4H)-one | LCMS (ES) m/z 452.9(M + H)+, 1H NMR (400 MHz, CDCl3-d1) δ ppm 7.38 (m, 1H), 7.09 (m, 1H), 6.43 (m, 1H), 5.62 (s, 2H), 3.82 (m, 4H), 3.63 (m, 4H), 2.94 (m, 4H), 2.50 (s, 3H), 2.05 (s, 3H) |
| 75 | *-CH2-(2-methyl-3-Cl-phenyl) | *-ethyl | 4-[(3-chloro-2-methylphenyl)methyl]-5-ethyl-2-(4-morpholinyl)[1,3]thiazolo[4,5-d]pyrimidin-7(4H)-one | LCMS (ES) m/z = 405.2 (M + H); 1H NMR (400 MHz, CDCl3) δ ppm 7.35 (d, 1H, J = 8 Hz), 7.08 (dd, 1H, J = 8 Hz, 7.6 Hz), 6.47 (d, 1H, J = 8 Hz), 5.47 (s, 2H), 3.81-3.79 (m, 4H), 3.58-3.51 (m, 4H), 2.63-2.57 (q, 2H, J = 7.6 Hz), 2.48 (s, 3H), 1.33-1.28 (t, 3H, J = 7.6 Hz). |
| 76 | *-CH2-(2-methyl-3-CF3-phenyl) | *-ethyl | 5-ethyl-4-{[2-methyl-3-(trifluoromethyl)phenyl]methyl}-2-(4-morpholinyl)[1,3]thiazolo[4,5-d]pyrimidin-7(4H)-one | LCMS (ES) m/z = 439.2 (M + H); 1H NMR (400 MHz, CDCl3) δ ppm 7.65 (d, 1H, J = 8 Hz), 7.25-7.20 (dd, 1H, J = 8 Hz, 7.6 Hz), 6.75 (d, 1H, J = 8 Hz), 5.50 (s, 2H), 3.81-3.78 (m, 4H), 3.57-3.55 (m, 4H), 2.61-2.59 (q, 2H, J = 7.2 Hz), 2.54 (s, 3H), 1.35-1.31 (t, 3H, J = 7.2 Hz). |
| 77 | *-CH2-(2-methyl-3-CF3-phenyl) | *-CH2-phenyl | 4-{[2-methyl-3-(trifluoromethyl)phenyl]methyl}-2-(4-morpholinyl)-5-(phenylmethyl)[1,3]thiazolo[4,5-d]pyrimidin-7(4H)-one | LCMS (ES) m/z = 501.1 (M + H); 1H NMR (400 MHz, CDCl3) δ ppm 7.62-7.60 (d, 1H, J = 8.0 Hz), 7.33-7.20 (m, 6H), 6.72-6.70 (d, 1H, J = 8 Hz), 5.36 (s, 2H), 3.97 (s, 2H), 3.78-3.76 (m, 4H), 3.55-3.51 (m, 4H), 2.40 (s, 3H). |

-continued

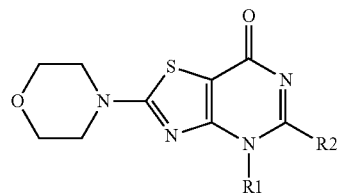

| Example | R1 | R2 | Name | Data |
|---|---|---|---|---|
| 78 | *-CH2-(2-methyl-3-chlorophenyl) | *-phenyl | 4-[(3-chloro-2-methylphenyl)methyl]-2-(4-morpholinyl)-5-(phenylmethyl)[1,3]thiazolo[4,5-d]pyrimidin-7(4H)-one | LCMS (ES) m/z = 467.0 (M + H); 1H NMR (400 MHz, CDCl3) δ ppm 7.37-7.23 (m, 6H), 7.10-7.06 (tr, 1H, J = 8 Hz), 6.48-6.46 (d, 1H, J = 8 Hz), 5.33 (s, 2H), 3.96 (s, 2H), 3.79-3.76 (m, 4H), 3.56-3.53 (m, 4H), 2.36 (s, 3H). |
| 79 | *-CH2-(2-methyl-3-trifluoromethylphenyl) | *-phenyl | 4-{[2-methyl-3-(trifluoromethyl)phenyl]methyl}-2-(4-morpholinyl)-5-phenyl[1,3]thiazolo[4,5-d]pyrimidin-7(4H)-one | LCMS (ES) m/z = 487.2 (M + H); 1H NMR (400 MHz, CDCl3) δ ppm 7.62-7.60 (d, 1H, J = 8.0 Hz), 7.60-7.25 (m, 6H), 6.97-6.95 (d, 1H, J = 8 Hz), 5.47 (s, 2H), 3.83-3.80 (m, 4H), 3.65-3.60 (m, 4H), 2.15 (s, 3H). |

Example 80

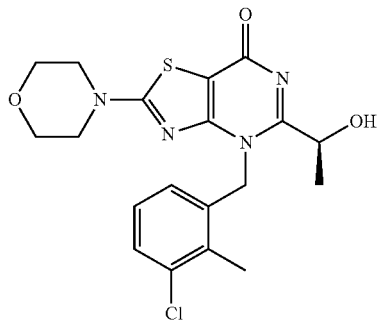 [SMILES: Cc1c(Cl)cccc1Cn1c([C@H](C)O)nc(=O)c2sc(N3CCOCC3)nc21]

Preparation of 4-[(3-chloro-2-methylphenyl)methyl]-5-[(1S)-1-hydroxyethyl]-2-(4-morpholinyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (200 mg, 0.545 mmol) in Tetrahydrofuran (THF) (20001) was added (1S)-2-chloro-1-methyl-2-oxoethyl acetate (164 mg, 1.090 mmol). The mixture was stirred at room temperature overnight, and then stirred at 60° C. for 3 h. To the mixture was added sodium hydroxide (454 µl, 2.73 mmol) and methanol (0.5 mL). After 30 min, the mixture was acidified (pH ~5) with 6N HCl, and then concentrated. The residue was partitioned between dichloromethane and water. The organic layer was dried (sodium sulfate), filtered, and concentrated. The crude was purified by reversed-phase HPLC and subsequently converted to the HCl salt to provide 4-[(3-chloro-2-methylphenyl)methyl]-5-[(S)-1-hydroxyethyl]-2-(4-morpholinyl)[1,3]thiazolo[4,5-d]pyrimidin-7(4H)-one. (14 mg, 6%); LC/MS: MS (ES+) m/e 421 (MH+); 1H NMR (400 MHz, DMSO-d6) δ ppm 1.34 (d, J=6.3 Hz, 3H), 2.44 (s, 3H), 3.53-3.62 (m, 4H), 3.67 (m, 4H), 4.57 (q, J=6.3 Hz, 1H), 5.67 (s, 2H), 6.51 (d, J=7.8 Hz, 1H), 7.14 (m, 1H), 7.37 (d, J=7.8 Hz, 1H).

Example 81

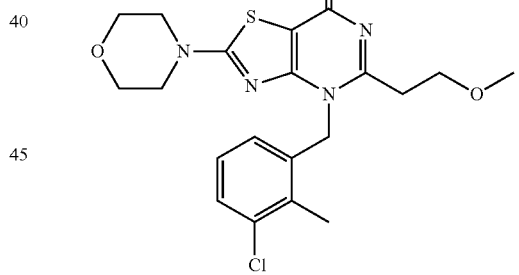

Preparation of 4-[(3-chloro-2-methylphenyl)methyl]-5-[2-(methloxy)ethyl]-2-(4-morpholinyl)[1,3]thiazolo[4,5-d]pyrimidin-7(4H)-one 3-methoxypropionyl chloride (66.8 mg, 0.545 mmol) in 1,2-Dimethoxyethane (DME) (400 µl) was added to a solution of 4-{[(3-chloro-2-methylphenyl)methyl]amino}-2-(4-morpholinyl)-1,3-thiazole-5-carboxamide (100 mg, 0.273 mmol) in 1,2-Dimethoxyethane (DME) (1000 µl). The mixture was stirred at room temperature overnight, then quenched with methanol and concentrated. To the residue was added methanol (1 mL) followed by 6N NaOH (1 equiv.). The mixture was stirred at room temperature for 3 h, neutralized (pH ~8) with 6N HCl, and concentrated. The residue was partitioned between dichloromethane and water. The organic layer was dried (sodium sulfate), filtered, and concentrated. The crude product was purified by reversed-phase HPLC and the fractions were neutralized with sat. aq. sodium bicarbonate. The combined fractions were concentrated to remove acetonitrile and the remaining water was extracted with dichloromethane. The organic layer was dried (sodium sulfate), filtered, and concentrated to provide 4-[(3-chloro-2-methylphenyl)methyl]-5-[2-(methyloxy)ethyl]-2-(4-morpholinyl)[1,3]thiazolo[4,5-d]pyrimidin-7(4H)-one. (14 mg, 12%); LC/MS: MS (ES+) m/e 435 (MH+); $^1$H NMR (400 MHz, DMSO-$d_6$) δ ppm 2.44 (s, 3H), 2.80 (t, J=6.7 Hz, 2H), 3.19 (s, 3H), 3.52 (m, 4H), 3.62-3.72 (m, 6H), 5.57 (s, 2H), 6.51 (d, J=7.6 Hz, 1H), 7.16 (m, 1H), 7.39 (d, J=7.8 Hz, 1H).

To the residue in Methanol (1200 μl) was added 6N NaOH (2 equiv). The mixture was stirred at 40° C. for 3 h then acidified (pH ~5) with 6N HCl. The precipitate was filtered, washed with water, and purified by reversed-phase HPLC to provide 4-[(3-chloro-2-methylphenyl)methyl]-2-(4-morpholinyl)-5-(tetrahydro-3-furanyl)[1,3]thiazolo[4,5-d]pyrimidin-7(4H)-one. (11 mg, 9%); LC/MS: MS (ES+) m/e 447 (MH+); $^1$H NMR (400 MHz, CHLOROFORM-d) δ ppm 2.01-2.09 (m, 1H), 2.39-2.48 (m, 1H), 2.49 (s, 3H), 3.18-3.30 (m, 1H), 3.61 (m, 4H), 3.76-3.85 (m, 4H), 3.87-3.98 (m, 3H), 3.98-4.05 (m, 1H), 5.50-5.67 (m, 2H), 6.40 (d, J=7.6 Hz, 1H), 7.11 (m, 1H), 7.39 (d, J=7.8 Hz, 1 H).

Example 82

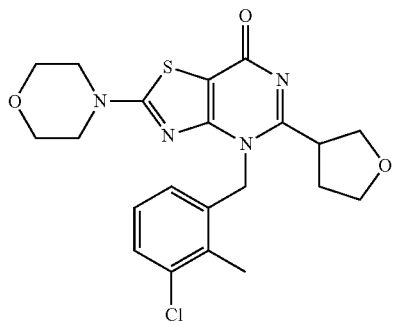 [SMILES: Cc1c(Cl)cccc1Cn1c(C2CCOC2)nc(=O)c2sc(N3CCOCC3)nc21]

Preparation of 4-[(3-chloro-2-methylphenyl)methyl]-2-(4-morpholinyl)-5-(tetrahydro-3-furanyl)[1,3]thiazolo[4,5-d]pyrimidin-7(4H)-one a) tetrahydro-3-furancarbonyl chloride

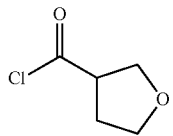

To a solution of tetrahydro-3-furancarboxylic acid (500 mg, 4.31 mmol) in Dichloromethane (DCM) (10 ml) was added oxalyl chloride (1.131 ml, 12.92 mmol), followed by 2 drops of DMF. The mixture was stirred at room temperature for 30 min, and then excess oxalyl chloride and dichloromethane were removed in vacuo to provide crude tetrahydro-3-furancarbonyl chloride (575 mg, 99%).

b) 4-[(3-chloro-2-methylphenyl)methyl]-2-(4-morpholinyl)-5-(tetrahydro-3-furanyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in 1,2-Dimethoxyethane (DME) (1.2 ml) was added tetrahydro-3-furancarbonyl chloride (73.4 mg, 0.545 mmol) in 1,2-Dimethoxyethane (DME) (200 μl). The mixture was stirred at room temperature overnight then quenched with methanol and concentrated.

Example 83

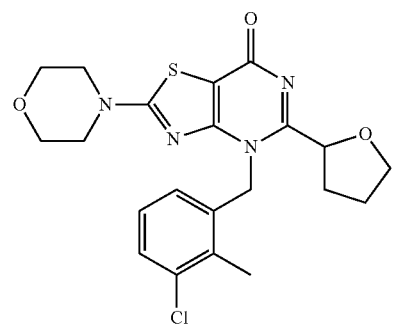 [SMILES: Cc1c(Cl)cccc1Cn1c(C2CCCO2)nc(=O)c2sc(N3CCOCC3)nc21]

Preparation of 4-[(3-chloro-2-methylphenyl)methyl]-2-(4-morpholinyl)-5-(tetrahydro-2-furanyl)[1,3]thiazolo[4,5-d]pyrimidin-7(4H)-one a) tetrahydro-2-furancarbonyl chloride

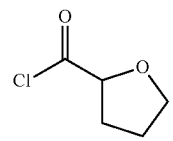

To a solution of tetrahydro-2-furancarboxylic acid (1 g, 8.61 mmol) in Dichloromethane (DCM) (17.22 ml) was added oxalyl chloride (3.02 ml, 34.4 mmol), followed by 2 drops of DMF. The mixture was stirred at room temperature for 30 min, then excess oxalyl chloride and dichloromethane were removed in vacuo to provide crude tetrahydro-2-furancarbonyl chloride. (1.15 g, 99%).

b) 4-[(3-chloro-2-methylphenyl)methyl]-2-(4-morpholinyl)-5-(tetrahydro-2-furanyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in 1,2-Dimethoxyethane (DME) (1000 μl) was added tetrahydro-2-furancarbonyl chloride (73.4 mg, 0.545 mmol) in 1,2-Dimethoxyethane (DME) (400 μl). The mixture was stirred at room temperature overnight, then additional tetrahydro-2-furancarbonyl chloride (1 equiv.) was added and the mixture was irradiated (uwave) for 15 min at 90° C. The mixture was quenched with methanol, concentrated, and purified by reversed-phase HPLC to provide 4-[(3-chloro-2-methylphenyl)methyl]-2-(4-morpholinyl)-5-(tetrahydro-2-furanyl)[1,3]thiazolo[4,5-d]pyrimidin-7(4H)-one. (18 mg, 15%); LC/MS: MS (ES+) m/e 447 (MH+); $^1$H NMR (400 MHz, DMSO-$d_6$) δ ppm 1.79-1.91 (m, 1H), 1.94-2.05 (m, 2H), 2.35-2.42 (m, 1H), 2.43 (s, 3H), 3.55-3.60 (m, 4H), 3.67 (m, 4H), 3.76 m, 1H), 3.84 (qm, 1H), 4.79 (m, 1H), 5.64 (s, 2H), 6.52 (d, J=7.6 Hz, 1H), 7.14 (m, 1H), 7.37 (d, J=8.1 Hz, 1H).

Example 84

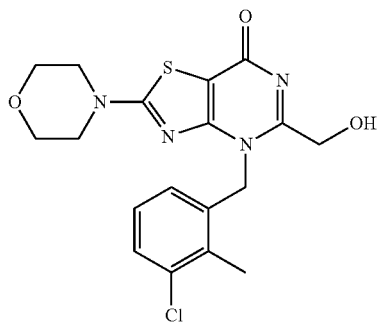 [SMILES: Cc1c(Cl)cccc1Cn1c(CO)nc(=O)c2sc(N3CCOCC3)nc21]

Preparation of 4-[(3-chloro-2-methylphenyl)methyl]-5-(hydroxymethyl)-2-(4-morpholinyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (1 g, 2.73 mmol) in 1,2-Dimethoxyethane (DME) (20 ml) at 0° C. was added acetoxyacetyl chloride (0.586 ml, 5.45 mmol). The mixture was stirred at room temperature for 2 h, then stirred at 50° C. overnight. The mixture was quenched with methanol and concentrated. To the resulting residue in Methanol (12 ml) was added 6N NaOH (0.9 mL, 5.45 mmol). The mixture was stirred at room temperature for 60 min, then acidified (~pH 5) with 1N HCl. The solvent was removed and the residue was partitioned between dichloromethane and water. The organic layer was dried (sodium sulfate), filtered, and concentrated. Reversed-phase HPLC purification provided 4-[(3-chloro-2-methylphenyl)methyl]-5-(hydroxymethyl)-2-(4-morpholinyl)[1,3]thiazolo[4,5-d]pyrimidin-7(4H)-one. (250 mg, 22%); LC/MS: MS (ES+) m/e 407 (MH+); $^1$H NMR (400 MHz, DMSO-$d_6$) δ ppm 2.43 (s, 3H), 3.51 (m, 4H), 3.67 (m, 4H), 4.32 (d, J=5.6 Hz, 2H), 5.57 (s, 2H), 5.64 (t, J=5.6 Hz, 1H, OH), 6.51 (d, J=7.6 Hz, 1H), 7.14 (m, 1H), 7.37 (d, J=7.8 Hz, 1H).

Example 85

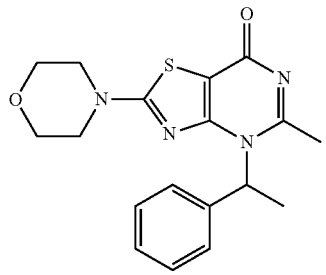 [SMILES: Cc1nc(=O)c2sc(N3CCOCC3)nc2n1C(C)c1ccccc1]

Preparation of 5-methyl-2-(4-morpholinyl)-4-(1-phenylethyl)[1,3]thiazolo[4,5-d]pyrimidin-7(4H)-one a) N-[5-cyano-2-(4-morpholinyl)-1,3-thiazol-4-yl]-N-(1-phenylethyl)acetamide

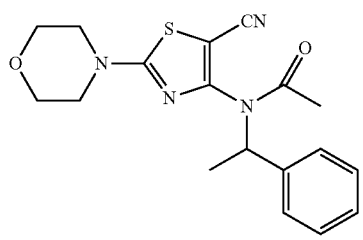 [SMILES: CC(=O)N(c1nc(N2CCOCC2)sc1C#N)C(C)c1ccccc1]

NaH (43.6 mg, 1.090 mmol) was added to a suspension of N-[5-cyano-2-(4-morpholinyl)-1,3-thiazol-4-yl]acetamide (250 mg, 0.991 mmol) in Tetrahydrofuran (THF) (8 mL) at 0° C. The resulting mixture was stirred at 0° C. for 10 min. (1-Bromoethyl)benzene (183 mg, 0.991 mmol) was added dropwise. N,N-Dimethylformamide (DMF) (2 mL) was added. The reaction mixture was heated at 50° C. overnight. LCMS showed the reaction was almost completed. EtOAc was added and washed with H$_2$O, brine and dried (Na$_2$SO$_4$). Removal of the solvent followed by flash column chromatography on a 25 g silica column, which was eluted with 50% EtOAc/hexane to give 300 mg of light yellow sticky/foamy solid as the product.

b) 5-Methyl-2-(4-morpholinyl)-4-(1-phenylethyl)[1,3]thiazolo[4,5-d]pyrimidin-7(4H)-one A mixture of N-[5-cyano-2-(4-morpholinyl)-1,3-thiazol-4-yl]-N-(1-phenylethyl)acetamide (300 mg, 0.842 mmol), sodium perborated tetrahydrate (129 mg, 0.84 mmol), Methanol (3 mL) and Water (3.00 mL) was heated at 55° C. for 2 h. The reaction became clear. The reaction mixture was extracted with DCM and the combined organic layers were washed with brine, dried and concentrated. The residue was purified on a 25 g silica column, which was eluted with 0-6% MeOH in DCM to give 90 mg of product as a white solid. LCMS (ES) m/z=357.3 (M+H)+, $^1$H NMR (400 MHz, CDCl$_3$) δ ppm 7.4-7.2 (m, 5H), 6.4 (m, 1H), 3.79 (m, 4H), 3.54 (m, 4H), 2.43 (br s, 3H), 2.01 (d, J=6.4 Hz).

The following compounds in the table were prepared according to the procedures of Example 8 and Example 81

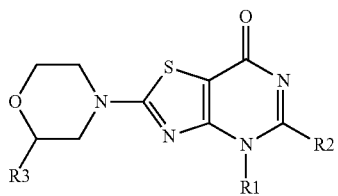

| Example | R1 | R2 | R3 | Name | Data |
|---|---|---|---|---|---|
| 86 | *-CH2-(2-methyl-3-trifluoromethylphenyl) | *-CH(CH3)2 | Me | 5-(1-methylethyl)-2-(2-methyl-4-morpholinyl)-4-{[2-methyl-3-(trifluoromethyl)phenyl]methyl}[1,3]thiazolo[4,5-d]pyrimidin-7(4H)-one | LCMS (ES) m/z 467.0 (M + H)+, 1H NMR (400 MHz, CDCl3-d1) δ ppm 7.63 (m, 1H), 7.25 (m, 1H), 6.72 (m, 1H), 5.57 (s, 2H), 3.80 (m, 3H), 3.65 (m, 4H), 2.91 (m, 3H), 2.54 (s, 3H), 1.26 (m, 6H), 1.16 (m, 1H) |
| 87 | *-CH2-(2-methyl-3-trifluoromethylphenyl) | *-CH2OH | H | 5-(hydroxymethyl)-4-{[2-methyl-3-(trifluoromethyl)phenyl]methyl}-2-(4-morpholinyl)[1,3]thiazolo[4,5-d]pyrimidin-7(4H)-one | LCMS (ES) m/z 441.0 (M + H)+, 1H NMR (400 MHz, DMSO-d6) δ ppm 7.65 (m, 1H), 7.36 (m, 1H), 6.87 (m, 1H), 5.60 (s, 2H), 4.15 (m, 2H), 3.66 (m, 4H), 3.56 (m, 4H), 2.49 (s, 3H) |
| 88 | *-CH2-(2-methyl-3-trifluoromethylphenyl) | *-CH(CH3)2 | H | 5-(1-methylethyl)-4-{[2-methyl-3-(trifluoromethyl)phenyl]methyl}-2-(4-morpholinyl)[1,3]thiazolo[4,5-d]pyrimidin-7(4H)-one | LCMS (ES) m/z 453.1 (M + H)+, 1H NMR (400 MHz, CDCl3-d1) δ ppm 7.63 (m, 1H), 7.25 (m, 1H), 6.71 (m, 1H), 5.60 (s, 2H), 3.78 (m, 4H), 3.59 (m, 4H), 2.51 (s, 3H) 1.36 (m, 6H), 1.20 (m, 1H) |
| 89 | *-CH2-(2-methyl-3-trifluoromethylphenyl) | *-CH2F | H | 5-(fluoromethyl)-4-{[2-methyl-3-(trifluoromethyl)phenyl]methyl}-2-(4-morpholinyl)[1,3]thiazolo[4,5-d]pyrimidin-7(4H)-one | LCMS (ES) m/z 443.0 (M + H)+, 1H NMR (400 MHz, CDCl3-d1) δ ppm 7.62 (m, 1H), 7.26 (m, 1H), 6.78 (m, 1H), 5.65 (s, 2H), 5.29 (d, J = 46.8 Hz, 2H), 3.88 (m, 4H), 3.58 (m, 4H), 2.53 (s, 3H) |
| 90 | *-CH2-(3-chloro-2-methylphenyl) | *-CH2F | H | 4-[(3-chloro-2-methylphenyl)methyl]-5-(fluoromethyl)-2-(4-morpholinyl)[1,3]thiazolo[4,5-d]pyrimidin-7(4H)-one | LCMS (ES) m/z 409.2 (M + H)+, 1H NMR (400 MHz, CDCl3-d1) δ ppm 7.37 (m, 1H), 7.08 (m, 1H), 6.42 (m, 1H), 5.70 (s, 2H), 5.30 (d, J = 46.8 Hz, 2H), 3.83 (m, 4H), 3.64 (m, 4H), 2.48 (s, 3H) |

The following three compounds in the table were prepared according to the procedures described in scheme 10.

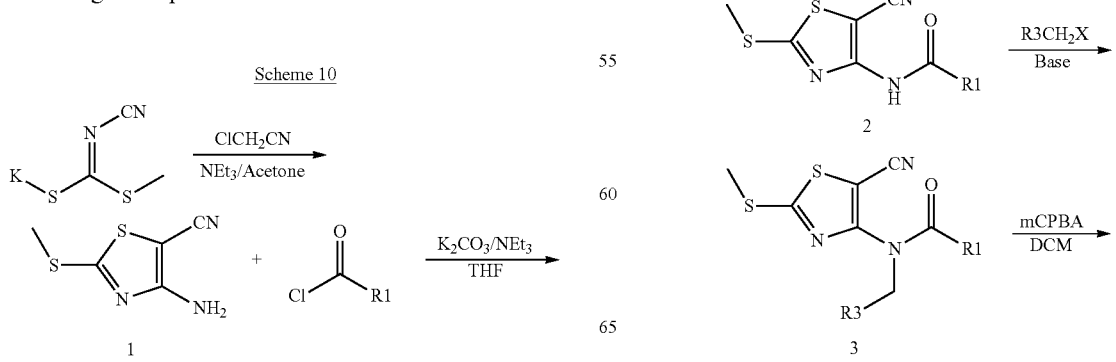

Scheme 10

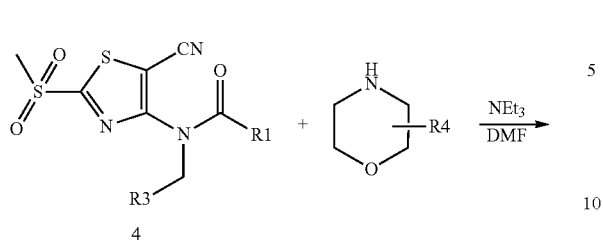

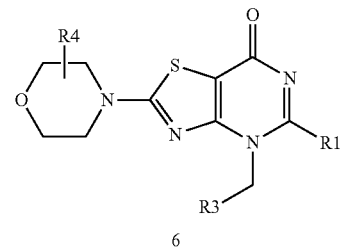

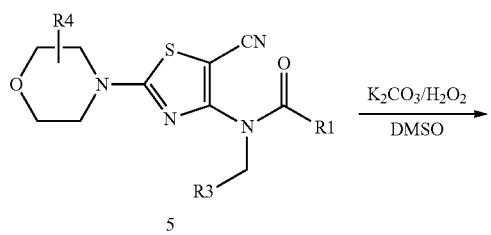

The potassium salt of methyl cyanodithiocarbamate is reacted with chloroacetonitrile in acetone in the presence of triethylamine to afford amino thiazole 1. Acylation with an acid chloride in the presence of base in THF provides the acyl aminothiazole derivative 2 that is then alkylated with an alkyl halide in an appropriate solvent such as THF or DMF in the presence of base (NaH or $K_2CO_3$) to provide compound 3. Oxidation of the sulfide to the sulfone, followed by displacement with a substituted morpholine provides compound 5 that can be converted to the desired final products (6) in the presence of basic hydrogen peroxide in DMSO.

| Example | R1 | R2 | R3 | Name | Data |
|---|---|---|---|---|---|
| 91 | * (3,4-dichlorobenzyl) | Me | Me | 4-[(3,4-dichlorophenyl)methyl]-5-methyl-2-(2-methyl-4-morpholinyl)[1,3]thiazolo[4,5-d]pyrimidin-7(4H)-one | LCMS (ES) m/z 426.8 (M + H)+, 1H NMR (300 MHz, CDCl3-d1) δ ppm 7.43 (d, 1H), 7.26 (s, 1H), 6.96 (d, 1H), 5.42 (s, 2H), 4.01 (d, 1H), 3.85-3.62 (m, 4H), 3.26 (bt, 1H), 2.94 (t, 1H), 2.48 (s, 3H), 1.21 (d, 3H). |
| 92 | * (2-methyl-3-trifluoromethylbenzyl) | Me | Me | 5-methyl-2-(2-methyl-4-morpholinyl)-4-{[2-methyl-3-(trifluoromethyl)phenyl]methyl}[1,3]thiazolo[4,5-d]pyrimidin-7(4H)-one | LCMS (ES) m/z 439.1 (M + H)+, 1H NMR (300 MHz, CDCl3-d1) δ ppm 7.61 (d, 1H), 7.22 (t, 1H), 6.78 (d, 1H), 5.48 (s, 2H), 4.01 (d, 1H), 3.85-3.62 (m, 4H), 3.26 (bt, 1H), 2.90 (t, 1H), 2.52 (s, 3H), 2.43 (s, 3H), 1.23 (d, 3H). |
| 93 | * (3-chloro-2-methylbenzyl) | Me | Me | 4-[(3-chloro-2-methylphenyl)methyl]-5-methyl-2-(2-methyl-4-morpholinyl)[1,3]thiazolo[4,5-d]pyrimidin-7(4H)-one | LCMS (ES) m/z 404.9 (M + H)+, 1H NMR (300 MHz, CDCl3-d1) δ ppm 7.34 (d, 1H), 7.08 (t, 1H), 6.49 (d, 1H), 5.48 (s, 2H), 3.99 (d, 1H), 3.85-3.62 (m, 4H), 3.28 (bt, 1H), 2.91 (t, 1H), 2.42 (s, 6H), 1.25 (d, 3H). |

The following compounds in the table were prepared according to the procedures of Example 70, method B.

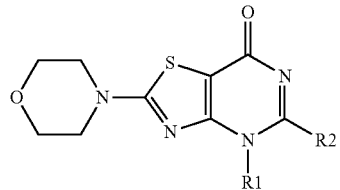

| Example | R1 | R2 | Name | Data |
|---|---|---|---|---|
| 94 | *-CH₂CH₂-(2-methylphenyl) | H | 4-[2-(2-methylphenyl)ethyl]-2-(4-morpholinyl)[1,3]thiazolo[4,5-d]pyrimidin-7(4H)-one | LCMS (ES) m/z 357.3 (M + H)+, $^1$H NMR (400 MHz, CDCl$_3$-d1) δ ppm 7.79 (br, s, 1H), 7.16 (m, 3H), 7.02 (m, 1H), 4.29 (m, 2H), 3.88 (m, 4H), 3.68 (m, 4H), 3.13 (m, 2H), 2.34 (s, 3H) |

Example 95

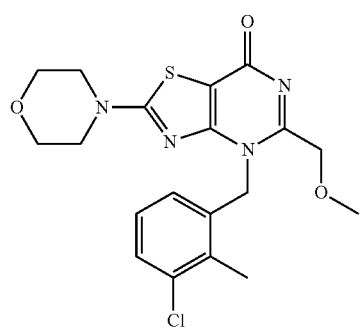 [SMILES: COCc1nc(=O)c2sc(N3CCOCC3)nc2n1Cc1cccc(Cl)c1C]

Preparation of 4-[(3-chloro-2-methylphenyl)methyl]-5-[(methyloxy)methyl]-2-(4-morpholinyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in Tetrahydrofuran (THF) (8001) at 0° C. was added methoxyacetyl chloride (49.7 μl, 0.545 mmol). The mixture was stirred at room temperature overnight, then quenched with methanol and concentrated. The residue was purified by reversed-phase HPLC to provide 4-[(3-chloro-2-methylphenyl)methyl]-5-[(methyloxy)methyl]-2-(4-morpholinyl)[1,3]thiazolo[4,5-d]pyrimidin-7(4H)-one. (16 mg, 14%); LC/MS: MS (ES+) m/e 421 (MH+); $^1$H NMR (400 MHz, DMSO-d$_6$) δ ppm 2.43 (s, 3H), 3.23 (s, 3H), 3.49-3.54 (m, 4H), 3.57-3.65 (m, 4H), 4.36 (s, 2H), 5.54 (s, 2H), 6.54 (d, J=7.6 Hz, 1H), 7.14 (m, 1H), 7.37 (d, J=7.8 Hz, 1H).

Example 96

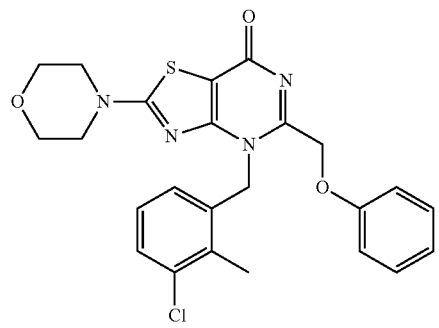 [SMILES: Cc1c(Cl)cccc1Cn1c(COc2ccccc2)nc(=O)c2sc(N3CCOCC3)nc21]

Preparation of 4-[(3-chloro-2-methylphenyl)methyl]-2-(4-morpholinyl)-5-[(phenyloxy)methyl][1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in Tetrahydrofuran (THF) (1363 μl) at 0° C. was added phenoxyacetyl chloride (75 μl, 0.545 mmol). The mixture was stirred at room temperature overnight, then quenched with methanol and concentrated. The residue was purified by reversed-phase HPLC to provide 4-[(3-chloro-2-methylphenyl)methyl]-2-(4-morpholinyl)-5-[(phenyloxy)methyl][1,3]thiazolo[4,5-d]pyrimidin-7(4H)-one. (19 mg, 14%); LC/MS: MS (ES+) m/e 483 (MH+); $^1$H NMR (400 MHz, DMSO-d$_6$) δ ppm 2.29 (s, 3H), 3.52 (t, J=4.7 Hz, 4H), 3.67 (t, J=4.7 Hz, 4H), 5.07 (s, 2H), 5.55 (s, 2H), 6.55 (m, 1H), 6.69 (d, J=7.8 Hz, 2H), 6.94 (m, 1H), 7.12 (m, 1H), 7.22 (m, 2H), 7.36 (d, J=7.8 Hz, 1H).

Example 97

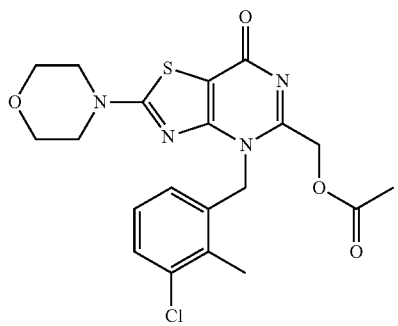 [SMILES: CC(=O)OCc1nc(=O)c2sc(N3CCOCC3)nc2n1Cc1cccc(Cl)c1C]

Preparation of [4-[(3-chloro-2-methylphenyl)methyl]-2-(4-morpholinyl)-7-oxo-4,7-dihydro[1,3]thiazolo[4,5-d]pyrimidin-5-yl]methyl acetate To a solution of 4-{[(3-chloro-2-methylphenyl)methyl]amino}-2-(4-morpholinyl)-1,3-thiazole-5-carboxamide (200 mg, 0.545 mmol) in Tetrahydrofuran (THF) (2726 µl) at 0° C. was added acetoxyacetyl chloride (117 µl, 1.090 mmol). The mixture was stirred at 50° C. for 3 h, then quenched with methanol and concentrated. The residue was subjected to silica gel chromatography (0-5% methanol/dichloromethane) followed by reversed-phase HPLC purification to provide [4-[(3-chloro-2-methylphenyl)methyl]-2-(4-morpholinyl)-7-oxo-4,7-dihydro[1,3]thiazolo[4,5-d]pyrimidin-5-yl]methyl acetate. (49 mg, 20%); LC/MS: MS (ES$^+$) m/e 449 (MH$^+$); $^1$H NMR (400 MHz, DMSO-d$_6$) δ ppm 1.85 (s, 3H), 2.42 (s, 3H), 3.52 (m, 4H), 3.67 (m, 4H), 5.03 (s, 2H), 5.50 (s, 2H), 6.54 (d, J=7.6 Hz, 1H), 7.17 (m, 1H), 7.39 (d, J=7.8 Hz, 1H).

Example 98

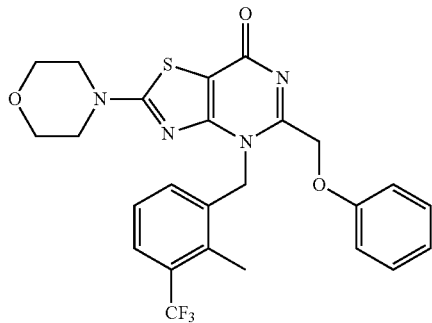 [SMILES: Cc1c(Cn2c(COc3ccccc3)nc(=O)c3sc(N4CCOCC4)nc32)cccc1C(F)(F)F]

Preparation of 4-{[2-methyl-3-(trifluoromethyl)phenyl]methyl}-2-(4-morpholinyl)-5-[(phenyloxy)methyl][1,3]thiazolo[4,5-d]pyrimidin-7(4H)-one To a solution of 4-({[2-methyl-3-(trifluoromethyl)phenyl]methyl}amino)-2-(4-morpholinyl)-1,3-thiazole-5-carboxamide (100 mg, 0.250 mmol) in Tetrahydrofuran (THF) (1249 µl) at 0° C. was added phenoxyacetyl chloride (69.0 µl, 0.499 mmol). The mixture was stirred at room temperature overnight, then quenched with methanol and concentrated. The residue was purified by reversed-phase HPLC to provide 4-{([2-methyl-3-(trifluoromethyl)phenyl]methyl}-2-(4-morpholinyl)-5-[(phenyloxy)methyl][1,3]thiazolo[4,5-d]pyrimidin-7(4H)-one. (14 mg, 11%); LC/MS: MS (ES$^+$) m/e 517 (MH$^+$); $^1$H NMR (400 MHz, DMSO-d$_6$) δ ppm 2.34 (s, 3H), 3.48-3.54 (m, 4H), 3.62-3.71 (m, 4H), 5.12 (s, 2H), 5.57 (s, 2H), 6.61 (d, J=7.8 Hz, 2H), 6.85-6.97 (m, 2H), 7.19 (dd, J=8.7, 7.5 Hz, 2H), 7.25-7.33 (m, 1H), 7.60 (d, J=7.8 Hz, 1H).

Example 99

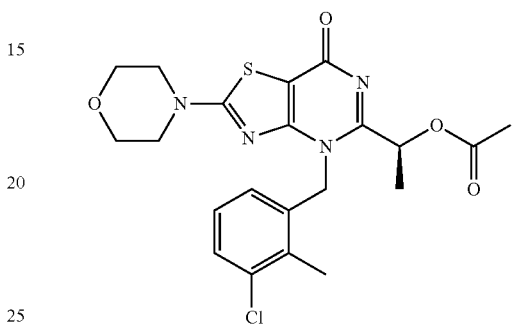

Preparation of (1S)-1-[4-[(3-chloro-2-methylphenyl)methyl]-2-(4-morpholinyl)-7-oxo-4,7-dihydro[1,3]thiazolo[4,5-d]pyrimidin-5-yl]ethyl acetate To a solution of 4-{[(3-chloro-2-methylphenyl)methyl]amino}-2-(4-morpholinyl)-1,3-thiazole-5-carboxamide (100 mg, 0.273 mmol) in Tetrahydrofuran (THF) (1363 µl) was added (1S)-2-chloro-1-methyl-2-oxoethyl acetate (82 mg, 0.545 mmol). The mixture was stirred at room temperature overnight, then additional (1S)-2-chloro-1-methyl-2-oxoethyl acetate (1 equiv.) was added and stirring was continued at 60° C. for 2 h. The mixture was quenched with methanol and concentrated. The residue was purified by reversed-phase HPLC to provide (1S)-1-[4-[(3-chloro-2-methylphenyl)methyl]-2-(4-morpholinyl)-7-oxo-4,7-dihydro[1,3]thiazolo[4,5-d]pyrimidin-5-yl]ethyl acetate. (11 mg, 9%); LC/MS: MS (ES$^+$) m/e 463 (MH$^+$); $^1$H NMR (400 MHz, DMSO-d$_6$) δ ppm 1.37 (d, J=6.3 Hz, 3H), 1.71 (s, 3H), 2.40 (s, 3H), 3.51-3.54 (m, 4H), 3.67 (m, 4H), 5.48-5.61 (m, 2H), 5.69 (q, J=6.3 Hz, 1H), 6.56 (d, J=7.6 Hz, 1H), 7.16 (m, 1H), 7.38 (d, J=7.8 Hz, 1H).

Example 100

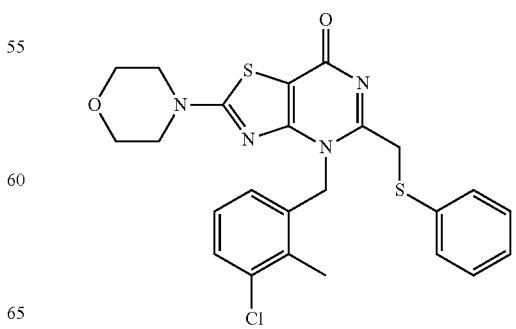

Preparation of 4-[(3-chloro-2-methylphenyl)methyl]-2-(4-morpholinyl)-5-[(phenylthio)methyl][1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in Tetrahydrofuran (THF) (1363 µl) was added thiophenoxyacetyl chloride (102 mg, 0.545 mmol). The mixture was stirred at room temperature for 3 h, then irradiated (uwave) at 90° C. for 15 min. The mixture was quenched with methanol, concentrated, and purified by reversed-phase HPLC to provide 4-[(3-chloro-2-methylphenyl)methyl]-2-(4-morpholinyl)-5-[(phenylthio)methyl][1,3]thiazolo[4,5-d]pyrimidin-7(4H)-one. (20 mg, 15%); LC/MS: MS (ES$^+$) m/e 499 (MH$^+$); $^1$H NMR (400 MHz, DMSO-d$_6$) δ ppm 2.36 (s, 3H), 3.52-3.59 (m, 4H), 3.62-3.73 (m, 4H), 4.18 (s, 2H), 5.59 (s, 2H), 6.52 (d, J=7.8 Hz, 1H), 7.15 (t, J=8.0 Hz, 1H), 7.21-7.42 (m, 6H).

Example 101

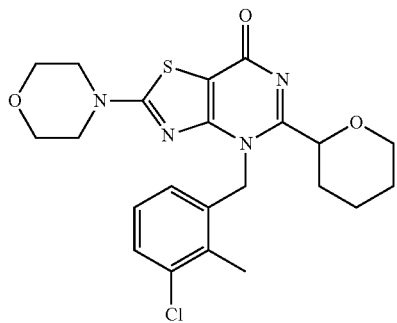 [SMILES: Cc1c(Cl)cccc1Cn1c(C2CCCCO2)nc(=O)c2sc(N3CCOCC3)nc21]

Preparation of 4-[(3-chloro-2-methylphenyl)methyl]-2-(4-morpholinyl)-5-(tetrahydro-2H-pyran-2-yl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in 1,2-Dimethoxyethane (DME) (1000 ul) was added tetrahydro-2H-pyran-2-carbonyl chloride (81 mg, 0.545 mmol) in 1,2-Dimethoxyethane (DME) (400 ul). The mixture was stirred at room temperature for 3 h, then irradiated (uwave) for 20 min at 90° C. The mixture was quenched with methanol, concentrated, and purified by reversed-phase HPLC to provide 4-[(3-chloro-2-methylphenyl)methyl]-2-(4-morpholinyl)-5-(tetrahydro-2H-pyran-2-yl)[1,3]thiazolo[4,5-d]pyrimidin-7(4H)-one. (17 mg, 14%); LC/MS: MS (ES*) m/e 461 (MH$^+$); $^1$H NMR (400 MHz, DMSO-d$_6$) δ ppm 1.46 (br. s., 3H), 1.62-1.72 (m, 1H), 1.78-1.98 (m, 2H), 2.45 (s, 3H), 3.45-3.57 (m, 5H), 3.66 (t, J=4.8 Hz, 4H), 3.81 (d, J=11.6 Hz, 1H), 4.28 (m, 1H), 5.51-5.66 (m, 2H), 6.49 (d, J=7.8 Hz, 1H), 7.13 (m, 1H), 7.36 (d, J=7.8 Hz, 1H).

Example 102

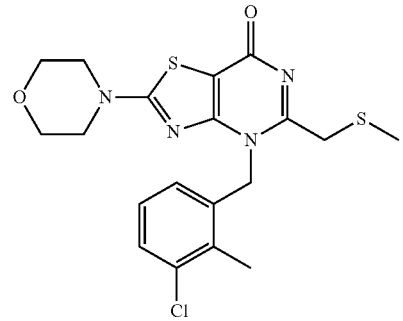 [SMILES: CSCc1nc(=O)c2sc(N3CCOCC3)nc2n1Cc1cccc(Cl)c1C]

Preparation of 4-[(3-chloro-2-methylphenyl)methyl]-5-[(methylthio)methyl]-2-(4-morpholinyl)[1,3]thiazolo[4,5-d]pyrimidin-7(4H)-one a) (methylthio)acetyl chloride

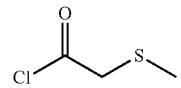

To a solution of (methylthio)acetic acid (0.820 ml, 9.42 mmol) in Dichloromethane (DCM) (18.84 ml) was added oxalyl chloride (3.30 ml, 37.7 mmol), followed by 2 drops of DMF. The mixture was stirred at room temperature for 30 min, then excess oxalyl chloride and dichloromethane were removed in vacuo to provide crude (methylthio)acetyl chloride. (1.17 g, 99%).

b) 4-[(3-chloro-2-methylphenyl)methyl]-5-[(methylthio)methyl]-2-(4-morpholinyl)[1,3]thiazolo[4,5-d]pyrimidin-7(4H)-one To a solution of 4-{[(3-chloro-2-methylphenyl)methyl]amino}-2-(4-morpholinyl)-1,3-thiazole-5-carboxamide (100 mg, 0.273 mmol) in 1,2-Dimethoxyethane (DME) (1000 µl) was added (methylthio)acetyl chloride (67.9 mg, 0.545 mmol) in 1,2-Dimethoxyethane (DME) (400 µl). The mixture was stirred at room temperature for 3 h, then irradiated (uwave) at 90° C. for 15 min. After quenching with methanol, the mixture was concentrated and purified by reversed-phase HPLC to provide 4-[(3-chloro-2-methylphenyl)methyl]-5-[(methylthio)methylthio)methyl]-2-(4-morpholinyl)[1,3]thiazolo[4,5-d]pyrimidin-7(4H)-one. (28 mg, 24%); LC/MS: MS (ES$^+$) m/e 437 (MH$^+$); $^1$H NMR (400 MHz, DMSO-d$_6$) δ ppm 2.11 (s, 3H), 2.43 (s, 3H), 3.51 (m, 4H), 3.62 (s, 2H), 3.64-3.71 (m, 4H), 5.59 (s, 2H), 6.53 (d, J=7.8 Hz, 1H), 7.15 (m, 1H), 7.38 (d, J=8.01 Hz, 1H).

Example 103

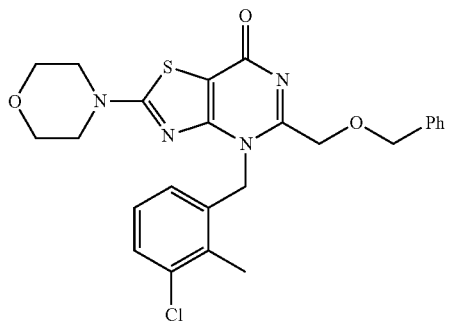 [SMILES: Cc1c(Cl)cccc1Cn1c(COCc2ccccc2)nc(=O)c2sc(N3CCOCC3)nc21]

Preparation of 4-[(3-chloro-2-methylphenyl)methyl]-2-(4-morpholinyl)-5-{[(phenylmethyl)oxy]methyl}[1,3]thiazolo[4,5-d]pyrimidin-7(4H)-one The titled compound was prepared using the method described in example 102 substituting [(phenylmethyl)oxy]acetyl chloride for (methylthio)acetyl chloride. LCMS (ES) m/z=497.0/499.1 (M+H); $^1$H NMR (400 MHz, CDCl$_3$) δ ppm 7.35-7.20 (m, 6H), 7.05-7.00 (m, 1H), 6.44-6.42 (m, 1H), 5.67 (s, 2H), 4.67 (s, 2H), 4.58 (s, 2H), 3.81-3.78 (m, 4H), 3.54-3.51 (m, 4H), 2.41 (s, 3H).

Example 104

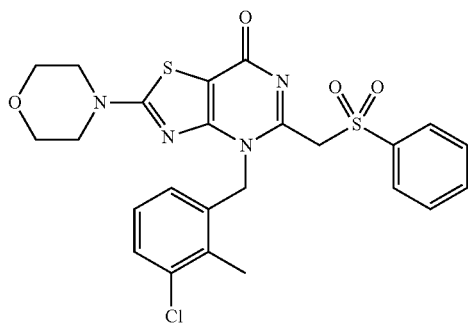 [SMILES: Cc1c(Cl)cccc1Cn1c(CS(=O)(=O)c2ccccc2)nc(=O)c2sc(N3CCOCC3)nc21]

Preparation of 4-[(3-chloro-2-methylphenyl)methyl]-2-(4-morpholinyl)-5-[(phenylsulfonyl)methyl][1,3]thiazolo[4,5-d]pyrimidin-7(4H)-one 4-[(3-chloro-2-methylphenyl)methyl]-2-(4-morpholinyl)-5-[(phenylthio)methyl][1,3]thiazolo[4,5-d]pyrimidin-7(4H)-one (37 mg, 0.074 mmol) in Acetic Acid (371 Ml) was added to a stirred suspension of sodiumperborate tetrahydrate (45.6 mg, 0.297 mmol) and Acetic Acid (371 μl). The mixture was stirred at room temperature overnight, and then concentrated. The residue was taken up in dichloromethane/water and eluted through a hydromatrix cartridge. The eluate was concentrated and purified by reversed-phase HPLC to provide 4-[(3-chloro-2-methylphenyl)methyl]-2-(4-morpholinyl)-5-[(phenylsulfonyl)methyl][1,3]thiazolo[4,5-d]pyrimidin-7(4H)-one. (8 mg, 20%); LC/MS: MS (ES$^+$) m/e 531 (MH$^+$); $^1$H NMR (400 MHz, DMSO-d$_6$) δ ppm 2.42 (s, 3H), 3.49-3.55 (m, 4H), 3.64-3.71 (m, 4H), 4.82 (s, 2H), 5.64 (s, 2H), 6.43 (d, J=7.6 Hz, 1H), 7.13 (m, 1H), 7.39 (d, J=7.83 Hz, 1H), 7.65 (t, J=7.8 Hz, 2H), 7.75-7.83 (m, 1H), 7.84-7.90 (m, 2H).

Example 105

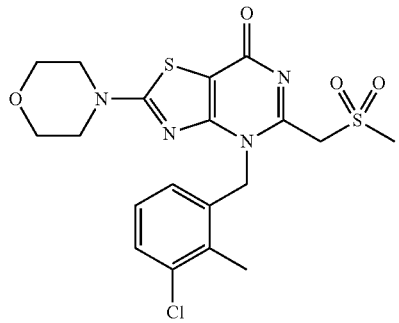 [SMILES: Cc1c(Cl)cccc1Cn1c(CS(C)(=O)=O)nc(=O)c2sc(N3CCOCC3)nc21]

Preparation of 4-[(3-chloro-2-methylphenyl)methyl]-5-[(methylsulfonyl)methyl]-2-(4-morpholinyl)[1,3]thiazolo[4,5-d]pyrimidin-7(4H)-one To a solution of 4-[(3-chloro-2-methylphenyl)methyl]-5-[(methylthio)methyl]-2-(4-morpholinyl)[1,3]thiazolo[4,5-d]pyrimidin-7(4H)-one (31 mg, 0.071 mmol) in Dichloromethane (DCM) (600 μl) was added m-CPBA (31.8 mg, 0.142 mmol) in Dichloromethane (DCM) (400 μl) at 0° C. After stirring at room temperature for 3 h, the solution was washed with 5% aqueous sodium hydrogen sulfite followed by saturated aqueous sodium bicarbonate. The organic layer was dried (sodium sulfate), filtered, and concentrated. The crude was purified by reversed-phase HPLC to provide 4-[(3-chloro-2-methylphenyl)methyl]-5-[(methylsulfonyl)methyl]-2-(4-morpholinyl)[1,3]thiazolo[4,5-d]pyrimidin-7(4H)-one. (14 mg, 42%); LC/MS: MS (ES$^+$) m/e 469 (MH$^+$); $^1$H NMR (400 MHz, DMSO-d$_6$) δ ppm 2.43 (s, 3H), 3.27 (s, 3H), 3.51-3.55 (m, 4H), 3.65-3.72 (m, 4H), 4.65 (s, 2H), 5.66 (s, 2H), 6.50 (d, J=7.8 Hz, 1H), 7.16 (m, 1H), 7.40 (d, J=8.1 Hz, 1H).

Example 106

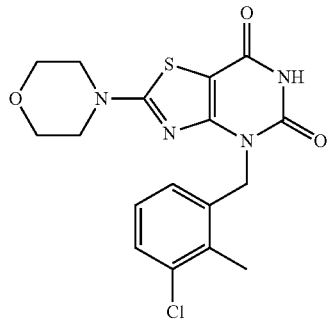 [SMILES: Cc1c(Cl)cccc1Cn1c(=O)[nH]c(=O)c2sc(N3CCOCC3)nc21]

Preparation of 4-[(3-chloro-2-methylphenyl)methyl]-2-(4-morpholinyl)[1,3]thiazolo[4,5-d]pyrimidine-5,7(4H,6H)-dione To a solution of 4-[(3-chloro-2-methylphenyl)methyl]-5-(methylthio)-2-(4-morpholinyl)[1,3]thiazolo[4,5-d]pyrimidin-7(4H)-one (25 mg, 0.059 mmol) in Dichloromethane (DCM) (500 μl) was added m-CPBA (13.25 mg, 0.059 mmol) in Dichloromethane (DCM) (300 μl) at 0° C. After stirring at room temperature for 3 h, the solution was washed with 5% aqueous sodium hydrogen sulfite followed by saturated aqueous sodium bicarbonate. The organic layer was dried (sodium sulfate), filtered, and concentrated. The crude was purified by reversed-phase HPLC to provide 4-[(3-chloro-2-methylphenyl)methyl]-2-(4-morpholinyl)[1,3]thiazolo[4,5-d]pyrimidine-5,7(4H,6H)-dione. (11 mg, 47%); LC/MS: MS (ES⁺) m/e 393 (MH⁺); ¹H NMR (400 MHz, DMSO-d₆) δ ppm 2.42 (s, 3H), 3.47-3.54 (m, 4H), 3.63-3.71 (m, 4H), 5.18 (s, 2H), 6.90 (d, J=7.3 Hz, 1H), 7.15 (m, 1H), 7.34 (d, J=7.3 Hz, 1H), 11.37 (s, 1H).

Scheme 11

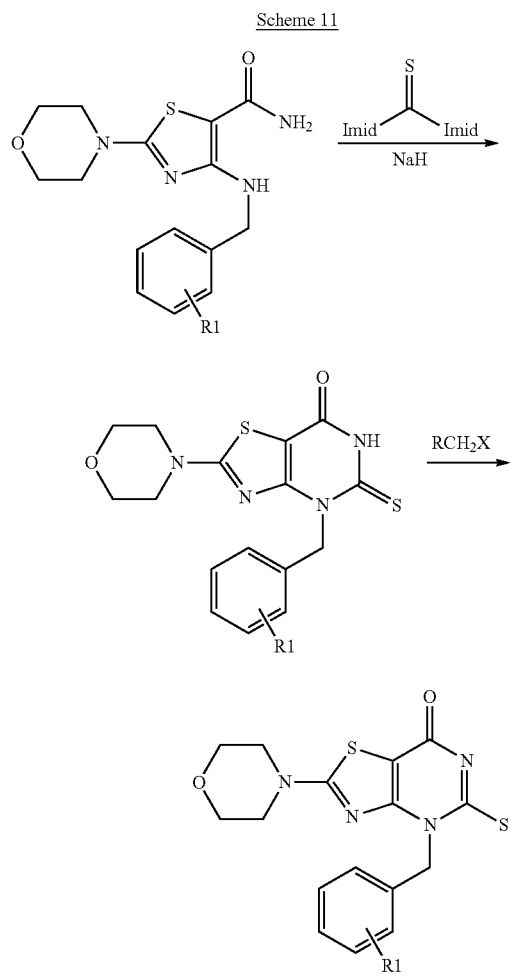

Example 107

Preparation of 4-[(3-chloro-2-methylphenyl)methyl]-2-(4-morpholinyl)-5-thioxo-5,6-dihydro[1,3]thiazolo[4,5-d]pyrimidin-7(4H)-one Sodium hydride (0.447 g, 17.71 mmol) was added portionwise to a suspension of 4-{[(3-chloro-2-methylphenyl)methyl]amino}-2-(4-morpholinyl)-1,3-thiazole-5-carboxamide (0.812 g, 2.213 mmol) and 1,1'-thiocarbonyldiimidazole (1.183 g, 6.64 mmol) in Tetrahydrofuran (THF) (20 mL). The mixture was stirred at rt for 2.5 days, then quenched by the dropwise addition of saturated NH₄Cl solution. The solvent was evaporated in vacuo and the residue was suspended in water. The pH was adjusted to about 6 by the addition of 1 N HCl. The yellowish orange solid was collected by filtration, washed with water, and dried in a vacuum oven at 65 C to provide 887 mg of the titled compound (98% yield). LC/MS: MS (ES⁺) m/e 409 (MH⁺)

Example 108

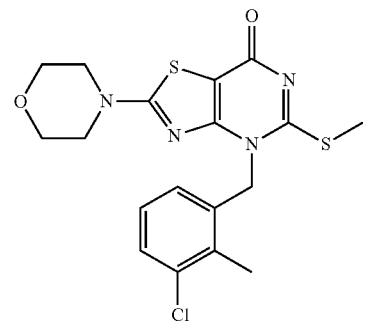 [SMILES: CSc1nc(=O)c2sc(N3CCOCC3)nc2n1Cc1cccc(Cl)c1C]

Preparation of 4-[(3-chloro-2-methylphenyl)methyl]-5-(methylthio)-2-(4-morpholinyl)[1,3]thiazolo[4,5-d]pyrimidin-7(4H)-one To a vial containing 4-[(3-chloro-2-methylphenyl)methyl]-2-(4-morpholinyl)-5-thioxo-5,6-dihydro[1,3]thiazolo[4,5-d]pyrimidin-7(4H)-one (25 mg, 0.061 mmol) in Tetrahydrofuran (THF) (607 μl) was added methyl iodide (4.20 μl, 0.067 mmol). The mixture was stirred at room temperature overnight then concentrated. The residue was purified by reversed-phase HPLC to provide 4-[(3-chloro-2-methylphenyl)methyl]-5-(methylthio)-2-(4-morpholinyl)[1,3]thiazolo[4,5-d]pyrimidin-7(4H)-one. (6 mg, 23%); LC/MS: MS (ES⁺) m/e 423 (MH⁺); ¹H NMR (400 MHz, DMSO-d₆) δ ppm 2.44 (s, 3H), 2.47 (s, 3H), 3.52 (m, 4H), 3.63-3.73 (m, 4H), 5.50 (s, 2H), 6.61 (d, J=7.6 Hz, 1H), 7.16 (m, 1H), 7.38 (d, J=7.8 Hz, 1H).

Example 109

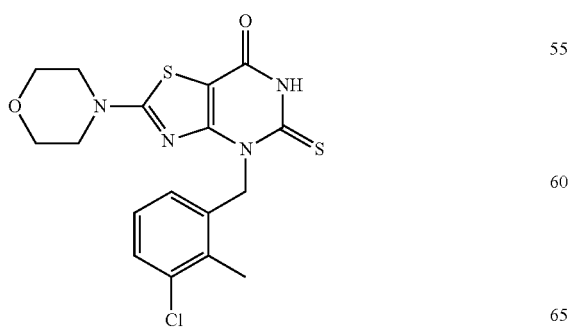

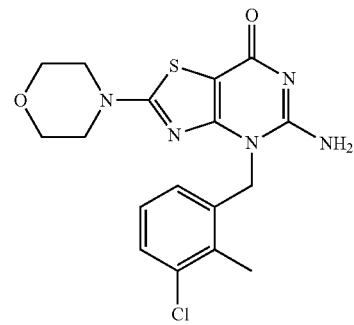 [SMILES: Cc1c(Cl)cccc1Cn1c(N)nc(=O)c2sc(N3CCOCC3)nc21]

Preparation of 5-amino-4-[(3-chloro-2-methylphenyl)methyl]-2-(4-morpholinyl)[1,3]thiazolo[4,5-d]pyrimidin-7(4H)-one 4-[(3-chloro-2-methylphenyl)methyl]-5-(methylthio)-2-(4-morpholinyl)[1,3]thiazolo[4,5-d]pyrimidin-7(4H)-one (500 mg, 1.182 mmol) in formamide (8 ml, 201 mmol) was heated at 192° C. and stirred for 1 h. The temperature was increased to 198° C. and stirring was continued for additional 3 h. After cooling, water was added in and the precipitate was collected, washed with water, then $Et_2O$ and dried to give 437 mg of crude. The material was purified by prep HPLC on a Kromasil Silica 5u 60 A 21×250 mm column, eluting with 95:5—$CHCl_3$:$CH_3OH$ (2M $NH_3$) at 20 mL/min and collecting fraction at about 7.2 min. 5-amino-4-[(3-chloro-2-methylphenyl)methyl]-2-(4-morpholinyl)[1,3]thiazolo[4,5-d]pyrimidin-7(4H)-one (151 mg, 0.380 mmol, 32.1% yield) was obtained from the crude as an off white powder. LC/MS (ES) m/z=392.1 (M+H); $^1$H NMR (400 MHz, DMSO-$d_6$) δ ppm 7.36 (d, J=7.83 Hz, 1H), 7.16 (t, J=7.96 Hz, 1H), 6.97 (s, 2H), 6.51 (d, J=7.58 Hz, 1H), 5.31 (s, 2H), 3.61-3.70 (m, 4H), 3.42 (t, J—=4.80 Hz, 4H), 2.38 (s, 3H)

Example 110

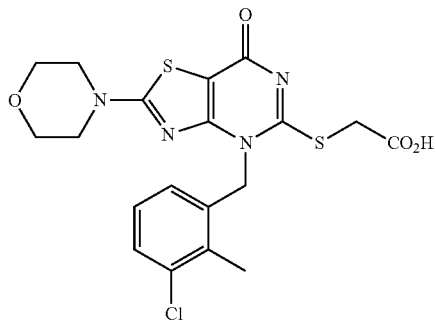 [SMILES: Cc1c(Cl)cccc1Cn1c(SCC(=O)O)nc(=O)c2sc(N3CCOCC3)nc21]

Preparation of {[4-[(3-chloro-2-methylphenyl)methyl]-2-(4-morpholinyl-7-oxo-4,7-dihydro[1,3]thiazolo[4,5-d]pyrimidin-5-yl]thio}acetic acid a) 1,1-dimethylethyl {[4-[(3-chloro-2-methylphenyl)methyl]-2-(4-morpholinyl)-7-oxo-4,7-dihydro[1,3]thiazolo[4,5-d]pyrimidin-5-yl]thio}acetate

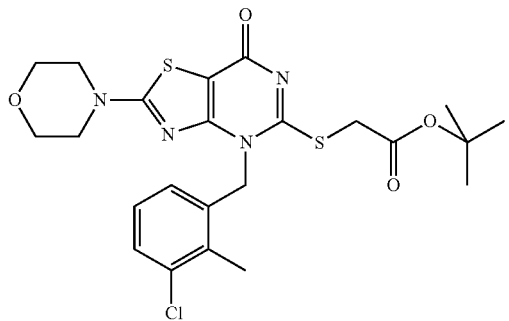 [SMILES: Cc1c(Cl)cccc1Cn1c(SCC(=O)OC(C)(C)C)nc(=O)c2sc(N3CCOCC3)nc21]

To a solution of 4-[(3-chloro-2-methylphenyl)methyl]-2-(4-morpholinyl)-5-thioxo-5,6-dihydro[1,3]thiazolo[4,5-d]pyrimidin-7(4H)-one (Example 107) (150 mg, 0.367 mmol) in N,N-Dimethylformamide (DMF) (2 mL) in a 20 mL Scintillation vial stirred at rt was added sodium hydride (27.8 mg, 1.100 mmol). After stirring at rt for 10 minutes, 1,1-dimethylethyl bromoacetate (0.108 mL, 0.734 mmol) was added and the reaction mixture was capped. Upon addition a precipitate immediately formed and the reaction mixture became a thick almost solid suspension. A portion of the solid was checked by LC/MS and it indicated that the reaction had gone about 80%. The reaction mixture was quenched with saturated $NH_4Cl$ solution and diluted with 15 mL water. The yellow-orange solid was isolated by filtration, washed with water and dried in a vacuum oven at 65 C for two hours providing 182 mg of solid that was used without further purification in the next step LC/MS (ES) m/z=524 (M+H).

b) {[4-[(3-chloro-2-methylphenyl)methyl]-2-(4-morpholinyl)-7-oxo-4,7-dihydro[1,3]thiazolo[4,5-d]pyrimidin-5-yl]thio}acetic acid To a solution of 1,1-dimethylethyl {[4-[(3-chloro-2-methylphenyl)methyl]-2-(4-morpholinyl)-7-oxo-4,7-dihydro[1,3]thiazolo[4,5-d]pyrimidin-5-yl]thio}acetate (182 mg, 0.348 mmol) in Dichloromethane (DCM) (2 mL) in a 20 mL Scintillation vial stirred at rt was added TFA (2 mL, 26.0 mmol). After sitting at rt for 5 hr LC/MS analysis indicated complete conversion to the acid. The DCM/TFA was removed in vacuo and the resulting residue was taken up in DCM. Attempts to extract the desired product into 1 N NaOH solution led to emulsions, so the pH was adjusted to 2 and the DCM layer was concentrated and to the residue was added water and the resultant solid was isolated by filtration and then purified by reverse phase prep HPLC on 30 mm prep column eluting with a gradient 25% to 55% AcCN over 12 minutes. LC/MS (ES) m/z=467 (M+H); $^1$H NMR (400 MHz, CDCl$_3$) δ ppm 7.35 (d, 1H), 7.09 (t, 1H), 6.61 (d, 1H), 5.56 (s, 2H), 4.01 (s, 2H), 3.83 (m, 4H), 3.59 (m, 4H), 2.49 (s, 3H).

Scheme 12

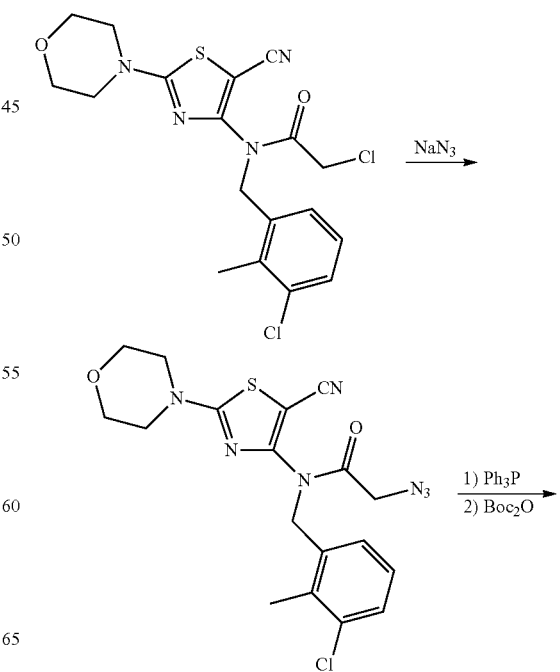

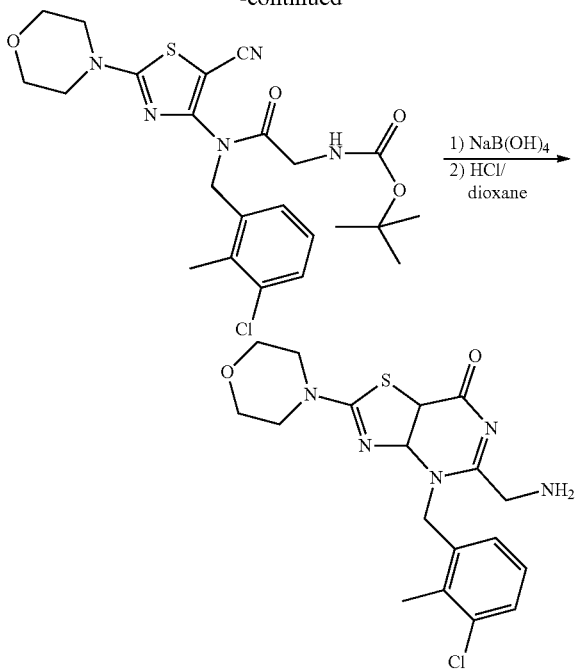

Example 111

Preparation of 5-(aminomethyl)-4-[(3-chloro-2-methylphenyl)methyl]-2-(4-morpholinyl)[1.3]thiazolo[4,5-d]pyrimidin-7(4H)-one a) 2-azido-N-[(3-chloro-2-methylphenyl)methyl]-N-[5-cyano-2-(4-morpholinyl)-1,3-thiazol-4-yl]acetamide

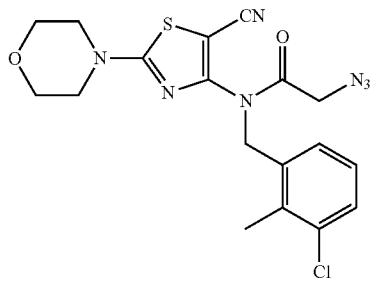 [SMILES: Cc1c(Cl)cccc1CN(C(=O)CN=[N+]=[N-])c1nc(N2CCOCC2)sc1C#N]

To a solution of 2-chloro-N-[(3-chloro-2-methylphenyl)methyl]-N-[5-cyano-2-(4-morpholinyl)-1,3-thiazol-4-yl]acetamide (200 mg, 0.470 mmol) (prepared according to the procedures of example 59) in N,N-Dimethylformamide (DMF) (2 mL) was added sodium azide (92 mg, 1.410 mmol) at rt. The mixture was stirred at rt for 3 hr before diluted in 100 ml EtOAc and washed with 20 mL H₂O twice. The organic layer was concentrated to give 200 mg crude product (99%), which was used in the next step without further purification. LC/MS (ES) m/z=432.2 (M+H).

b) 1,1-dimethylethyl (2-{[(3-chloro-2-methylphenyl)methyl][5-cyano-2-(4-morpholinyl)-1,3-thiazol-4-yl]amino})-2-oxoethyl)carbamate

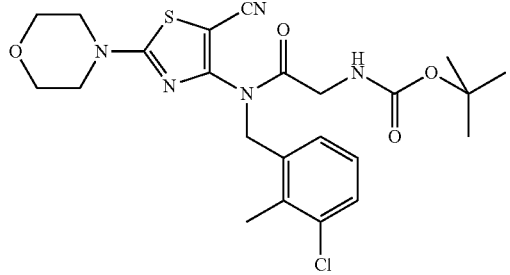 [SMILES: Cc1c(Cl)cccc1CN(C(=O)CNC(=O)OC(C)(C)C)c1nc(N2CCOCC2)sc1C#N]

To a solution of 2-azido-N-[(3-chloro-2-methylphenyl)methyl]-N-[5-cyano-2-(4-morpholinyl)-1,3-thiazol-4-yl]acetamide (300 mg, 0.695 mmol) in Tetrahydrofuran (THF) (20 mL) and H₂O (2 mL) was added Ph₃P (547 mg, 2.084 mmol). The mixture was stirred at rt for 5 hr before removal of the solvent. To the residue was added 50 mL DCM and 20 mL NaHCO₃ (sat.), followed by Boc₂O (0.323 mL, 1.389 mmol). The mixture was stirred at rt for 17 hrs. The organic layer was concentrated and purified on a silica column to give the titled compound 150 mg. (43%) LC/MS (ES) m/z=505.9 (M+H).

c) 5-(aminomethyl)-4-[(3-chloro-2-methylphenyl)methyl]-2-(4-morpholinyl)[1,3]thiazolo[4,5-d]pyrimidin-7(4H)-one To a solution of 1,1-dimethylethyl (2-{[(3-chloro-2-methylphenyl)methyl][5-cyano-2-(4-morpholinyl)-1,3-thiazol-4-yl]amino}-2-oxoethyl)carbamate (150 mg, 0.296 mmol) in Methanol (5 mL) and Water (5.00 mL) was added sodium perborate tetrahydrate (137 mg, 0.889 mmol). The mixture was stirred at 55° C. for 2 hr and then diluted in 100 mL EtOAc. After washed with 100 mL H₂O, the organic layer was concentrated and diluted in 10 mL DCM, to which was added 4M HCl in dioxane (0.371 mL, 1.482 mmol). The mixture was stirred at rt for 17 hr. One fourth of the crude material was purified by HPLC and then treated with HCl (6N) to give the titled compound 9 mg (26%). LC/MS (ES) m/z=406.4 (M+H); ¹H NMR (400 MHz, MeOD) δ ppm 7.42-7.40 (d, 1H, J=8.0 Hz), 7.18-7.12 (m, 1H), 6.55 (d, 1H, J=8.0 Hz), 5.65 (s, 2H), 4.21 (s, 2H), 3.79-3.76 (m, 4H), 3.68-3.62 (m, 4H), 2.52 (s, 3H).

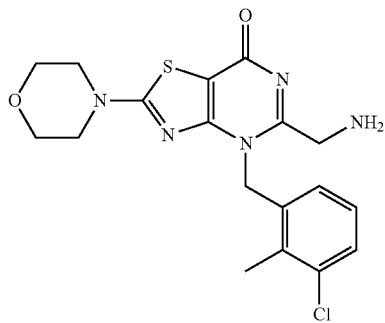

Scheme 13

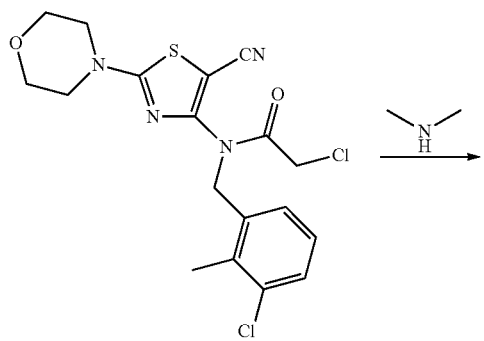

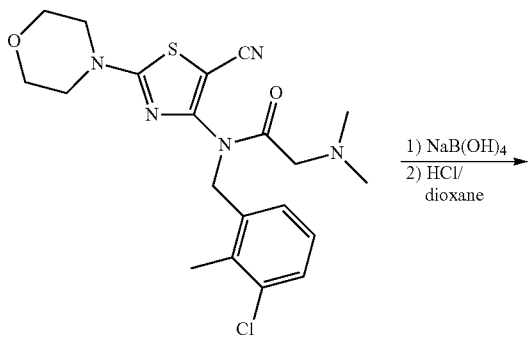

Example 112

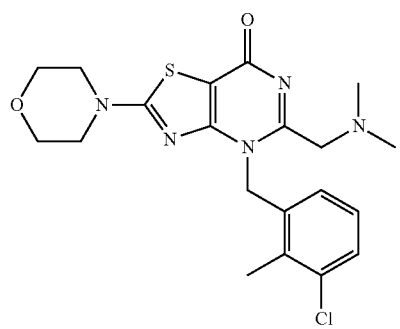 [SMILES: Cc1c(Cl)cccc1Cn1c(CN(C)C)nc(=O)c2sc(N3CCOCC3)nc21]

Preparation of 4-[(3-chloro-2-methylphenyl)methyl]-5-[(dimethylamino)methyl]-2-(4-morpholinyl)[1,3]thiazolo[4,5-d]pyrimidin-7(4H)-one a) $N^1$-[(3-chloro-2-methylphenyl)methyl]-$N^1$-[5-cyano-2-(4-morpholinyl)-1,3-thiazol-4-yl]-$N^2,N^2$-dimethylglycinamide

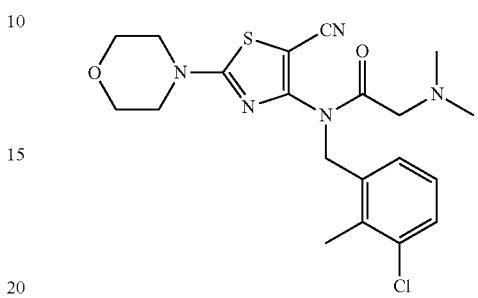

To a solution of 2-chloro-N-[(3-chloro-2-methylphenyl)methyl]-N-[5-cyano-2-(4-morpholinyl)-1,3-thiazol-4-yl]acetamide (100 mg, 0.235 mmol) (prepared according to the procedures of example 111) in N,N-Dimethylformamide (DMF) (2 mL) was added dimethyl amine (0.588 mL, 1.176 mmol). The mixture was heated in a microwave reactor at 120° C. for 30 mins. The resultant mixture was diluted in EtOAc (100 mL) and washed with H$_2$O (100 ml×2). The organic layer was concentrated to afford the crude product, which was use in next step without further purification. (88%)

b) 4-[(3-chloro-2-methylphenyl)methyl]-5-[(dimethylamino)methyl]-2-(4-morpholinyl)[1,3]thiazolo[4,5-d]pyrimidin-7(4H)-one To a solution of N1-[(3-chloro-2-methylphenyl)methyl]-N1-1-[5-cyano-2-(4-morpholinyl)-1,3-thiazol-4-yl]-N2,N2-dimethylglycinamide (50 mg, 0.115 mmol) in Methanol (2.0 mL) and Water (2 mL) was added Sodium Perborate Tetrahydrate (53.2 mg, 0.346 mmol) at rt. The mixture was heated at 50° C. for 3 hr. The mixture was diluted in 50 ml EtOAc and washed with H$_2$O (20 ml). The organic layer was concentrated and purified on reverse phase HPLC to give the titled compound 18 mg. (34%) LCMS (ES) m/z=434.3 (M+H); $^1$H NMR (400 MHz, MeOD) δ ppm 7.41-7.39 (d, 1H, J=8.0 Hz), 7.18-7.12 (m, 1H), 6.76 (d, 1H, J=7.6 Hz), 5.61 (s, 2H), 4.51 (s, 2H), 3.78-3.75 (m, 4H), 3.68-3.62 (m, 4H), 3.01 (s, 6H), 2.52 (s, 3H).

Example 113

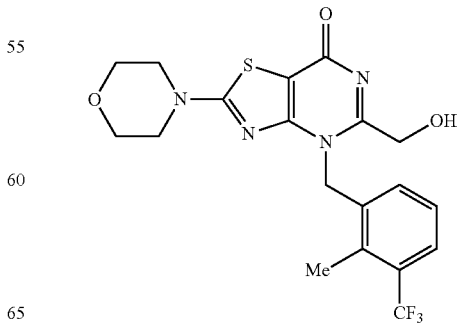

Preparation of 5-(hydroxymethyl)-4-{[2-methyl-3-(trifluoromethyl)phenyl]methyl}-2-(4-morpholinyl)[1,3]thiazolo[4,5-d]pyrimidin-7(4H)-one a) [4-{[2-methyl-3-(trifluoromethyl)phenyl]methyl}-2-(4-morpholinyl)-7-oxo-4,7-dihydro[1,3]thiazolo[4,5-d]pyrimidin-5-yl]methyl acetate

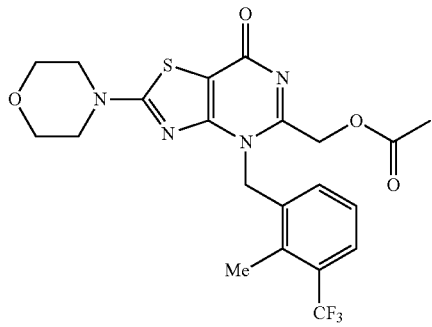 [SMILES: CC(=O)OCc1nc(=O)c2sc(N3CCOCC3)nc2n1Cc1cccc(C(F)(F)F)c1C]

A solution of 4-({[2-methyl-3-(trifluoromethyl)phenyl]methyl}amino)-2-(4-morpholinyl)-1,3-thiazole-5-carboxamide (300 mg, 0.749 mmol), 2-chloro-2-oxoethyl acetate (0.201 mL, 1.873 mmol) in Tetrahydrofuran (THF) (6 mL) was charged into a sealed tube under 0 C. The mixture was warmed up to RT gradually. The reaction was stirred at RT for overnight. The mixture was partitioned between DCM and NaCl, the organic layer was concentrated and the residue was purified on silica column (5% MeOH/DCM) to give product 80 mg (~20%).

5-(hydroxymethyl)-4-{[2-methyl-3-(trifluoromethyl)phenyl]methyl}-2-(4-morpholinyl)[1,3]thiazolo[4,5-d]pyrimidin-7(4H)-one Sodium hydroxide (0.166 mL, 0.166 mmol) was added to a solution of [4-{[2-methyl-3-(trifluoromethyl)phenyl]methyl}-2-(4-morpholinyl)-7-oxo-4,7-dihydro[1,3]thiazolo[4,5-d]pyrimidin-5-yl]methyl acetate (80 mg, 0.166 mmol) in Methanol (1.5 mL). The reaction was stirred at RT for 30 min. 1N HCl was added to adjust to pH=5. The mixture was partitioned between DCM and NaCl solution. The organic layer was concentrated to give the titled compound, 65 mg (90%). LC/MS (ES) m/z 441.0 (M+H)+, 1H NMR (400 MHz, DMSO-d6) δ ppm 7.65 (m, 1H), 7.36 (m, 1H), 6.87 (m, 1H), 5.60 (s, 2H), 4.15 (m, 2H), 3.66 (m, 4H), 3.56 (m, 4H), 2.49 (s, 3H)

Example 114

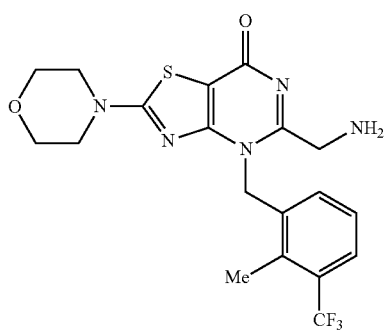 [SMILES: Cc1c(Cn2c(CN)nc(=O)c3sc(N4CCOCC4)nc32)cccc1C(F)(F)F]

Preparation of 5-(aminomethyl)-4-{[2-methyl-3-(trifluoromethyl)phenyl]methyl}-2-(4-morpholinyl)[1,3]thiazolo[4,5-d]pyrimidin-7(4H)-one a) 2-{[4-{[2-methyl-3-(trifluoromethyl)phenyl]methyl}-2-(4-morpholinyl)-7-oxo-4,7-dihydro[1,3]thiazolo[4,5-d]pyrimidin-5-yl]methyl}-1H-isoindole-1,3(2H)-dione

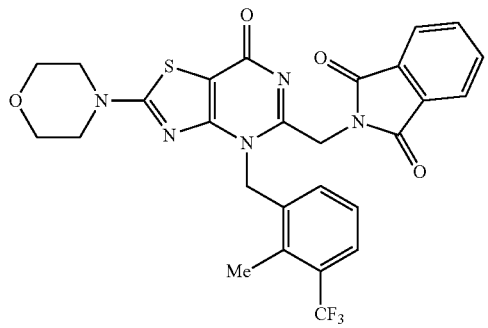 [SMILES: Cc1c(Cn2c(CN3C(=O)c4ccccc4C3=O)nc(=O)c3sc(N4CCOCC4)nc32)cccc1C(F)(F)F]

DEAD (0.035 mL, 0.221 mmol) was added to a solution of 5-(hydroxymethyl)-4-{[2-methyl-3-(trifluoromethyl)phenyl]methyl}-2-(4-morpholinyl)[1,3]thiazolo[4,5-d]pyrimidin-7(4H)-one (Example 113, 65 mg, 0.148 mmol), 1H-isoindole-1,3(2H)-dione (26.1 mg, 0.177 mmol) and triphenylphosphine (58.1 mg, 0.221 mmol) in Tetrahydrofuran (THF) (2 mL). The reaction was stirred at RT for overnight. The mixture was partitioned between DCM and NaCl solution, the organic layer was dried over MgSO4 and was concentrated. The residue was purified on a silica column eluting with 30% EtOAc/Hexanes to give the titled product, 60 mg (60%).

b) 5-(aminomethyl)-4-{[2-methyl-3-(trifluoromethyl)phenyl]methyl}-2-(4-morpholinyl)[1,3]thiazolo[4,5-d]pyrimidin-7(4H)-one Hydrazine (3.31 μL, 0.105 mmol) was added to a solution of 2-{[4-{[2-methyl-3-(trifluoromethyl)phenyl]methyl}-2-(4-morpholinyl)-7-oxo-4,7-dihydro[1,3]thiazolo[4,5-d]pyrimidin-5-yl]methyl}-1H-isoindole-1,3(2H)-dione (60 mg, 0.105 mmol) in Methanol (2 mL). The mixture was stirred at RT for 2 hours. The solvent was removed and the residue was purified by reverse phase HPLC (10% org~50% org) to give the titled product 16 mg (35%). LC/MS (ES) m/z 440.1 (M+H)+, 1H NMR (400 MHz, DMSO-d6) δ ppm 8.30 (br, s, 2H), 7.67 (m, 1H), 7.38 (m, 1H), 6.87 (m, 1H), 5.58 (s, 2H), 4.20 (m, 2H), 3.66 (m, 4H), 3.56 (m, 4H), 2.37 (s, 3H)

Example 115

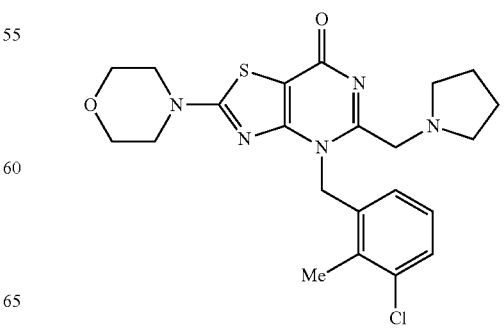

Preparation of 4-[(3-chloro-2-methylphenyl)methyl]-2-(4-morpholinyl)-5-(1-pyrrolidinylmethyl)[1,3]thiazolo[4,5-d]pyrimidin-7(4H)-one a) 5-(bromomethyl)-4-[(3-chloro-2-methylphenyl)methyl]-2-(4-morpholinyl)[1,3]thiazolo[4,5-d]pyrimidin-7(4H)-one

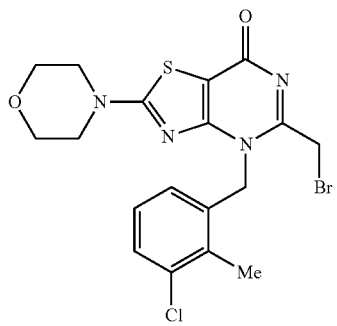 [SMILES: Cc1c(Cl)cccc1Cn1c(CBr)nc(=O)c2sc(N3CCOCC3)nc21]

To a 40 mL I-CHEM reaction vial equipped with a stirbar, was added Example 60, 4-[(3-chloro-2-methylphenyl)methyl]-5-methyl-2-(4-morpholinyl)[1,3]thiazolo[4,5-d]pyrimidin-7(4H)-one (1 g, 2.56 mmol), N-bromosuccinimide (0.569 g, 3.20 mmol), and 2,2'-azobis(2-methylpropionitrile) (0.084 g, 0.512 mmol). The solids were taken up in tetrahydrofuran (THF) (25.6 ml) and stirred overnight at room temperature. After overnight stirring, the reaction was diluted with water (~10 mL) transferred to a separatory funnel and extracted with dichloromethane DCM (~50 mL). The organic layer was dried over sodium sulfate and concentrated to a residue. The residue was re-dissolved in a minimum amount of DCM (~2 mL) and injected onto a 25 g SNAP silica cartridge for purification (eluting with a gradient: 5%-75% THF (1% methanol (MeOH)) into DCM, over 30 column volumes). Fractions containing the desired material were pooled and concentrated to afford 5-(bromomethyl)-4-[(3-chloro-2-methylphenyl)methyl]-2-(4-morpholinyl)[1,3]thiazolo[4,5-d]pyrimidin-7(4H)-one (752 mg, 1.601 mmol, 62.6% yield). LC/MS Theoretical m/z MH$^+$=470.78 Found: 470.8; $^1$H NMR (400 MHz, DMSO-d$_6$) δ ppm 2.45 (s, 3H) 3.46-3.56 (m, 4H) 3.66 (t, J=4.93 Hz, 5H) 4.46 (s, 2H) 5.58 (s, 2H) 6.53 (d, J=8.08 Hz, 1H) 7.14 (t, J=7.96 Hz, 1H) 7.37 (d, J=7.83 Hz, 1H).

b) 4-[(3-chloro-2-methylphenyl)methyl]-2-(4-morpholinyl)-5-(1-pyrrolidinylmethyl)[1,3]thiazolo-[4,5-d]pyrimidin-7(4H)-one To a 20 mL I-CHEM reaction vial was added a solution of 5-(bromomethyl)-4-[(3-chloro-2-methylphenyl)methyl]-2-(4-morpholinyl)[1,3]thiazolo[4,5-d]pyrimidin-7(4H)-one (188 mg, 0.400 mmol) in tetrahydrofuran (THF) (4002 μL). The solution was then treated with pyrrolidine (331 μL, 4.00 mmol) and the resulting reaction mixture was allowed to stir at room temperature and was found to have completely converted to the desired material by LCMS in less than 5 minutes. Reaction mixture was placed under a nitrogen stream and warmed to 50° C. to concentrate the reaction to a residue. The residue was then re-dissolved in dichloromethane (DCM) (750 μL) and injected onto a 10 g SNAP silica cartridge for purification [eluting with a gradient: 0-95% THF (1% methanol (MeOH)) into DCM, over 30 column volumes]. Fractions containing the desired material were pooled and concentrated to afford a residue which was subsequently triturated with ethyl acetate and hexanes to afford pure 4-[(3-chloro-2-methylphenyl)methyl]-2-(4-morpholinyl)-5-(1-pyrrolidinylmethyl)[1,3]thiazolo[4,5-d]pyrimidin-7(4H)-one (38 mg, 0.082 mmol, 20.44% yield). LCMS Theoretical m/z MH$^+$=460.99 Found: 461.2; $^1$H NMR (400 MHz, DMSO-d$_6$) δ ppm 1.47 (br. s., 4H) 2.37 (br. s., 4H) 2.41 (s, 3H) 3.46-3.52 (m, 4H) 3.52 (s, 2H) 3.62-3.74 (m, 4H) 5.66 (s, 2H) 6.45 (d, J=7.83 Hz, 1H) 7.11 (t, J=8.21 Hz, 1H) 7.33 (d, J=7.33 Hz, 1H).

Example 116

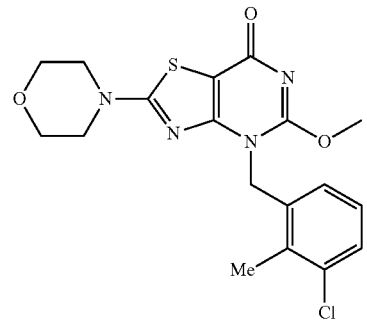 [SMILES: COc1nc(=O)c2sc(N3CCOCC3)nc2n1Cc1cccc(Cl)c1C]

Preparation of 4-[(3-chloro-2-methylphenyl)methyl]-5-(methyloxy)-2-(4-morpholinyl)[1,3]thiazolo[4,5-d]primidin-7(4H)-one a) 4-[(3-chloro-2-methylphenyl)methyl]-5-(methylthio)-2-(4-morpholinyl)[1,3]thiazolo[4,5-d]pyrimidin-7(4H)-one

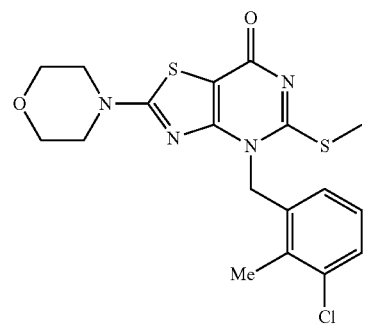

Sodium hydride (2.62 g, 65.4 mmol) was added portionwise to a suspension of 4-{[(3-chloro-2-methylphenyl)methyl]amino}-2-(4-morpholinyl)-1,3-thiazole-5-carboxamide (3 g, 8.18 mmol) and 1,1'-thiocarbonyldiimidazole (4.37 g, 24.53 mmol) in Tetrahydrofuran (THF) (80 mL). The mixture was stirred at rt for 21 h, then quenched by the dropwise addition of water. The solvent was evaporated and the residue was suspended in water. The pH was adjusted to about 7 by the addition of 6 N HCl, while cooling in an ice bath. The yellow solid was collected by filtration, washed with water, then hexanes and dried. The solid obtained was suspended in Tetrahydrofuran (THF) (80 mL) and treated with iodomethane (0.562 mL, 9.00 mmol). After few hours minimal conversion was observed by LC/MS. Sodium carbonate (1.300 g, 12.27 mmol) and additional iodomethane (0.562 mL, 9.00 mmol) were added and stirring was continued overnight. LC/MS analysis showed that the reaction was still not complete. Additional sodium carbonate (1.300 g, 12.27 mmol) and iodomethane (0.562 mL, 9.00 mmol) were added and the mix was warmed at 45° C. for 4 h (an additional aliquot of sodium carbonate and iodomethane were added during this time). The reaction has stalled and only reached about 40% conversion. It was then cooled to rt, the solvent was evaporated and the residue was suspended in water. The pH was neutralized by the addition of 6 N HCl. The solid was collected, washed with water and dried. The dry solid obtained was suspended in N,N-Dimethylformamide (DMF) (35 mL). Potassium carbonate (3.96 g, 28.6 mmol) and iodomethane (1.534 mL, 24.53 mmol) were added and the mixture was stirred at 50° C. for 1.5 h. After cooling, it was poured into ice/water and the precipitate formed was collected, washed with water and dried to afford 4-[(3-chloro-2-methylphenyl)methyl]-5-(methylthio)-2-(4-morpholinyl)[1,3]thiazolo[4,5-d]pyrimidin-7(4H)-one (2.27 g, 5.37 mmol, 65.6% yield) which was used in the next step without further purification. LC/MS (ES+): [M+H]+=422.9 (80% pure). $^1$H NMR (400 MHz, DMSO-d$_6$) δ ppm 7.37 (d, J=7.83 Hz, 1H), 7.15 (t, J=7.83 Hz, 1H), 6.60 (d, J=7.33 Hz, 1H), 5.49 (s, 2H), 3.63-3.72 (m, 4H), 3.52 (d, J=4.55 Hz, 4H), 2.46 (s, 3H), 2.43 (s, 3H).

b) 4-[(3-chloro-2-methylphenyl)methyl]-5-(methyloxy)-2-(4-morpholinyl)[1,3]thiazolo[4,5-d]pyrimidin-7(4H)-one A mixture of 4-[(3-chloro-2-methylphenyl)methyl]-5-(methylthio)-2-(4-morpholinyl)[1,3]thiazolo[4,5-d]pyrimidin-7(4H)-one (500 mg, 1.182 mmol) and sodium perborate tetrahydrate (700 mg, 3.85 mmol) in Methanol (5 mL) was irradiated in a microwave reactor at 110° C. for 15 min. The reaction was repeated three additional times. The four reaction mixtures were poured into brine and extracted with CH$_2$Cl$_2$ (4×). The combined organic extracts were washed with brine, dried over Na$_2$SO$_4$ and evaporated. The residue was purified on silica gel (ISCO, 0-7% MeOH in CH$_2$Cl$_2$), but separation failed. The fractions containing product were combined, absorbed onto silica gel and resubmitted for purification on silica gel (ISCO, 0-5% MeOH in CH$_2$Cl$_2$), but again no separation was observed. The residues from the combined fractions were finally purified using Chiralpak IA (101×210 mm, 100% CH$_3$OH, 500 ml/min) to give 4-[(3-chloro-2-methylphenyl)methyl]-5-(methyloxy)-2-(4-morpholinyl)[1,3]thiazolo[4,5-d]pyrimidin-7(4H)-one (820 mg, 1.995 mmol, 42.2% yield) as a white powder. LC/MS (ES+): [M+H]+=407.3. $^1$H NMR (400 MHz, DMSO-d$_6$) δ ppm 7.36 (d, J=7.83 Hz, 1H), 7.15 (t, J=7.83 Hz, 1H), 6.72 (d, J=7.58 Hz, 1H), 5.34 (s, 2H), 3.85 (s, 3H), 3.60-3.74 (m, 4H), 3.51 (t, J=4.67 Hz, 4H), 2.41 (s, 3H).

Example 117

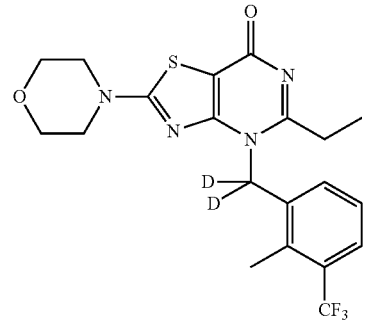 [SMILES: [2H]C([2H])(c1cccc(C(F)(F)F)c1C)n1c(CC)nc(=O)c2sc(N3CCOCC3)nc21]

Preparation of 5-ethyl-4-{[2-methyl-3-(trifluoromethyl)phenyl]methyl}-2-(4-morpholinyl)[1,3]thiazolo[4,5-d]primidin-7(4H)-one-d$_2$ a) methyl 2-methyl-3-(trifluoromethyl)benzoate

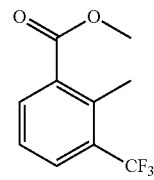

To a 500 mL round bottom equipped with an Airflux Condenser and stir bar was added 2-methyl-3-(trifluoromethyl)benzoic acid (30 g, 147 mmol). The solid was taken up in Methanol (101 ml) and to that solution was slowly added sulfuric acid (8.22 ml, 154 mmol). The reaction was then fitted with the condenser and heated to 75° C. overnight. The reaction was cooled back to room temperature, and neutralized by slow addition of 1N NaOH (~155 mL). The solution was then extracted with 3×300 mL Et$_2$O, the organic layer dried over magnesium sulfate, and concentrated to an oil, which solidified under vacuum to give off white solid methyl 2-methyl-3-(trifluoromethyl)benzoate (28.25 g, 129 mmol, 88% yield) $^1$H NMR (400 MHz, DMSO-d$_6$) δ ppm 2.54 (d, J=1.77 Hz, 3H) 3.89 (s, 3H) 7.53 (t, J=7.83 Hz, 1H) 7.89 (d, J=7.83 Hz, 1H) 7.97 (d, J=7.83 Hz, 1H).

b) [2-methyl-3-(trifluoromethyl)phenyl]methanol-d$_2$

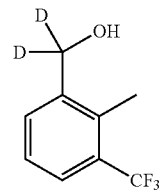

To a 1 L round bottom flask equipped with a stir bar, nitrogen lines, and pressure equalizing addition funnel, was added lithium aluminum deuteride (LAD) (12 g, 286 mmol). The solid material was taken up in anhydrous tetrahydrofuran (THF) (268 ml) and the resulting suspension placed under a nitrogen atmosphere and the temperature lowered to 0° C. The addition funnel was then charged with a solution of methyl 2-methyl-3-(trifluoromethyl)benzoate (27 g, 124 mmol) in anhydrous tetrahydrofuran (THF) (107 ml), and the substrate was slowly added, drop-wise, to the LAD suspension over approximately minutes. Upon complete addition, the funnel was removed and the inert atmosphere maintained. The reaction temperature was allowed to warm naturally to ambient over 2 hours with vigorous stirring. The reaction was then quenched with a modified Fieser and Fieser workup (adjusting by multiplying normal lithium aluminum hydride reduction workup amount by 0.8564) by sequential addition of the following: 10.277 mL water, 10.277 mL of 15 wt % NaOH (aq.) solution, and 30.83 mL water. The resulting mixture was stirred at room temperature for 1 hour to allow the precipitate to form and was then filtered, followed by concentration of the solution, in vacuo, to afford a gel. The gel was suspended in dichloromethane and transferred to a 100 mL round bottom flask. The material was concentrated to a gel and then subjected to high vacuum to afford [2-methyl-3-(trifluoromethyl)phenyl]methanol-$d_2$ (21.883 g, 114 mmol, 92% yield) as a white solid $^1$H NMR (400 MHz, DMSO-$d_6$) δ ppm 2.33 (d, J=1.52 Hz, 3H) 5.26 (s, 1H) 7.37 (t, J=7.71 Hz, 1H) 7.57 (d, J=7.83 Hz, 1H) 7.67 (d, J=7.83 Hz, 1H).

c) 1-(bromomethyl)-2-methyl-3-(trifluoromethyl)benzene-$d_2$

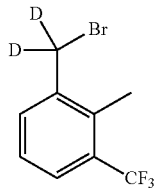

To a 500 mL round bottom flask containing a stirred solution of [2-methyl-3-(trifluoromethyl)phenyl]methanol-$d_2$ (20 g, 104 mmol) in Dichloromethane (DCM) [for substrate](312 ml) at 0° C., was slowly added a solution of PBr$_3$ (3.93 ml, 41.6 mmol) in Dichloromethane (DCM) [for PBr$_3$](104 ml), dropwise by pressure equalizing addition funnel, under nitrogen atmosphere. Upon complete addition of the reagent, the addition funnel was removed and the reaction allowed to warm naturally to room temperature overnight. The reaction was then shut down and extracted briefly with saturated sodium bicarbonate (aq.) solution (250 mL). The organic layer was dried over sodium sulfate and concentrated to an oil suitable for use in the next step 1-(bromomethyl)-2-methyl-3-(trifluoromethyl)benzene-$d_2$ (21.708 g, 85 mmol, 82% yield) $^1$H NMR (400 MHz, DMSO-$d_6$) δ ppm 2.45 (d, J=1.52 Hz, 3H) 7.33-7.42 (m, 1H) 7.64 (d, J=7.83 Hz, 1H) 7.72 (d, J=7.58 Hz, 1H).

d) N-[5-cyano-2-(4-morpholinyl)-1,3-thiazol-4-yl]-N-{[2-methyl-3-(trifluoromethyl)phenyl]methyl}propanamide-$d_2$

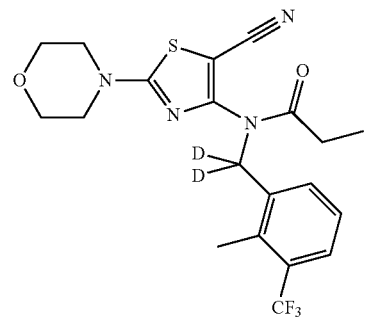 [SMILES: [2H]C([2H])(c1cccc(C(F)(F)F)c1C)N(C(=O)CC)c1nc(N2CCOCC2)sc1C#N]

To a 40 mL reaction vial equipped with a stirbar was added previously prepared (for the synthesis of GSK2355756A) N-[5-cyano-2-(4-morpholinyl)-1,3-thiazol-4-yl]propanamide (1 g, 3.75 mmol) and potassium carbonate (1.038 g, 7.51 mmol). The solids were taken up in N,N-Dimethylformamide (DMF) (7.51 ml) and to this suspension was added 1-(bromomethyl)-2-methyl-3-(trifluoromethyl)benzene-$d_2$ (0.958 g, 3.75 mmol). The resulting reaction mixture was immediately heated to 100° C., thermally, and stirred for 2 hours. The reaction appeared to be almost complete and was beginning to show conversion to the ring-closed material by LC/MS (and some of the ring opened hydrated carboxamide). 5 additional drops of bromide (~100 L) were then added and heating continued to complete conversion of the starting material to the alkylated product. Once LC/MS showed complete conversion to either the ring-opened alkylated or ring-closed alkylated product, the reaction was then cooled to room temperature, partitioned between water and EtOAc, and extracted. The organic layer was dried over sodium sulfate and concentrated to a residue. The reaction was considered quantitative and the material was carried through to the next step without further purification.

e) 5-ethyl-4-{[2-methyl-3-(trifluoromethyl)phenyl]methyl}-2-(4-morpholinyl)[1,3]thiazolo[4,5-d]pyrimidin-7(4H)-one-$d_2$ To a 40 mL reaction vial equipped with a stir bar was added a solution of N-[5-cyano-2-(4-morpholinyl)-1,3-thiazol-4-yl]-N-{[2-methyl-3-(trifluoromethyl)phenyl]methyl}propanamide-$d_2$ (1.65 g, 3.75 mmol) in methanol (8.32 ml) and tetrahydrofuran (THF) (8.32 ml). The solution was then diluted with water (8.32 ml) and treated with potassium carbonate (1.035 g, 7.49 mmol) and sodium perborate tetrahydrate (0.919 g, 11.24 mmol). The resulting reaction mixture was stirred overnight at 55° C. The reaction was found to be complete by LCMS and was removed from heat. After cooling to room temperature, the reaction mixture was partitioned between ethyl acetate and water and extracted. The organic layer was dried over sodium sulfate and concentrated to a semi-solid residue. That material was triturated with a minimum amount (~2 mL) of ethyl acetate to afford a canary yellow solid, which was subsequently re-crystallized from 10:1:1 mix of DCM:EtOAc:MeOH via slow addition of Hexanes. The solid was dried overnight under vacuum at room temperature to afford the titled compound 5-ethyl-4-{[2-methyl- 3-(trifluoromethyl)phenyl]methyl}- 2-(4-morpholinyl)[1,3]thiazolo[4,5-d]pyrimidin-7(4H)-one-d$_2$ (393 mg, 0.892 mmol, 23.82% yield) as a white solid $^1$H NMR (400 MHz, DMSO-d$_6$) δ ppm 1.11 (t, J=7.20 Hz, 3H) 2.50 (s, 3H) 2.59 (q, J=7.24 Hz, 2H) 3.42-3.58 (m, 4H) 3.59-3.74 (m, 4H) 6.82 (d, J=7.58 Hz, 1H) 7.34 (t, J=7.83 Hz, 1H) 7.63 (d, J=7.58 Hz, 1H).

Example 118

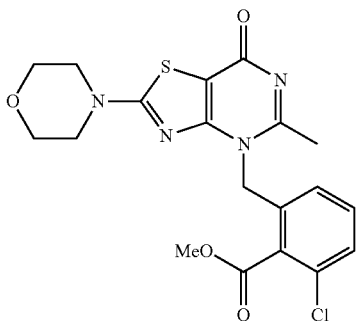 [SMILES: COC(=O)c1c(Cl)cccc1Cn1c(C)nc(=O)c2sc(N3CCOCC3)nc21]

The preparation of methyl 2-chloro-6-{5-methyl-2-(4-morpholinyl)-7-oxo[1,3]thiazolo[4,5-d]pyrimidin-4(7H)-yl]methyl}benzoate The titled compound was prepared following the same procedure as Example 59 replacing 1-(bromomethyl)-2-methyl-3-(trifluoromethyl)benzene with methyl 2-(bromomethyl)-6-chlorobenzoate as the alkylating agent. LC/MS (ES) m/z 435.1 (M+H)$^+$, $^1$H NMR (400 MHz, DMSO-d$_6$) δ ppm 7.43-7.41 (m, 1H), 7.35-7.28 (m, 1H), 6.73-6.71 (m, 1H), 5.47 (s, 2H), 4.03 (s, 3H), 3.82-3.80 (m, 4H), 3.60-3.57 (m, 4H), 2.44 (s, 3H).

Example 119

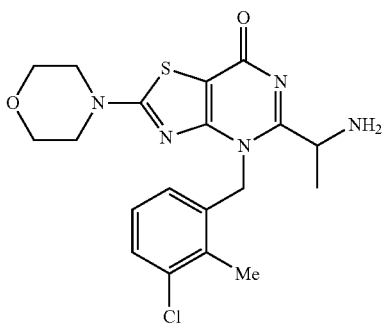 [SMILES: Cc1c(Cl)cccc1Cn1c(C(C)N)nc(=O)c2sc(N3CCOCC3)nc21]

The preparation of 5-(1-aminoethyl)-4-[(3-chloro-2-methylphenyl)methyl]-2-(4-morpholinyl)[1,3]thiazolo[4,5-d]pyrimidin-7(4H)-one a) 5-(1-bromoethyl)-4-[(3-chloro-2-methylphenyl)methyl]-2-(4-morpholinyl)[1,3]thiazolo[4,5-d]pyrimidin-7(4H)-one

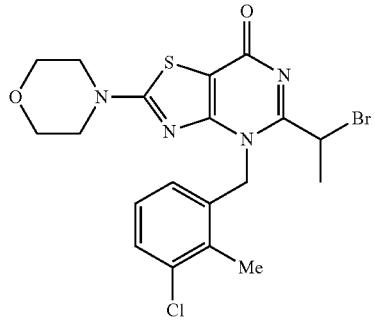 [SMILES: Cc1c(Cl)cccc1Cn1c(C(C)N=[N+]=[N-])nc(=O)c2sc(N3CCOCC3)nc21]

In a 100 mL round bottom flask combined 4-[(3-chloro-2-methylphenyl)methyl]-5-ethyl-2-(4-morpholinyl)[1,3]thiazolo[4,5-d]pyrimidin-7(4H)-one (4.1 g, 10.13 mmol) (Example 75) and sodium acetate (1.246 g, 15.19 mmol) in acetic acid (30 mL). Bromine (0.782 mL, 15.19 mmol) in acetic acid (5 mL) was added dropwise over ~3 min. The red colored reaction was stirred at room temperature for 16 hr. LC/MS indicated complete conversion to product. This reaction mixture was diluted with water (150 mL), producing a gummy yellow residue. The mixture was extracted with chloroform (100 mL), then concentrated to a thick yellow oil. This oil was triturated from ether (150 mL), to provide, after sonication a yellow solid that is consistent with 5-(1-bromoethyl)-4-[(3-chloro-2-methylphenyl)methyl]-2-(4-morpholinyl)[1,3]thiazolo[4,5-d]pyrimidin-7(4H)-one (4.52 g, 9.34 mmol, 92% yield). The proton NMR is consistent for the desired product. LC/MS m/z MH$^+$=484 (theoretical), found=484.9, $^1$H NMR (400 MHz, CHLOROFORM-d) S ppm 1.97 (d, J=6.57 Hz, 3H) 2.51 (s, 3H) 3.52-3.64 (m, 4H) 3.71-3.84 (m, 4H) 4.53-4.65 (m, 1H) 5.43 (d, J=17.43 Hz, 1H) 5.95 (d, J=17.43 Hz, 1H) 6.38 (d, J=7.83 Hz, 1H) 7.06 (t, J=8.08 Hz, 1H) 7.34 (d, J=7.83 Hz, 1H)

b) 5-(1-azidoethyl)-4-[(3-chloro-2-methylphenyl)methyl]-2-(4-morpholinyl)[1,3]thiazolo[4,5-d]pyrimidin-7(4H)-one

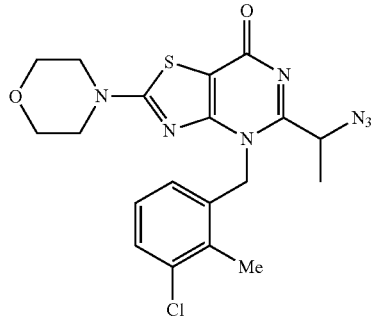

To a solution of sodium azide (20.16 mg, 0.310 mmol) in N,N-Dimethylformamide (DMF) (1.5 mL) was added 5-(1-bromoethyl)-4-[(3-chloro-2-methylphenyl)methyl]-2-(4-morpholinyl)[1,3]thiazolo[4,5-d]pyrimidin-7(4H)-one (100 mg, 0.207 mmol) in N,N-Dimethylformamide (DMF) (1.5 mL). The reaction was heated to 65° C. for 2 hr, and then the solution was cooled to room temperature. The reaction contents were diluted with water, producing a precipitate. The suspension was filtered using a fritted funnel, providing 5-(1-azidoethyl)-4-[(3-chloro-2-methylphenyl)methyl]-2-(4-morpholinyl)[1,3]thiazolo[4,5-d]pyrimidin-7(4H)-one (48 mg, 0.108 mmol, 52.1% yield) as a crude brown solid that was used directly in the next reaction. LC/MS m/z MH$^+$=446 (theoretical), found=446.1, $^1$H NMR (400 MHz, CHLOROFORM-d) δ ppm 1.67 (d, J=6.82 Hz, 4H) 2.47 (s, 3H) 3.48-3.66 (m, 5H) 3.68-3.87 (m, 5H) 3.97 (q, J=6.57 Hz, 1H) 5.42 (d, J=17.18 Hz, 1H) 5.76 (d, J=17.18 Hz, 1H) 6.41 (d, J=7.58 Hz, 1H) 7.07 (t, J=7.83 Hz, 1H) 7.35 (d, J=8.08 Hz, 1H)

c) 5-(1-aminoethyl)-4-[(3-chloro-2-methylphenyl) methyl]-2-(4-morpholinyl)[1,3]thiazolo[4,5-d]pyrimidin-7(4H)-one To a solution of 5-(1-azidoethyl)-4-[(3-chloro-2-methylphenyl)methyl]-2-(4-morpholinyl)[1,3]thiazolo[4,5-d]pyrimidin-7(4H)-one (48 mg, 0.108 mmol) in Tetrahydrofuran (THF) (1 mL) was added resin-bound triphenylphosphine (28.2 mg, 0.108 mmol) and the mixture was stirred at 60° C. overnight. The reaction was then quenched with water and stirred at 60° C. for 1 hr. The resin was removed by filtration and the filtrate was then extracted with dichloromethane. The organic solution was dried over sodium sulfate, filtered, and concentrated to provide the desired product as a brown solid. This crude material was purified on a silica gel column eluting with chloroform/(a solution of 2M ammonia in methanol) (99:1). The fractions containing product were combined, then concentrated to provide 5-(1-aminoethyl)-4-[(3-chloro-2-methylphenyl)methyl]-2-(4-morpholinyl) [1,3]thiazolo[4,5-d]pyrimidin-7(4H)-one (19 mg, 0.045 mmol, 42.0% yield). LC/MS m/z MH$^+$=420 (theoretical), found=420.1, $^1$H NMR (400 MHz, CHLOROFORM-d) δ ppm 1.44 (d, J=6.82 Hz, 3H) 2.48 (s, 3H) 3.53-3.63 (m, 4H) 3.72-3.85 (m, 5H) 4.02 (br. s., 1H) 5.42 (d, J=17.68 Hz, 1H) 5.78 (d, J=17.18 Hz, 1H) 6.49 (d, J=7.83 Hz, 1H) 7.07 (t, J=7.96 Hz, 1H) 7.34 (d, J=7.83 Hz, 1H)

Example 120

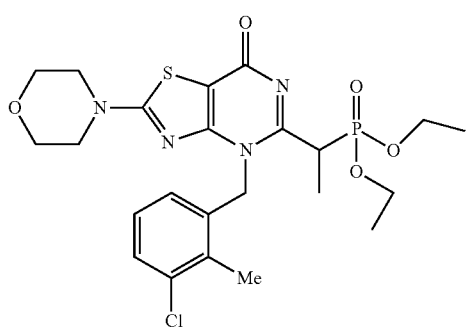 [SMILES: CCOP(=O)(OCC)C(C)c1nc(=O)c2sc(N3CCOCC3)nc2n1Cc1cccc(Cl)c1C]

The preparation of diethyl {1-[4-[(3-chloro-2-methylphenyl)methyl]-2-(4-morpholinyl)-7-oxo-4,7-dihydro[1,3]thiazolo[4,5-d]pyrimidin-5-yl]ethyl}phosphonate Added 5-(1-bromoethyl)-4-[(3-chloro-2-methylphenyl) methyl]-2-(4-morpholinyl)[1,3]thiazolo[4,5-d]pyrimidin-7 (4H)-one (179 mg, 0.370 mmol) and triethyl phosphite (4 mL, 22.87 mmol) to a 20 mL screw capped vial and stirred overnight (14 hours) at room temperature. The next morning, starting material was still present, so the contents were transferred to a 25 mL round bottom flask and the contents were heated to 155° C. for 2 hours, whereupon LC/MS showed that the bromo starting material was consumed and a molecular ion corresponding to the desired product was present along with an impurity (believed to be the des-bromo compound by LC/MS). The yellow solution was distilled to remove the unreacted triethyl phosphite, then the residue was purified by column chromatography on silica gel eluted with 0-10% of a (2N solution of NH$_3$ in methanol)/chloroform. The fractions containing product by TLC were combined, then concentrated to provide diethyl {1-[4-[(3-chloro-2-methylphenyl) methyl]-2-(4-morpholinyl)-7-oxo-4,7-dihydro[1,3]thiazolo [4,5-d]pyrimidin-5-yl]ethyl}phosphonate (51 mg, 0.094 mmol, 25.5% yield) as a light tan solid. LC/MS m/z MH$^+$=541 (theoretical), found=541.1, $^1$H NMR (400 MHz, CHLOROFORM-d) δ ppm 1.23-1.36 (m, 6H) 1.47 (dd, J=17.31, 6.95 Hz, 3H) 2.46 (s, 3H) 3.02-3.18 (m, 1H) 3.49-3.60 (m, 4H) 3.71-3.82 (m, 4H) 4.00-4.27 (m, 4H) 5.67 (d, J=-17.68 Hz, 1H) 5.90 (d, J=17.68 Hz, 1H) 6.41 (d, J=7.58 Hz, 1H) 7.05 (t, J=7.83 Hz, 1H) 7.32 (d, J=7.58 Hz, 1H)

Exemplary Capsule Composition

An oral dosage form for administering the present invention is produced by filing a standard two piece hard gelatin capsule with the ingredients in the proportions shown in Table II, below.

TABLE II

| INGREDIENTS | AMOUNTS |
| --- | --- |
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table III below, are mixed and granulated in the proportions shown with a 10% gelatin solution. The wet granules are screened, dried, mixed with the starch, talc and stearic acid, screened and compressed into a tablet.

TABLE III

| INGREDIENTS | AMOUNTS |
| --- | --- |
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of formula (I)

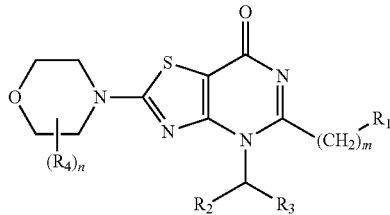

(I)

wherein
R1 is selected from the group consisting of: H, C1-3alkyl, —SC1-6alkyl, —OC1-6alkyl, NRaRb, hydroxy, —SH, NH—NH₂, C3-6cycloalkyl, C4-6heterocycloalkyl, —SO₂Ph, —OPh, —SPh, —SO₂(C1-3alkyl), —O(arylalkyl), and phenyl;
R2 is H or C1-3alkyl;
R3 is selected from the group consisting of: C1-6alkyl, C3-7cycloalkyl, C4-6heterocycloalkyl, alkylcarboxy, aryl, arylalkyl, and heteroaryl;
each R4 is independently selected from the group consisting of: C1-3alkyl, alkoxy, amide, and ester;
n is 0-2; m is 0-3; and
Ra and Rb are each independently H, or C1-3alkyl;
or a pharmaceutically acceptable salt thereof.

2. The compound of claim 1, wherein R1 is selected from the group consisting of: H, C1-3alkyl, —OC1-6alkyl, —SC1-6alkyl, NH₂, NHMe, and cyclopropyl; and R3 is C1-6alkyl or aryl.

3. The compound of according to claim 1, wherein R1 is selected from the group consisting of: H, C1-3alkyl, hydroxy, NH₂, and NHMe; R3 is a phenyl or napthyl group which may be substituted with one to five substituents selected from the group consisting of: C1-6alkyl, halogen and alkoxy; each R4 is independently selected from the group consisting of: C1-3alkyl, amide, and ester; m is 0-1.

4. The compound according to claim 1, wherein R1 is selected from the group consisting of: H, C1-3alkyl and hydroxy; R3 is a phenyl group which may be substituted with one to five substituents selected from the group consisting of: C1-6alkyl, halogen and alkoxy; each R4 is independently C1-3alkyl; and m is 0-1.

5. The compound according to claim 1, wherein m is 0-1.

6. The compound of claim 2, which is represented by Formula (I)(A)

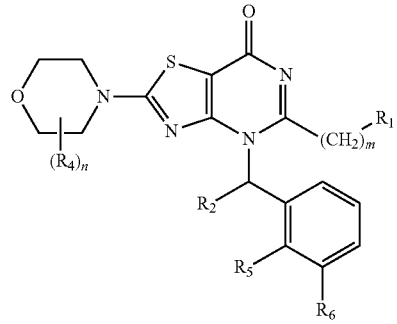

(I)(A)

wherein R5 and R6 are each independently selected from the group consisting of: C1-3alkyl, halogen, hydrogen, alkoxy, amino, cyano, hydroxy, amide and acyl.

7. The compound of claim 1 wherein R1 is selected from the group consisting of: H, C1-3alkyl, —OC1-6alkyl, —SMe, NH₂, NHMe, and cyclopropyl; and R3 is a thienyl or pyridinyl group which may be substituted with one to five substituents selected from the group consisting of: C1-6alkyl, halogen and alkoxy.

8. A compound which is 5-methyl-4-{[2-methyl-3-(trifluoromethyl)phenyl]methyl}-2-(4-morpholinyl)[1,3]thiazolo[4,5-d]pyrimidin-7(4H)-one, or a pharmaceutically acceptable salt thereof.

9. A compound which is 4-[(3-chloro-2-methylphenyl)methyl]-5-ethyl-2-(4-morpholinyl)[1,3]thiazolo[4,5-d]pyrimidin-7(4H)-one, or a pharmaceutically acceptable salt thereof.

10. A pharmaceutical composition comprising a compound according to claim 1 and a pharmaceutically acceptable carrier.

* * * * *